(12) United States Patent
Kortagere et al.

(10) Patent No.: US 12,162,891 B2
(45) Date of Patent: *Dec. 10, 2024

(54) GLUTAMATE TRANSPORTER ACTIVATORS AND METHODS USING SAME

(71) Applicant: Drexel University, Philadelphia, PA (US)

(72) Inventors: Sandhya Kortagere, Newtown, PA (US); Andreia C. K. Mortensen, Narbeth, PA (US); Ole V. Mortensen, Narbeth, PA (US); Joseph M. Salvino, Chester Springs, PA (US)

(73) Assignee: Drexel University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/847,490

(22) Filed: Jun. 23, 2022

(65) Prior Publication Data

US 2022/0402938 A1 Dec. 22, 2022

Related U.S. Application Data

(63) Continuation of application No. 16/477,946, filed as application No. PCT/US2018/013867 on Jan. 16, 2018, now Pat. No. 11,377,452.

(60) Provisional application No. 62/446,550, filed on Jan. 16, 2017.

(51) Int. Cl.
| | | |
|---|---|---|
| *C07D 495/04* | (2006.01) |
| *A61P 25/28* | (2006.01) |
| *C07D 401/14* | (2006.01) |
| *C07D 403/04* | (2006.01) |
| *C07D 405/14* | (2006.01) |

(52) U.S. Cl.
CPC ............ *C07D 495/04* (2013.01); *A61P 25/28* (2018.01); *C07D 401/14* (2013.01); *C07D 403/04* (2013.01); *C07D 405/14* (2013.01)

(58) Field of Classification Search
CPC ..................................................... A61K 47/55
See application file for complete search history.

(56) References Cited

U.S. PATENT DOCUMENTS

| | | | |
|---|---|---|---|
| 5,106,851 A | 4/1992 | Turconi et al. |
| 5,591,751 A | 1/1997 | Fujioka et al. |
| 6,329,389 B1 | 12/2001 | Suzuki et al. |
| 11,377,452 B2 * | 7/2022 | Kortagere ............ A61K 31/496 |
| 2002/0115688 A1 | 8/2002 | Beart et al. |
| 2005/0054619 A1 | 3/2005 | Ikonomidou |
| 2009/0163545 A1 | 6/2009 | Goldfarb et al. |
| 2010/0210836 A1 | 8/2010 | Neamati et al. |

OTHER PUBLICATIONS

CA registry No. 460330-76-1, entered into CA registry File on Oct. 10, 2002, supplied by Ambinter. (Year: 2002).
Goldfarb, "Chemical Abstract vol. 151 No. 92837, abstract for US 2009/0163545. (Year: 2009)".
Goldfarb, "Chemical Abstract, vol. 151, No. 92840, abstract for US 2009/0163545. (Year: 2009)".

* cited by examiner

*Primary Examiner* — Paul V Ward
(74) *Attorney, Agent, or Firm* — Saul Ewing LLP; Kathryn R. Doyle; Domingos J. Silva

(57) ABSTRACT

The present invention provides compounds useful for treating, ameliorating or preventing a disease or disorder that is caused, induced or characterized by abnormal reduction in glutamate transporter activity or abnormal increase in extracellular CNS glutamate concentration in a subject. In certain embodiments, the compound stimulates a glutamate transporter.

23 Claims, 25 Drawing Sheets

|  | Vehicle | GT949 (1 nM) |
|---|---|---|
| $V_{max}$ (pmol/mg/min) | 270.3 ± 15 | 399.3 ± 28 *** |
| $K_M$ (μM) | 43.3 ± 7 | 61.6 ± 13 |

|  | Vehicle | GT951 (1 nM) |
|---|---|---|
| $V_{max}$ (pmol/mg/min) | 293.4 ± 30 | 513.7 ± 47 ** |
| $K_M$ (μM) | 48.0 ± 16 | 62.6 ± 18 |

|  | Vehicle | GT939 (1 nM) |
|---|---|---|
| $V_{max}$ (pmol/mg/min) | 282 ± 26 | 430 ± 27 *** |
| $K_M$ (μM) | 43.5 ± 15 | 54.6 ± 12 |

| ID | R1 | R2 | R3 | R4 | R5 |
|---|---|---|---|---|---|
| GT949 | (3-methylcyclohexyl) | -H | -OMe | -H | -H |
| GT951 | (3-CF3 phenyl methyl) | -H | -OMe | -H | -H |
| GT835 | (benzodioxole-methyl) | -H | -CH$_3$ | -CH$_3$ | -H |
| GT867 | (benzodioxole-methyl) | -CH$_3$ | -H | -H | -CH$_3$ |
| GT729 | (furan-2-carbonyl) | -H | -CH$_3$ | -H | -CH$_3$ |
| GT996 | (furan-2-carbonyl) | -CH$_3$ | -H | -CH$_3$ | -H |

| ID | R1 |
|---|---|
| GT939 | —(CH$_2$)$_4$—O—(4-chloro-3-methylphenyl) |
| GT938 | —(CH$_2$)$_4$—O—(3,4-dimethylphenyl) |
| GT922 | —(CH$_2$)$_3$—O—(4-isopropylphenyl) |

FIG. 17

| ID | mechanism on EAAT2-mediated uptake | potency ($EC_{50}$ or $IC_{50}$) | M.W. | Log P |
|---|---|---|---|---|
| GT949 racemic | stimulates | $EC_{50}$ = 0.26 ± 0.03 nM | 527.66 | 4.20 |
| GT949A | stimulates | $EC_{50}$ = 0.041 ± 0.01 nM | 527.66 | 4.20 |
| GT949B | stimulates | $EC_{50}$ = 0.89 ± 0.42 nM | 527.66 | 4.20 |
| GT951 | stimulates | $EC_{50}$ = 0.8 ± 0.3 nM | 589.61 | 5.65 |
| GT939 | stimulates | $EC_{50}$ = 0.7 ± 0.02 nM | 437.96 | 4.87 |
| GT835 | inhibits | $IC_{50}$ = 12 ± 7 μM | 577.68 | 5.27 |
| GT729 | inhibits | $IC_{50}$ = 0.4 ± 0.09 μM | 537.61 | 3.54 |
| GT938 | inhibits | $IC_{50}$ = 23 ± 7 μM | 417.54 | 4.8 |
| GT922 | inhibits | $IC_{50}$ = 2.4 ± 0.8 μM | 445.60 | 5.47 |
| GT996 | does not affect | N/A | 537.61 | 3.54 |
| GT867 | does not affect | N/A | 577.68 | 5.27 |
| GT988 | does not affect | N/A | 587.76 | 5.99 |

GLUTAMATE TRANSPORTER ACTIVATORS AND METHODS USING SAME

CROSS-REFERENCE TO RELATED APPLICATIONS

The present application is a continuation of, and claims priority to, U.S. patent application Ser. No. 16/477,946, filed Jul. 15, 2019, now U.S. Pat. No. 11,377,452, which is a 35 U.S.C. § 371 national phase application from, and claims priority to, International Application No. PCT/US2018/013867, filed Jan. 16, 2018, and published under PCT Article 21(2) in English, which claims priority under 35 U.S.C. § 119(e) to U.S. Provisional Patent Application No. 62/446,550, filed Jan. 16, 2017, all of which applications are incorporated herein by reference in their entireties.

BACKGROUND OF THE INVENTION

Glutamate is the predominant excitatory amino acid neurotransmitter in the mammalian central nervous system (CNS) and is essential for normal brain function, including cognition, memory, learning, developmental plasticity and long-term potentiation. The termination of glutamate neurotransmission is achieved by rapid uptake of the released glutamate by presynaptic and astrocytic sodium-dependent transporters. There are five subtypes of excitatory amino-acid transporters or glutamate transporters: EAAT1 or GLAST, EAAT2 or GLT-1, EAAT3 or EAAC1, EAAT4, and EAAT5. The major regulator of extracellular glutamate levels in the brain is EAAT2, which is expressed in astroglial cells and responsible for about 90% total glutamate uptake in the CNS and about 1% of total brain protein in the CNS.

Glutamate translocation is a multi-step process that uses energy derived from $Na^+$ and $K^+$ electrochemical gradients to move glutamate against its concentration gradient. The rate-limiting step in the cycle involves translocation of $K^+$ and reorientation of the carrier to become accessible for a new substrate molecule in the synaptic cleft. Despite the identification of several crystal structures of a bacterial homolog of glutamate transporters Glt(ph), no rationally designed transporter activator has been identified so far.

Ischemic events in humans and in animals lead to an acute and sustained increase in extracellular glutamate concentrations, indicative of a lack of timely clearance by glutamate transporters. In fact, dysfunctional glutamate transporters are often the initiating event or part of the cascade leading to brain injury. Reductions in EAAT2 activity result in increased predisposition for seizures and susceptibility to damage due to ischemia. Excessive activation of glutamate receptors due to sustained elevation of extracellular glutamate levels results in $Ca^{2+}$ influx and activation of a cascade of phospholipases, endonucleases and proteases such as calpain that can lead to apoptotic or necrotic cell death. Glutamate excitotoxicity has been implicated in acute pathologies, such as traumatic brain injury, hyperexcitability, seizures and epilepsy, stroke, cerebral and retinal ischemia, and chronic pathologies, such as amyotrophic lateral sclerosis (ALS), Alzheimer's Disease, Huntington's Disease, neuropathic pain, and HIV-associated neurocognitive disorder. Also, ischemic events in humans and animals lead to an acute and sustained increase in extracellular glutamate concentrations, which suggests a lack of proper clearance by glutamate transporters. In fact, dysfunctional glutamate transporters are often the initiating event or part of the cascade leading to brain injury.

Reductions in EAAT2 activity result in increased predisposition for seizures and susceptibility to damage due to ischemia. Knockout of the EAAT2 gene resulted in exacerbated damage compared to their wild-type counterparts following cerebral injury in mice and controlled cortical impact in rats. Additionally, a transgenic approach for EAAT2 overexpression with double transgenic mice created from crossing an ALS mouse model to a mouse model overexpressing EAAT2 resulted in animals that display delayed grip strength decline, motor neuron loss, and increased life expectancy.

Several classes of compounds that target stages in these processes, such as NMDA receptor antagonists and calcium influx inhibitors, alleviate cellular damage and neurologic deficits to some extent, but have limited clinical use due to substantial side effects. Transcriptional or translational upregulators of EAAT2, such as GPI-1046, ceftriaxone, harmine and pyridazine derivatives, are neuroprotective through selective augmentation of EAAT2 expression. Nevertheless, these compounds must be administered prophylactically to be neuroprotective, and thus they have low clinical relevance for acute conditions. Some compounds with neuroprotective properties, such as MS-153, riluzole, guanosine and nicergoline, acutely stimulate glutamate uptake by an indirect modulation of transporter activity, but are non-specific and cause numerous side effects.

Currently there is a critical lack of compounds that activate, stimulate and/or upregulate the activity of glutamate transporters, such as but not limited to EAAT2. Such compounds should be used to treat diseases or disorders that are caused, induced or characterized by abnormal reduction in glutamate transporter activity or abnormal increase in extracellular CNS glutamate concentration in a subject. The present invention fulfills this need.

BRIEF SUMMARY OF THE INVENTION

The invention provides a compound of formula (I), or an enantiomer, diastereoisomer, salt or solvate thereof:

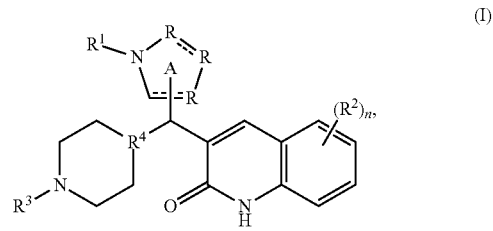

wherein in (I),
each ═══ bond in ring A is independently a double or a single covalent bond, wherein: (i) when a ═══ bond is a double covalent bond, each R group substituted at the bond is independently selected from the group consisting of N, CH and C($C_1$-$C_6$ alkyl), wherein the alkyl group is optionally substituted; and (ii) when a ═══ bond is a single covalent bond, each R group substituted at the bond is independently selected from the group consisting of NH, N($C_1$-$C_6$ alkyl), S, O, $CH_2$, CH($C_1$-$C_6$ alkyl) and C($C_1$-$C_6$ alkyl)$_2$, wherein the alkyl group is optionally substituted;
$R^1$ is selected from the group consisting of —$C_1$-$C_6$ alkyl, —$C_1$-$C_6$ heteroalkyl, —($C_0$-$C_3$ alkyl)-($C_3$-$C_6$ cycloalkyl), —($C_0$-$C_3$ alkyl)-($C_4$-$C_{10}$ heterocyclyl), —($C_0$-$C_3$ alkyl)-($C_6$-$C_{10}$ aryl) and —($C_0$-$C_3$ alkyl)-($C_5$-$C_{10}$ heteroaryl), wherein the alkyl, heteroalkyl, cycloalkyl, heterocyclyl, aryl and heteroaryl groups are independently optionally substituted;

each occurrence of $R^2$ is independently selected from the group consisting of H, —$C_1$-$C_6$ alkyl, —OH, —$C_1$-$C_6$ alkoxy, halogen, —$NH_2$, —$N(CH_3)_2$, —C(=O)OH, trifluoromethyl, —C(=O)O($C_1$-$C_4$)alkyl, —C(=O)$NH_2$, —$SO_2NH_2$, —C(=NH)$NH_2$, and —$NO_2$;

n is an integer ranging from 0 to 4;

$R^3$ is selected from the group consisting of —(C=O)$_{0-1}$($C_1$-$C_6$ alkyl), —(C=O)$_{0-1}$($C_1$-$C_6$ heteroalkyl), —(C=O)$_{0-1}$($C_0$-$C_3$alkyl)-($C_3$-$C_6$ cycloalkyl), —(C=O)$_{0-1}$($C_0$-$C_3$alkyl)-($C_4$-$C_{10}$ heterocyclyl), —(C=O)$_{0-1}$($C_0$-$C_3$ alkyl)-($C_6$-$C_{10}$ aryl), —(C=O)$_{0-1}$($C_0$-$C_3$ alkyl)-($C_5$-$C_{10}$ heteroaryl), —($SO_2$)$_{0-1}$($C_1$-$C_6$ alkyl), —($SO_2$)$_{0-1}$($C_1$-$C_6$ heteroalkyl), —($SO_2$)$_{0-1}$($C_0$-$C_3$ alkyl)-($C_3$-$C_6$ cycloalkyl), —($SO_2$)$_{0-1}$($C_0$-$C_3$ alkyl)-($C_4$-$C_{10}$ heterocyclyl), —($SO_2$)$_{0-1}$($C_0$-$C_3$ alkyl)-($C_6$-$C_{10}$ aryl) and —($SO_2$)$_{0-1}$($C_0$-$C_3$ alkyl)-($C_5$-$C_{10}$ heteroaryl), wherein the alkyl, heteroalkyl, cycloalkyl, heterocyclyl, aryl and heteroaryl groups are independently optionally substituted; and, $R^4$ is N or CH.

The invention provides a compound of formula (II), or an enantiomer, diastereoisomer, salt or solvate thereof:

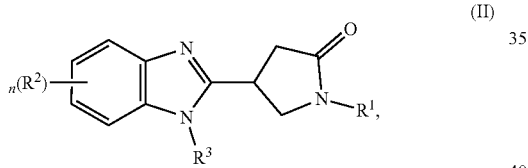

(II)

wherein in (II):

$R^1$ is selected from the group consisting of —$C_1$-$C_6$ alkyl, —$C_2$-$C_6$ alkenyl, —$C_2$-$C_6$ alkynyl, —$C_1$-$C_6$ heteroalkyl, —$C_1$-$C_6$ heteroalkenyl and —$C_1$-$C_6$ heteroalkynyl, wherein the alkyl, alkenyl, alkynyl, heteroalkyl, heteroalkenyl and heteroalkynyl are independently optionally substituted;

each occurrence of $R^2$ is independently selected from the group consisting of H, —$C_1$-$C_6$ alkyl, —OH, —$C_1$-$C_6$ alkoxy, halogen, —$NH_2$, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$;

n is an integer ranging from 0 to 4;

$R^3$ is selected from the group consisting of —($C_1$-$C_6$ alkyl)-$O_x$—($C_3$-$C_6$ cycloalkyl), —($C_1$-$C_6$ alkyl)-$O_x$—($C_4$-$C_{10}$ heterocyclyl), —($C_1$-$C_6$alkyl)-$O_x$—($C_6$-$C_{10}$ aryl) and —($C_1$-$C_6$alkyl)-$O_x$—($C_5$-$C_{10}$ heteroaryl), wherein the alkyl, cycloalkyl, heterocyclyl, aryl and heteroaryl groups are independently optionally substituted; and x is 0 or 1.

The invention provides a compound of formula (III), or an enantiomer, diastereoisomer, salt or solvate thereof:

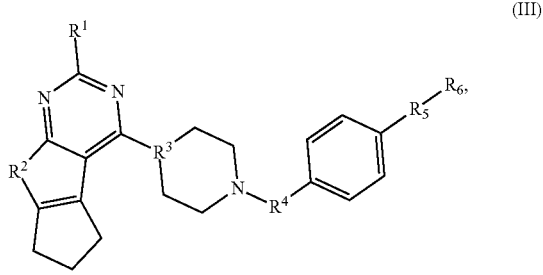

(III)

wherein in (III):

$R^1$ is selected from the group consisting of —($C_0$-$C_3$ alkyl)-($C_6$-$C_{10}$ aryl) and —($C_0$-$C_3$ alkyl)-($C_5$-$C_{10}$ heteroaryl), wherein the alkyl, aryl and heteroaryl groups are independently optionally substituted;

$R^2$ is NH, $NR^6$, S or O;

$R^3$ is N or CH;

$R^4$ is —C(=O)— or —S(=O)$_2$—;

$R^5$ is —C(=O)— or —S(=O)$_2$—; and, $R^6$ is selected from the group consisting of —$C_1$-$C_6$ alkyl, —$C_1$-$C_6$ heteroalkyl, —($C_0$-$C_3$ alkyl)-($C_3$-$C_6$ cycloalkyl), —($C_0$-$C_3$ alkyl)-($C_4$-$C_{10}$ heterocyclyl), —($C_0$-$C_3$ alkyl)-($C_6$-$C_{10}$ aryl) and —($C_0$-$C_3$ alkyl)-($C_5$-$C_{10}$ heteroaryl), wherein the alkyl, heteroalkyl, cycloalkyl, heterocyclyl, aryl and heteroaryl groups are independently optionally substituted.

In certain embodiments, the compound of formula (I) is selected from the group consisting of:

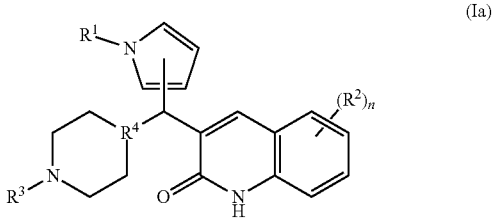

(Ia)

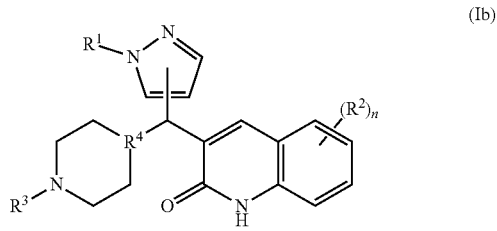

(Ib)

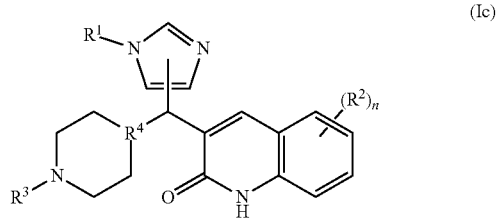

(Ic)

-continued

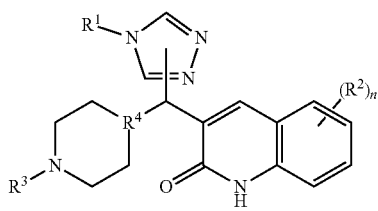
(Id)

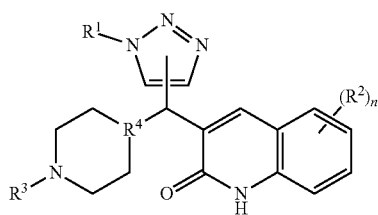
(Ie)

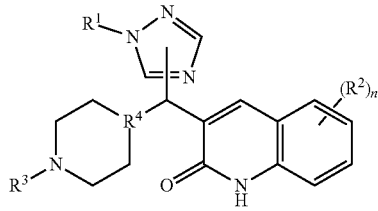
(If)

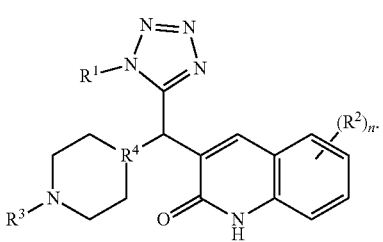
(Ig)

In certain embodiments, in the compound of Formula (I), $R^1$ is selected from the group consisting of —($C_1$-$C_3$ alkyl)-($C_3$-$C_6$ cycloalkyl), —($C_1$-$C_3$ alkyl)-($C_4$-$C_{10}$ heterocyclyl), —($C_1$-$C_3$ alkyl)-($C_6$-$C_{10}$ aryl) and —($C_1$-$C_3$ alkyl)-($C_5$-$C_{10}$ heteroaryl), wherein the alkyl, cycloalkyl, heterocyclyl, aryl and heteroaryl groups are independently optionally substituted.

In certain embodiments, in the compound of Formula (I), $R^1$ is selected from the group consisting of —($C_1$-$C_3$ alkyl)-($C_6$-$C_{10}$ aryl) and —($C_1$-$C_3$ alkyl)-($C_5$-$C_{10}$ heteroaryl), wherein the alkyl, aryl and heteroaryl groups are independently optionally substituted.

In certain embodiments, in the compound of Formula (I), each occurrence of $R^2$ is independently selected from the group consisting of H, —$C_1$-$C_6$ alkyl, —OH, —$C_1$-$C_6$ alkoxy, halogen, —$NH_2$, —$N(CH_3)_2$, —C(=O)OH, trifluoromethyl, —C≡N and —$NO_2$.

In certain embodiments, in the compound of Formula (I), $R^3$ is selected from the group consisting of —($C_1$-$C_6$ alkyl), —($C_1$-$C_6$ heteroalkyl), —($C_0$-$C_3$ alkyl)-($C_3$-$C_6$ cycloalkyl), —($C_0$-$C_3$ alkyl)-($C_4$-$C_{10}$ heterocyclyl), —($C_0$-$C_3$ alkyl)-($C_6$-$C_{10}$ aryl), —($C_0$-$C_3$ alkyl)-($C_5$-$C_{10}$ heteroaryl), —(C=O)($C_0$-$C_3$alkyl)-($C_6$-$C_{10}$ aryl), and —(C=O)($C_0$-$C_3$alkyl)-($C_5$-$C_{10}$ heteroaryl), wherein the alkyl, heteroalkyl, cycloalkyl, heterocyclyl, aryl and heteroaryl groups are independently optionally substituted.

In certain embodiments, in the compound of Formula (I), n is 2 or 3.

In certain embodiments, the compound of Formula (I) is:

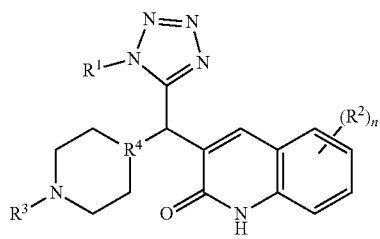
(Ig).

In certain embodiments, the compound of Formula (I) is:

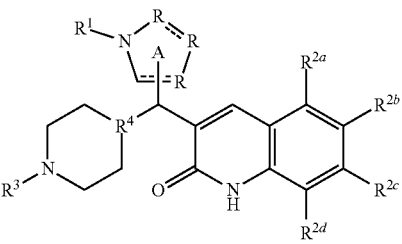
(Ih), wherein $R^{2a}$, $R^{2c}$, and $R^{2d}$ are independently selected from the group consisting of H and $C_1$-$C_6$ alkyl, and $R^{2b}$ is OH or $C_1$-$C_6$ alkoxy. In certain embodiments, $R^{2a}$, $R^{2c}$, and $R^{2d}$ are each H. In certain embodiments, the compound of Formula (I) is:

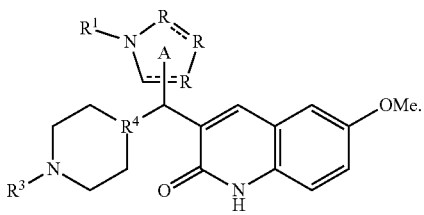
(Ii)

In certain embodiments, the compound of Formula (I) is:

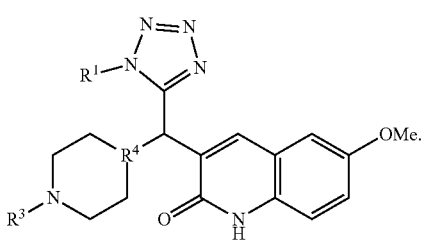
(Ij)

In certain embodiments, in the compound of formula (I) $R^3$ is optionally substituted cyclohexyl or phenyl.

In certain embodiments, the compound of Formula (I) is selected from the group consisting of: 3-((4-cyclohexylpiperazin-1-yl)(1-phenethyl-1H-tetrazol-5-yl)methyl)-6-methoxy-quinolin-2(1H)-one (GT949); 6-methoxy-3-((1- phenethyl-1H-tetrazol-5-yl)(4-(3-(trifluoromethyl)phenyl) piperazin-1-yl)methyl)quinolin-2(1H)-one (GT951); 3-((4-(benzo[d][1,3]dioxol-5-ylmethyl)piperazin-1-yl)(1-phenethyl-1H-tetrazol-5-yl)methyl)-6,7-dimethylquinolin-2 (1H)-one (GT835); 3-((4-(furan-2-carbonyl)piperazin-1-yl) (1-phenethyl-1H-tetrazol-5-yl)methyl)-6,8-dimethylquinolin-2(1H)-one (GT729); 3-((4-(furan-2-carbonyl)piperazin-1-yl)(1-phenethyl-1H-tetrazol-5-yl) methyl)-5,7-dimethylquinolin-2(1H)-one (GT996); 3-((4-(benzo[d][1,3]dioxol-5-ylmethyl)piperazin-1-yl)(1-phenethyl-1H-tetrazol-5-yl)methyl)-5,8-dimethylquinolin-2 (1H)-one (GT867); an enantiomer, diastereoisomer, salt or solvate thereof, and any mixtures thereof.

In certain embodiments, in the compound of Formula (II), n is 0. In certain embodiments, in the compound of Formula (II), x is 1. In certain embodiments, in the compound of Formula (II), $R^1$ is selected from the group consisting of —$C_2$-$C_6$ alkenyl and —$C_2$-$C_6$ alkynyl, wherein the alkenyl and alkynyl are independently optionally substituted. In certain embodiments, in the compound of Formula (II), $R^3$ is selected from the group consisting of —($C_1$-$C_6$alkyl)-$O_x$—($C_6$-$C_{10}$ aryl) and —($C_1$-$C_6$alkyl)-$O_x$—($C_5$-$C_{10}$ heteroaryl), wherein the alkyl, aryl and heteroaryl groups are independently optionally substituted.

In certain embodiments, the compound of Formula (II) is selected from the group consisting of: 1-allyl-4-(1-(4-(4-chloro-3-methylphenoxy)butyl)-1H-benzo[d]imidazol-2-yl) pyrrolidin-2-one (GT939); 1-allyl-4-(1-(4-(3,4-dimethylphenoxy)butyl)-1H-benzo[d] imidazol-2-yl)pyrrolidin-2-one (GT938); 1-allyl-4-(1-(3-(4-(sec-butyl)phenoxy) propyl)-1H-benzo[d]imidazol-2-yl)pyrrolidin-2-one (GT922); an enantiomer, diastereoisomer, salt or solvate thereof, and any mixtures thereof.

In certain embodiments, in the compound of Formula (III), $R^1$ is —$C_6$-$C_{10}$ aryl or —$C_5$-$C_{10}$ heteroaryl, wherein the aryl and heteroaryl groups are independently optionally substituted. In certain embodiments, in the compound of Formula (III), $R^2$ is S. In certain embodiments, in the compound of Formula (III), $R^3$ is N. In certain embodiments, in the compound of Formula (III), $R^4$ is —C(=O)—. In certain embodiments, in the compound of Formula (III), $R^5$ is —S(=O)$_2$—. In certain embodiments, in the compound of Formula (III), $R^6$ is —$C_1$-$C_6$ heteroalkyl or —$C_4$-$C_{10}$ heterocyclyl, wherein the heteroalkyl and heterocyclyl groups are independently optionally substituted.

In certain embodiments, the compound of Formula (III) is (4-(2-phenyl-6,7-dihydro-5H-cyclopenta[4,5] thieno[2,3-d] pyrimidin-4-yl)piperazin-1-yl)(4-(pyrrolidin-1-ylsulfonyl) phenyl) methanone (GT988), or an enantiomer, diastereoisomer, salt or solvate thereof.

In certain embodiments, the substituted alkyl, cycloalkyl (such as for example cyclohexyl), alkenyl, alkynyl, heteroalkyl, heteroalkenyl, heteroalkynyl, or heterocyclyl is independently substituted with at least selected from the group consisting of $C_1$-$C_6$ alkyl, —OH, $C_1$-$C_6$ alkoxy, halogen, NH$_2$, NH(CH$_3$), N(CH$_3$)$_2$, —C(=O)OH, trifluoromethyl, —C(=O)O($C_1$-$C_4$)alkyl, —C(=O)NH$_2$, —NHC(=O) (aryl or alkyl), —SO$_2$NH$_2$, —C(=NH)NH$_2$, —NO$_2$, or any combinations thereof.

In certain embodiments, the substituted phenyl or heteroaryl is independently substituted with at least selected from the group consisting of $C_1$-$C_6$ alkyl, —OH, $C_1$-$C_6$ alkoxy, halogen, NH$_2$, NH(CH$_3$), N(CH$_3$)$_2$, —C(=O)OH, trifluoromethyl, —C(=O)O($C_1$-$C_4$)alkyl, —C(=O)NH$_2$, —NHC(=O)(aryl or alkyl), —SO$_2$NH$_2$, —C(=NH)NH$_2$, —NO$_2$, or any combinations thereof.

The invention further provides a pharmaceutical composition comprising at least one compound of the invention and at least one pharmaceutically acceptable carrier.

The invention further provides a method of treating, ameliorating or preventing a disease or disorder that is caused, induced or characterized by abnormal reduction in glutamate transporter activity or abnormal increase in extracellular CNS glutamate concentration in a subject. In certain embodiments, the method comprises administering to the subject a therapeutically effective amount of at least one compound of the invention, or an enantiomer, diastereoisomer, salt or solvate thereof.

In certain embodiments, the disease or disorder is at least one selected from the group consisting of ischemia, seizure, traumatic brain injury, stroke, epilepsy, schizophrenia, and neurodegenerative diseases or disorders. In certain embodiments, the at least one compound of the invention activates, stimulates and/or upregulates the activity of a glutamate transporter in the subject. In certain embodiments, the transporter comprises EAAT2. In certain embodiments, administration of the at least one compound of the invention regulates extracellular glutamate concentrations in the subject. In certain embodiments, administration of the at least one compound of the invention increases, induces or upregulates removal of glutamate from the neuronal synaptic cleft into neuroglia and neurons of the subject. In certain embodiments, administration of the at least one compound of the invention inhibits glutamate transport in the subject.

In certain embodiments, the at least one compound of the invention is selected from the group consisting of: 1-allyl-4-(1-(4-(4-chloro-3-methylphenoxy)butyl)-1H-benzo[d] imidazol-2-yl)pyrrolidin-2-one; 3-((4-cyclohexylpiperazin-1-yl)(1-phenethyl-1H-tetrazol-5-yl)methyl)-6-methoxy-quinolin-2(1H)-one; 6-methoxy-3-((l-phenethyl-1H-tetrazol-5-yl)(4-(3-(trifluoromethyl) phenyl)piperazin-1-yl)methyl) quinolin-2(1H)-one; an enantiomer, diastereoisomer, salt or solvate thereof, and any mixtures thereof.

In certain embodiments, the at least one compound of the invention is selected from the group consisting of: (+)-3-((4-cyclohexylpiperazin-1-yl)(1-phenethyl-1H-tetrazol-5-yl)methyl)-6-methoxy-quinolin-2(1H)-one, (−)-3-((4-cyclohexylpiperazin-1-yl)(1-phenethyl-1H-tetrazol-5-yl)methyl)-6-methoxy-quinolin-2(1H)-one, (+)-6-methoxy-3-((l-phenethyl-1H-tetrazol-5-yl)(4-(3-(trifluoromethyl)phenyl) piperazin-1-yl)methyl)quinolin-2(1H)-one, (−)-6-methoxy-3-((1-phenethyl-1H-tetrazol-5-yl)(4-(3-(trifluoromethyl) phenyl)piperazin-1-yl)methyl)quinolin-2(1H)-one, and any mixtures thereof.

In certain embodiments, the at least one compound of the invention is administered to the subject as part of a pharmaceutical composition.

In certain embodiments, the subject is further administered at least one additional therapeutic agent. In certain embodiments, the at least one compound of the invention and the at least one additional therapeutic agent are co-administered to the subject. In certain embodiments, the at least one compound of the invention and the at least one additional therapeutic agent are co-formulated. In certain embodiments, the at least one compound of the invention is administered to the subject a given period of time before or after the at least one additional therapeutic agent is administered to the subject.

In certain embodiments, the subject is a mammal. In certain embodiments, the mammal is human

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIG. 3 (right) is a schematic representation of glutamate excitotoxicity, with high levels of glutamate are released from the pre-synapsis, resulting in over-activation of post-synaptic receptors leading to calpain/caspase activation resulting in neuronal death. Glutamate-mediated excitotoxicity is present in acute and chronic disorders/conditions such as ischemia, stroke, brain trauma, epilepsy, neurodegenerative disorders such as ALS and Huntington's disease, among others.

FIG. 5A: GT949 represented as a surface model using spheres with van der Waals radii and colored according to atom type (carbon=cyan, nitrogen=blue, and oxygen=red) docked at the binding site of the modeled structure of EAAT2. The residues lining the binding pocket are represented as licorice sticks and colored according to atom type. EAAT2 is represented as orange ribbons. FIG. 5B: Schematic representation of the interactions of GT949 in the binding pocket. The nature of interactions is described by the legend below the figure. FIG. 5C: Schematic representation of the interactions of GT951 in the binding pocket. The nature of interactions is described by the legend below the figure. FIGS. 5B-5C were generated using the ligand interactions module of the modeling software Molecular Operating Environment (MOE).

FIG. 6A: Outward facing model of EAAT2 illustrated as cartoon model and colored cyan. Binding pocket is formed by residues D83, G82, G360, A362, V191, T192, P81, I300, W472, D475, R476 and K157 are shown as red spheres. FIG. 6B illustrates the docked model of GT949 (shown in yellow surface model) in the binding pocket of EAAT2 suggesting a highly complementary ligand binding domain.

FIG. 13A illustrates background and specific signal of assays. Background, obtained in presence of TBOA, a specific inhibitor of glutamate transport, represents ~4.7% of the specific signal. In FIG. 13B, dose response curves of GT949 (racemic mixture and separated enantiomers, A and B) show that potencies for racemic mixture and separated enantiomers are 1, 0.5 and 15 nM, respectively. The efficacy of augmentation is ~58 and 50% for the racemic mixture and B enantiomer, while the A enantiomer is more efficacious, resulting in an 81% increase in transport. As shown in FIG. 13C, an $EC_{50}$ value of 0.3 nM and an efficacy of uptake enhancement of ~27% was observed for GT951. FIG. 13D illustrates results for GT996. Results are the mean±SEM of at least three independent experiments.

FIG. 17 comprises a table illustrating Structure-Activity Relationship (SAR) of certain compounds on EAAT2-Mediated Glutamate Uptake.

FIG. 19A: Modeled structure of EAAT2 represented as orange colored ribbons with residues chosen for pharmacophore design represented as licorice sticks and colored by atom type (carbon=cyan, oxygen=red, nitrogen=blue, and sulfur=yellow). FIG. 19B: Two-dimensional representation of the receptor based pharmacophore shown with residues represented as licorice sticks and labeled and the pharmacophore represented as dotted lines; the distances between chosen atoms are listed in angstroms.

FIG. 20A: Molecular superimpositioning of EAAT1 (transparent yellow ribbons) and EAAT2 (orange ribbons) suggests a conserved GltPh architecture but with significant differences in the arrangement of various domains. The positions of GT949 (EAAT2 allosteric inhibitor), TFB-TBOA (competitive inhibitor of both EAAT1 and EAAT2), and UCPH-101 (an allosteric modulator of EAAT1) are highlighted with green, red, and purple ovals. FIG. 20B: Close-up view of the binding pocket of GT949, TFB-TBOA, and UCPH-101 shown with the ligand represented in licorice stick model and colored by atom type (carbon=cyan, oxygen=red, and nitrogen=blue) and labeled. The view shows three distinct binding pockets for each of these molecules with no overlap between the EAAT1 and EAAT2 allosteric sites.

DETAILED DESCRIPTION OF THE INVENTION

Figure 1:
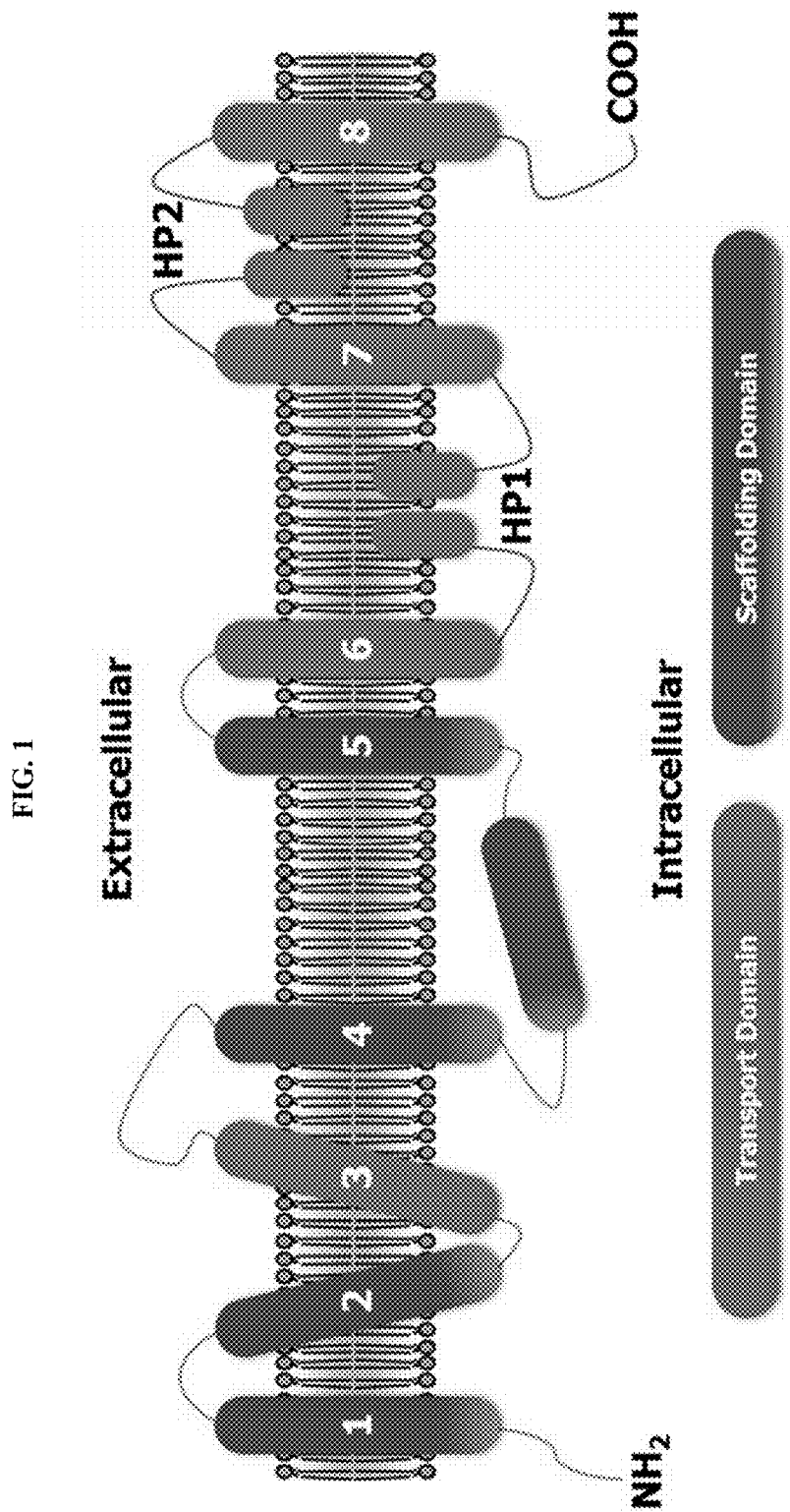
FIG. 1 is a non-limiting schematic representation of a glutamate transporter.
Figure 2:
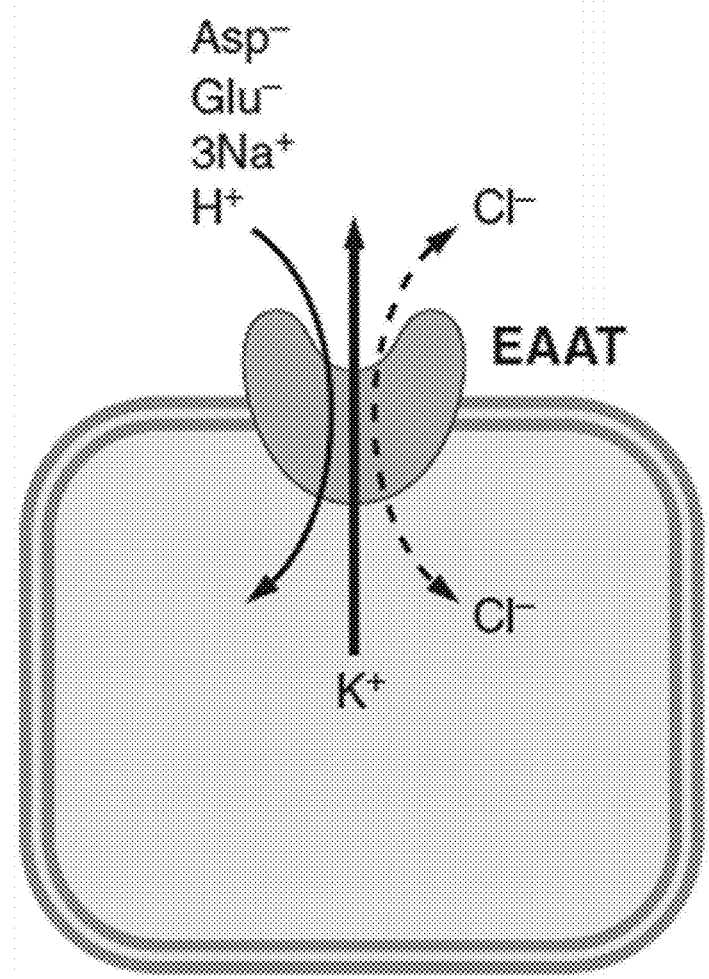
FIG. 2 is a schematic representation of the glutamate transport translocation cycle, depicting the multi-step process with energy for movement of glutamate derived from $Na^+$ and $K^+$ electrochemical gradients.
Figure 3:
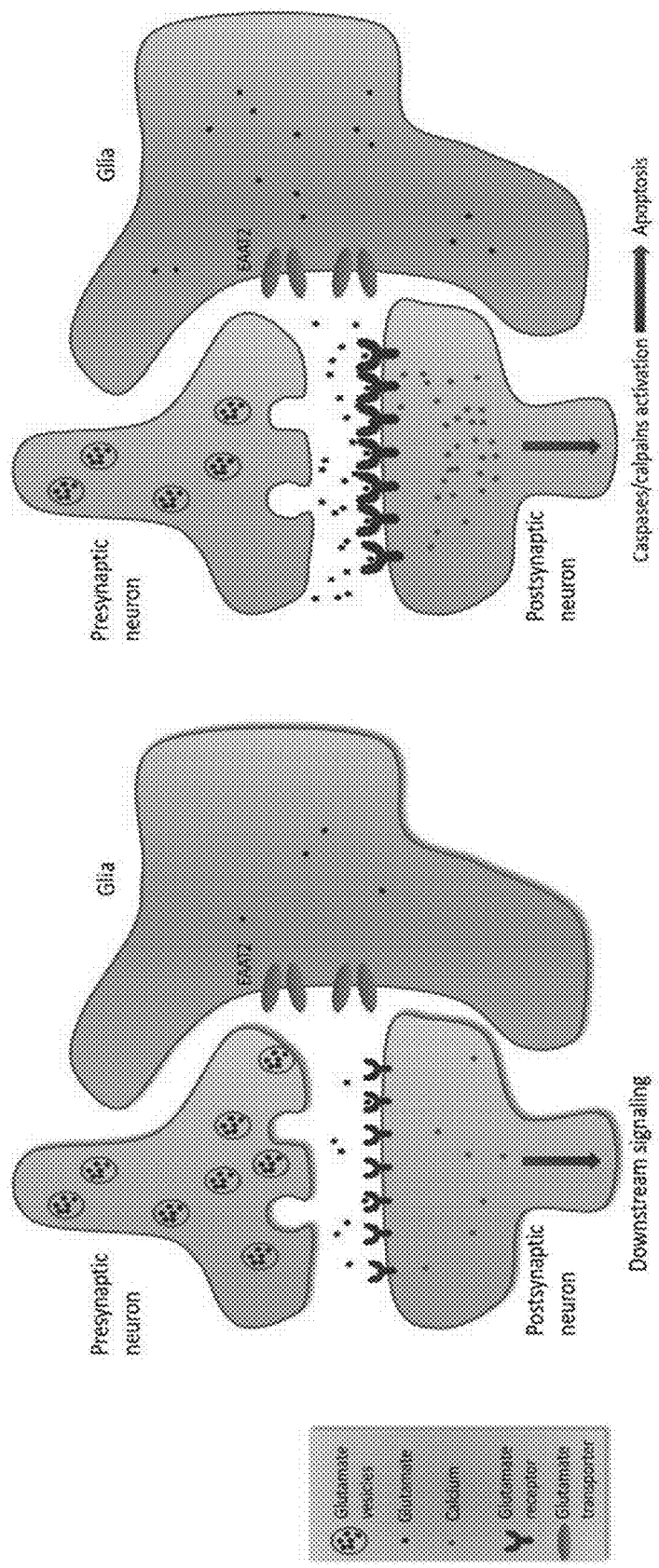
FIG. 3 (left) is a schematic representation of the physiological functioning state of a glutamatergic synapse, depicting glutamate that is stored in vesicles in the presynaptic neuron and released, activating glutamate receptors on the post-synaptic neurons, which results in $Na^+$ and $Ca^+$ influx and leads to depolarization and generation of action potential. Glutamate is removed by EAAT2 transporter located on astrocytes.
Figure 4:
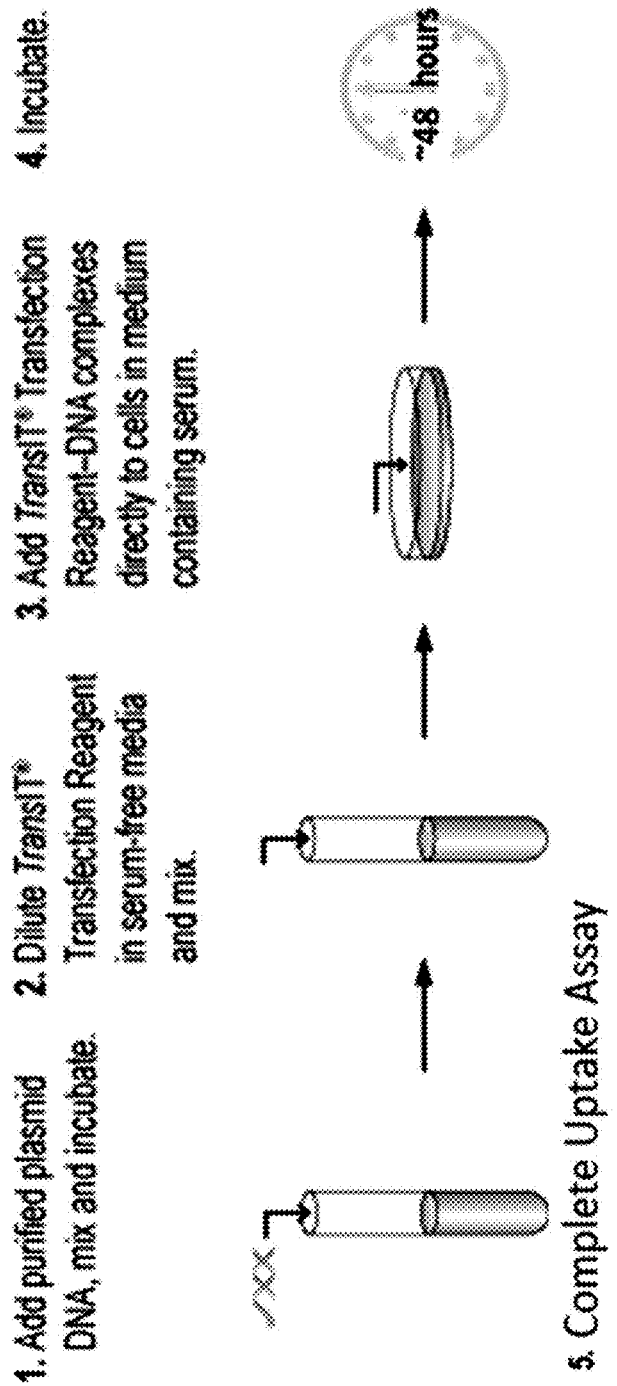
FIG. 4 is a schematic representation of cell transfection experiments described herein. The DNAs used (corresponding to EAAT1, EAAT2, and EAAT3 transporters) were transfected into monkey kidney cells (COS-7) using TRAN-SIT®-LT1 (Mirus Bio LLC, Madison, WI) as a lipofection reagent. 48 h after transfection uptake assays were performed.

The present invention relates to the unexpected discovery of small molecule compounds that can be used to activate, stimulate or upregulate the activity of a glutamate transporter. In certain embodiments, the transporter comprises EAAT2. In other embodiments, the compounds of the invention help regulate extracellular glutamate concentrations in a cell or a subject in need thereof. In yet other embodiments, the compounds of the invention increase, induce or upregulate removal (uptake) of glutamate from the neuronal synaptic cleft into neuroglia and neurons. In yet other embodiments, the compounds of the invention inhibit glutamate transport.

In one non-limiting aspect, direct activation of a glutamate transporter by compounds of the invention is a preferred therapeutic intervention as compared to treatments targeting glutamate receptors and/or $Ca^+$ influx, because glutamate release is a key early event in many excitotoxic conditions. In another non-limiting aspect, direct upregulation of glutamate transporter by compounds of the invention is a preferred therapeutic intervention as compared to indirect transport regulation, which has been linked to side effects in the clinic. In yet another non-limiting aspect, direct upregulation of glutamate transporter by compounds of the invention is a preferred therapeutic intervention as compared to treatments targeting NMDA receptors and $Ca^{2+}$ influx, which exhibit substantial side effects.

In certain embodiments, the compounds of the invention are useful in treating, ameliorating or preventing a disease or disorder that is caused, induced or characterized by abnormal reduction in glutamate transporter activity or abnormal increase in extracellular CNS glutamate concentration in a subject. In other embodiments, the disease or disorder is selected from the group consisting of cerebral and retinal ischemia, seizure, traumatic brain injury, stroke, epilepsy, schizophrenia, and neurodegenerative diseases or disorders (such as, but not limited to, Parkinson's disease, Alzheimer's disease, Huntington's disease, amyotrophic lateral sclerosis (ALS), ALS-parkinsonism dementia complex, and HIV-associated neurocognitive disorder (HAND).

As described herein, In the present work, knowledge derived from the structural elements was employed in a hybrid structure based (HSB) approach, using the crystal structure of the homologue transporter GltPh. Virtual screening identified 10 novel small molecules that interact within this unique region of EAAT2. These compounds were characterized for their selectivity to EAAT2, and their ability to allosterically activate or inhibit the function of EAAT2.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, illustrative methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "about" as used herein, when referring to a measurable value such as an amount, a temporal duration, and the like, is meant to encompass variations of ±20% or ±10%, for example ±5%, for example ±1%, for example ±0.1% from the specified value, as such variations are appropriate to perform the disclosed methods.

As used herein, the term "activator" or "stimulator" or "upregulator" as applied to a glutamate transporter refers to a compound that interacts with a glutamate transporter in a cell or a subject and increases, upregulates, enhances, or restores the activity of the transporter. In certain embodiments, a glutamate transporter activator regulates extracellular glutamate concentrations in a cell or a subject in need thereof. The normal activity level of a glutamate transporter may be determined by examining a cell or subject with a normally functioning glutamate transporter. An abnormal reduction in glutamate transporter activity or an abnormal increase in extracellular CNS glutamate concentration may cause a disease or disorder in the subject. In one aspect, dysfunctional glutamate transporters are often the initiating event or part of the cascade leading to brain injury, and reductions in glutamate transport activity result in increased predisposition for seizures and susceptibility to damage due to ischemia.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Illustrative examples are $C_1$-$C_3$ alkoxy, particularly ethoxy and methoxy.

As used herein, the term "alkyl" by itself or as part of another substituent means, unless otherwise stated, a straight or branched chain hydrocarbon having the number of carbon atoms designated (i.e., $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Examples include $C_1$-$C_6$ alkyl, particularly ethyl, methyl, isopropyl, isobutyl, n-pentyl, n-hexyl and cyclopropylmethyl. $C_0$ alkyl corresponds to a bond.

As used herein, the term "substituted alkyl" means alkyl, as defined above, substituted by one, two or three substituents selected from the group consisting of halogen, —OH, alkoxy, —NH$_2$, —N(CH$_3$)$_2$, —C(=O)OH, trifluoromethyl, —C(=O)O(C$_1$-C$_4$)alkyl, —C(=O)NH$_2$, —SO$_2$NH$_2$, —C(=NH)NH$_2$, and —NO$_2$, for example containing one or two substituents selected from halogen, —OH, alkoxy, —NH$_2$, trifluoromethyl, —N(CH$_3$)$_2$, and —C(=O)OH, for example selected from halogen, alkoxy and —OH.

Examples of substituted alkyls include, but are not limited to, 2,2-difluoropropyl, 2-carboxy cyclopentyl and 3-chloropropyl.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Illustrative examples are phenyl and naphthyl, or phenyl.

As used herein, the term "aryl-($C_1$-$C_3$ alkyl)" means a functional group wherein a one to three carbon alkylene chain is attached to an aryl group, e.g., —CH$_2$CH$_2$-phenyl. Illustrative examples are aryl-CH$_2$— and aryl-CH(CH$_3$)—. The term "substituted aryl-($C_1$-$C_3$ alkyl)" means an aryl-($C_1$-$C_3$ alkyl) functional group in which the aryl group is substituted. An illustrative example is substituted aryl (CH$_2$)—. Similarly, the term "heteroaryl-($C_1$-$C_3$ alkyl)" means a functional group wherein a one to three carbon alkylene chain is attached to a heteroaryl group, e.g., —CH$_2$CH$_2$-pyridyl. An illustrative example is heteroaryl-(CH$_2$)—. The term "substituted heteroaryl-($C_1$-$C_3$)alkyl" means a heteroaryl-($C_1$-$C_3$ alkyl) functional group in which the heteroaryl group is substituted. An illustrative example is substituted heteroaryl-(CH$_2$)—.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

As used herein, the terms "effective amount" and "pharmaceutically effective amount" and "therapeutically effective amount" refer to a nontoxic but sufficient amount of an agent or compound to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "GT729" refers to 3-((4-(furan-2-carbonyl)piperazin-1-yl)(1-phenethyl-1H-tetrazol-5-yl)methyl)-6,8-dimethylquinolin-2(1H)-one, or an enantiomer, salt or solvate thereof.

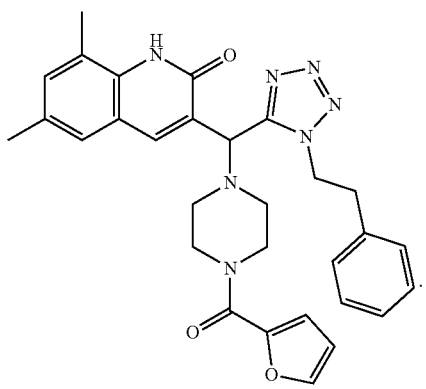 [SMILES: Cc1cc(C)c2[nH]c(=O)c(C(c3nnnn3CCc3ccccc3)N3CCN(C(=O)c4ccco4)CC3)cc2c1]

As used herein, the term "GT835" refers to 3-((4-(benzo[d][1,3]dioxol-5-ylmethyl) piperazin-1-yl)(1-phenethyl-1H-tetrazol-5-yl)methyl)-6,7-dimethylquinolin-2(1H)-one, or an enantiomer, salt or solvate thereof.

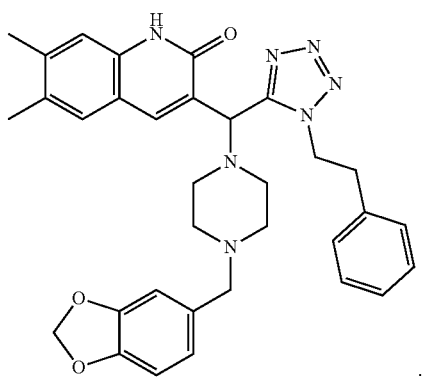 [SMILES: Cc1cc2cc(C(c3nnnn3CCc3ccccc3)N3CCN(Cc4ccc5c(c4)OCO5)CC3)c(=O)[nH]c2cc1C]

As used herein, the term "GT867" refers to 3-((4-(benzo[d][1,3]dioxol-5-ylmethyl) piperazin-1-yl)(1-phenethyl-1H-tetrazol-5-yl)methyl)-5,8-dimethylquinolin-2(1H)-one, or an enantiomer, salt or solvate thereof.

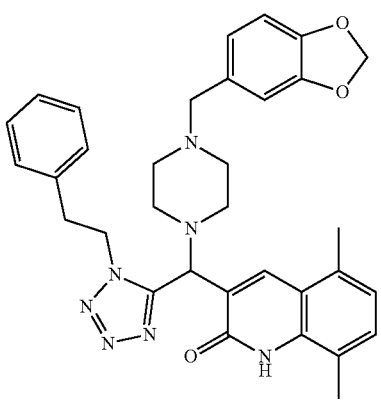

As used herein, the term "GT922" refers to 1-allyl-4-(1-(3-(4-(sec-butyl)phenoxy) propyl)-1H-benzo[d]imidazol-2-yl)pyrrolidin-2-one, or an enantiomer, diastereoisomer, salt or solvate thereof.

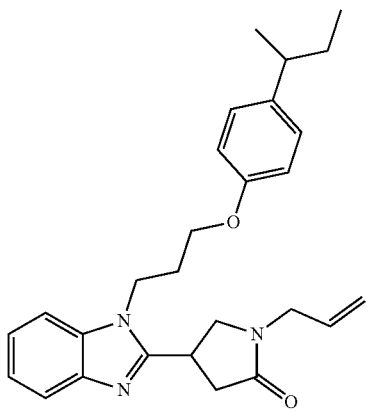

As used herein, the term "GT938" refers to 1-allyl-4-(1-(4-(3,4-dimethylphenoxy) butyl)-1H-benzo[d]imidazol-2-yl)pyrrolidin-2-one, or an enantiomer, salt or solvate thereof.

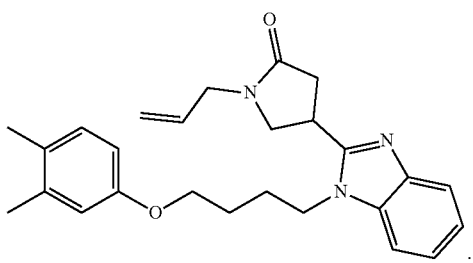 [SMILES: C=CCN1CC(c2nc3ccccc3n2CCCCOc2ccc(C)c(C)c2)CC1=O]

As used herein, the term "GT939" refers to 1-allyl-4-(1-(4-(4-chloro-3-methyl phenoxy)butyl)-1H-benzo[d]imidazol-2-yl)pyrrolidin-2-one, or an enantiomer, salt or solvate thereof.

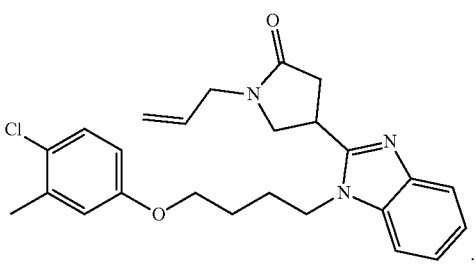 [SMILES: C=CCN1CC(c2nc3ccccc3n2CCCCOc2ccc(Cl)c(C)c2)CC1=O]

As used herein, the term "GT949" refers to 3-((4-cyclohexylpiperazin-1-yl)(1-phenethyl-1H-tetrazol-5-yl)methyl)-6-methoxy-quinolin-2(1H)-one, or an enantiomer, salt or solvate thereof.

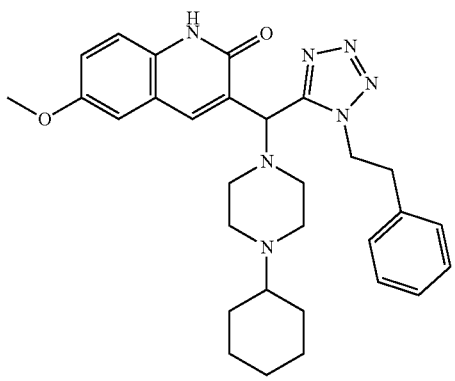

As used herein, the term "GT951" refers to 6-methoxy-3-((1-phenethyl-1H-tetrazol-5-yl)(4-(3-(trifluoromethyl)phenyl)piperazin-1-yl)methyl)quinolin-2(1H)-one, or an enantiomer, salt or solvate thereof.

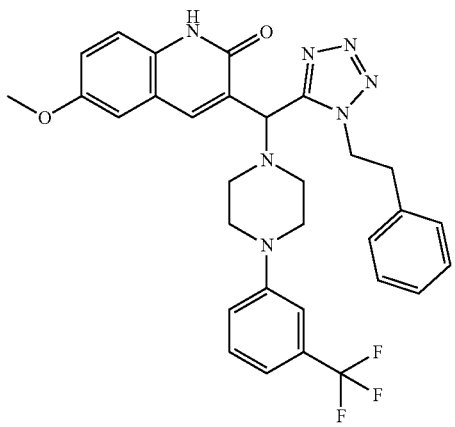

As used herein, the term "GT988" refers to (4-(2-phenyl-6,7-dihydro-5H-cyclopenta [4,5]thieno[2,3-d]pyrimidin-4-yl)piperazin-1-yl)(4-(pyrrolidin-1-ylsulfonyl)phenyl)methanone, or a salt or solvate thereof.

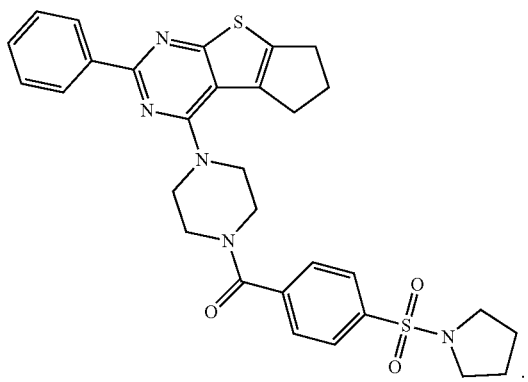 [SMILES: O=C(c1ccc(S(=O)(=O)N2CCCC2)cc1)N1CCN(c2nc(-c3ccccc3)nc3sc4c(c23)CCC4)CC1]

As used herein, the term "GT996" refers to 3-((4-(furan-2-carbonyl)piperazin-1-yl)(1-phenethyl-1H-tetrazol-5-yl)methyl)-5,7-dimethylquinolin-2(1H)-one, or a salt or solvate thereof.

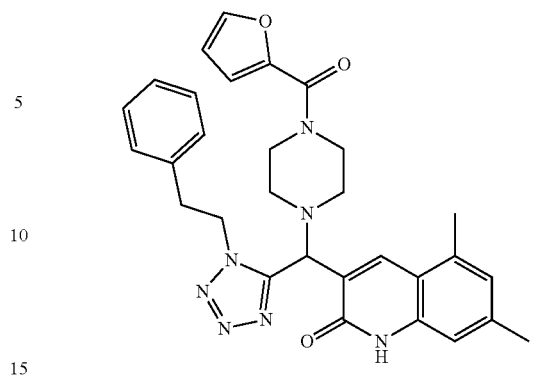

As used herein, the term "halo" or "halogen" alone or as part of another substituent means, unless otherwise stated, a fluorine, chlorine, bromine, or iodine atom, for example, fluorine, chlorine, or bromine, for example, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, such as between the rest of the heteroalkyl group and the fragment to which it is attached, as well as attached to the most distal carbon atom in the heteroalkyl group. Examples include —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$NH—OCH$_3$, or —CH$_2$CH$_2$—SS—CH$_3$ As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the terms "patient" and "subject" and "individual" refer interchangeably to a human or a non-human mammal. Non-human mammals include, for example, livestock and pets, such as ovine, bovine, porcine, canine, feline and murine mammals. For example, the patient or subject is human.

As used herein, the term "pharmaceutical composition" refers to a mixture of at least one compound useful in the methods of the invention with a pharmaceutically acceptable carrier. The pharmaceutical composition facilitates administration of the compound to a patient. Multiple techniques of administering a compound exist in the art including, but not limited to, intravenous, intramuscular, oral, aerosol, parenteral, ophthalmic, pulmonary and topical administration.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful in the methods of the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful in the methods of the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful in the methods of the invention, and are physiologically acceptable to the patient. Supplementary active compounds may also be incorporated into the compositions. The "pharmaceutically acceptable carrier" may further include a pharmaceutically acceptable salt of the compound useful in the methods of the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "salts" embraces addition salts of free acids or bases that are useful within the methods of the invention. In certain embodiments, the salts are pharmaceutically acceptable salts. The language "pharmaceutically acceptable salt" refers to a salt of the administered compounds prepared from pharmaceutically acceptable non-toxic acids or bases, including inorganic acids or bases, organic acids or bases, and solvates, hydrates, or clathrates thereof. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxy benzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluene sulfonic, sulfanilic, cyclohexylaminosulfonic, stearic, alginic, O-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "substituted" means that an atom or group of atoms has replaced hydrogen as the substituent attached to another group.

For aryl, aryl-($C_1$-$C_3$ alkyl) and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two. In yet other embodiments, the substituents are independently selected from the group consisting of —$C_1$-$C_6$ alkyl, —OH, —$C_1$-$C_6$ alkoxy, halogen, —$NH_2$, —$N(CH_3)_2$, —C(=O)OH, trifluoromethyl, —C≡N, —C(=O)O($C_1$-$C_4$)alkyl, —C(=O)$NH_2$, —NHC(=O)(aryl or alkyl), —$SO_2NH_2$, —C(=NH)$NH_2$, —$NO_2$, or any combinations thereof. In yet other embodiments, the substituents are independently selected from the group consisting of $C_1$-$C_6$ alkyl, $C_1$-$C_6$ alkoxy, halo, acetamido, and nitro. As used herein, where a substituent is an alkyl or alkoxy group, the carbon chain may be branched, straight or cyclic, with straight being an illustrative example.

As used herein, the term "treatment" or "treating," is defined as the application or administration of a therapeutic compound, i.e., a compound of the invention (alone or in combination with another therapeutic agent), to a patient, or application or administration of a therapeutic compound to an isolated tissue or cell line from a patient (e.g., for diagnosis or ex vivo applications), who has a disease or disorder, a symptom of a disease or disorder, or the potential to develop a disease or disorder, with the purpose to cure, heal, alleviate, relieve, alter, remedy, ameliorate, improve or affect a disease or disorder, the symptoms of a disease or disorder or the potential to develop a disease or disorder. Such treatments may be specifically tailored or modified, based on knowledge obtained from the field of pharmacogenomics.

Non-limiting abbreviations used herein include: AP-V, (DL)-2-amino-5-phosphonovaleric acid; D-PBS, Dulbecco's phosphate-buffered saline; EAAC1, excitatory amino acid carrier 1; EAATs, excitatory amino acid transporters; EAAT1-3, human excitatory amino acid transporter subtypes 1-3; EAAT2, human glutamate transporter 2; GLAST, glutamate and aspartate transporter; GLT-1, rat glutamate transporter 1; HP, hairpin loop; HSB, hybrid structure based; NaOH, sodium hydroxide; PBS-CM, D-PBS with 0.1 mM $CaCl_2$ and 1 mM $MgCl_2$ added; POPC, 1-palmitoyl-2-oleoyl-sn-glycero-3-phosphocholine; SDS, sodium dodecyl sulfate; TFB-TBOA, 3S)-3-[[3-[[4-(Trifluoromethyl)benzoyl]amino]phenyl]methoxy]-L-aspartic acid; TM, transmembrane; UCPH-101, 2-Amino-5,6,7,8-tetrahydro-4-(4-methoxyphenyl)-7-(naphthalen-1-yl)-5-oxo-4H-chromene-3-carbonitrile; WAY 213613, N-[4-(2-Bromo-4,5-difluorophenoxy)phenyl]-L-asparagine; WT, wild type.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to the discovery of small molecule compounds that can be used to activate, stimulate or upregulate the activity of a glutamate transporter. In certain embodiments, the transporter comprises EAAT2. In other embodiments, the compounds of the invention help regulate extracellular glutamate concentrations in a cell or a subject in need thereof. In yet other embodiments, the compounds of the invention increase, induce or upregulate removal (uptake) of glutamate from the neuronal synaptic cleft into neuroglia and neurons. In yet other embodiments, the compounds of the invention inhibit glutamate transport.

In certain embodiments, the compounds of the invention are useful in treating, ameliorating or preventing a disease or disorder that is caused, induced or characterized by abnormal reduction in glutamate transporter activity or abnormal increase in extracellular CNS glutamate concentration in a subject. In other embodiments, the disease or disorder is selected from the group consisting of ischemia, seizure, traumatic brain injury, stroke, epilepsy, schizophrenia, and neurodegenerative diseases or disorders (such as, but not limited to, Parkinson's disease, Alzheimer's disease, Huntington's disease, amyotrophic lateral sclerosis (ALS), ALS-parkinsonism dementia complex, and HIV-associated neurocognitive disorder (HAND).

As described herein, direct and selective glutamate transport enhancers have not been identified apart from the compound Parawixin-1, which is found in the *P. bistriata* spider venom. Studies of the interaction of Parawixin-1 with glutamate transporters allowed for identification of EAAT2 regions that are essential for transport activation. In certain embodiments, model studies using EAAT2 allowed for the identification of neuroprotective compounds that function by enhancing the removal of excessive glutamate in the synaptic cleft, and preventing increased glutamate levels and excitotoxicity.

As described herein, a glutamate transporter crystal structure and subsequent systematic mutagenesis studies allowed for the identification of a binding pocket on EAAT2 that may be modulated allosterically to enhance glutamate uptake. Virtual screening efforts allowed for the identification of novel compounds that modulate glutamate transporter activity. The hybrid structure based approach described herein involves the creation of a high resolution pharmacophore based on knowledge of the protein structure from crystallography, as well as insights derived from targeted mutations of the protein, to obtain detailed information about the specific binding pocket. This high resolution pharmacophore may be used to perform a virtual screen on commercially available compound structures to obtain high quality hits. Prioritized hit structures are then individually docked into the virtual binding pocket to identify the best structures for purchase or synthesis for in vitro testing. In certain embodiments, the compounds may be tested in cultured cells and synaptosomes to confirm that they increase glutamate uptake. In other embodiments, the compounds may be tested for neuroprotective properties in in vitro models of glutamate excitotoxicity.

Compounds

The compounds useful in the methods of the invention can be synthesized using techniques well-known in the art of organic synthesis.

In one aspect, the compound is the compound of formula (I), or an enantiomer, diastereoisomer, salt or solvate thereof:

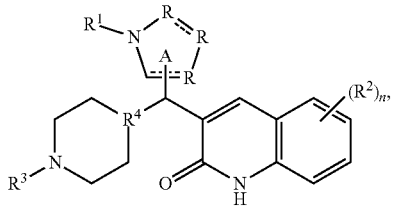
(I)

wherein in (I), each ≡≡≡ bond in ring A is independently a double or a single covalent bond, wherein:

(a) when a ≡≡≡ bond is a double covalent bond, each R group substituted at the bond is independently selected from the group consisting of N, CH and $C(C_1-C_6$ alkyl), wherein the alkyl group is optionally substituted; and (b) when a ≡≡≡ bond is a single covalent bond, each R group substituted at the bond is independently selected from the group consisting of NH, $N(C_1-C_6$ alkyl), S, O, $CH_2$, $CH(C_1-C_6$ alkyl) and $C(C_1-C_6$ alkyl)$_2$, wherein the alkyl group is optionally substituted;

$R^1$ is selected from the group consisting of —$C_1-C_6$ alkyl, —$C_1-C_6$ heteroalkyl, —($C_0-C_3$ alkyl)-($C_3-C_6$ cycloalkyl), —($C_0-C_3$ alkyl)-($C_4-C_{10}$ heterocyclyl), —($C_0-C_3$ alkyl)-($C_6-C_{10}$ aryl) and —($C_0-C_3$ alkyl)-($C_5-C_{10}$ heteroaryl), wherein the alkyl, heteroalkyl, cycloalkyl, heterocyclyl, aryl and heteroaryl groups are independently optionally substituted;

each occurrence of $R^2$ is independently selected from the group consisting of H, —$C_1-C_6$ alkyl, —OH, —$C_1-C_6$ alkoxy, halogen, —$NH_2$, —$N(CH_3)_2$, —C(═O)OH, trifluoromethyl, —C(═O)O($C_1-C_4$)alkyl, —C(═O)$NH_2$, —$SO_2NH_2$, —C(═NH)$NH_2$, and —$NO_2$;

n is an integer ranging from 0 to 4;

$R^3$ is selected from the group consisting of —(C═O)$_{0-1}$ ($C_1-C_6$ alkyl), —(C═O)$_{0-1}$($C_1-C_6$ heteroalkyl), —(C═O)$_{0-1}$($C_0-C_3$alkyl)-($C_3-C_6$ cycloalkyl), —(C═O)$_{0-1}$($C_0-C_3$alkyl)-($C_4-C_{10}$ heterocyclyl), —(C═O)$_{0-1}$($C_0-C_3$alkyl)-($C_6-C_{10}$ aryl), —(C═O)$_{0-1}$ ($C_0-C_3$alkyl)-($C_5-C_{10}$ heteroaryl), —($SO_2$)$_{0-1}$($C_1-C_6$ alkyl), —($SO_2$)$_{0-1}$($C_1-C_6$ heteroalkyl), —($SO_2$)$_{0-1}$($C_0$-$C_3$ alkyl)-($C_3-C_6$ cycloalkyl), —($SO_2$)$_{0-1}$($C_0-C_3$alkyl)-($C_4-C_{10}$ heterocyclyl), $SO_2$)$_{0-1}$($C_0-C_3$ alkyl)-($C_6-C_{10}$ aryl) and —($SO_2$)$_{0-1}$($C_0-C_3$alkyl)-($C_5-C_{10}$ heteroaryl), wherein the alkyl, heteroalkyl, cycloalkyl, heterocyclyl, aryl and heteroaryl groups are independently optionally substituted; and $R^4$ is N or CH.

In certain embodiments, compound (I), or any racemate, enantiomer, or diastereoisomer thereof, is selected from the group consisting of:

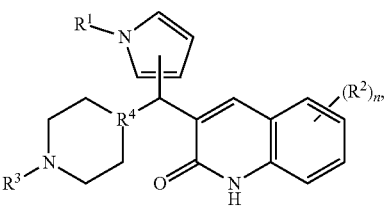
(Ia)

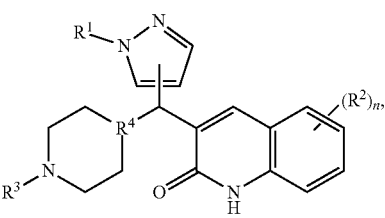
(Ib)

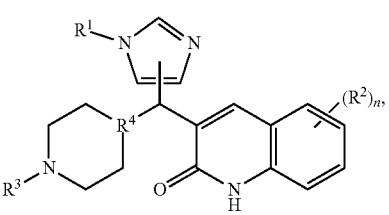
(Ic)

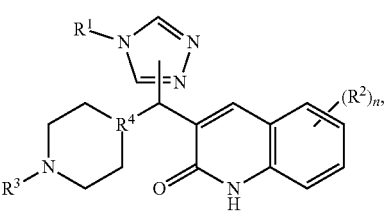
(Id)

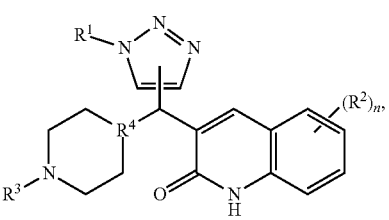
(Ie)

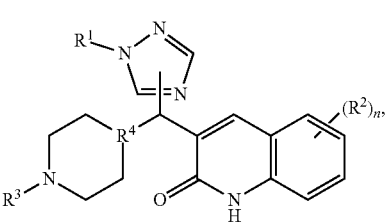
(If)

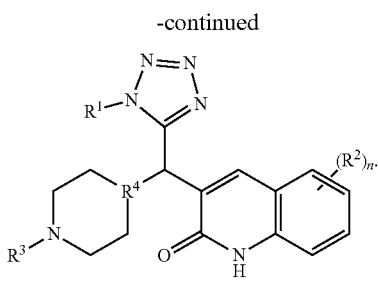
(Ig)

In certain embodiments, in (I) $R^1$ is selected from the group consisting of —($C_1$-$C_3$ alkyl)-($C_3$-$C_6$ cycloalkyl), —($C_1$-$C_3$ alkyl)-($C_4$-$C_{10}$ heterocyclyl), —($C_1$-$C_3$ alkyl)-($C_6$-$C_{10}$ aryl) and —($C_1$-$C_3$ alkyl)-($C_5$-$C_{10}$ heteroaryl), wherein the alkyl, cycloalkyl, heterocyclyl, aryl and heteroaryl groups are independently optionally substituted.

In certain embodiments, in (I) $R^1$ is selected from the group consisting of —($C_1$-$C_3$ alkyl)-($C_6$-$C_{10}$ aryl) and —($C_1$-$C_3$ alkyl)-($C_5$-$C_{10}$ heteroaryl), wherein the alkyl, aryl and heteroaryl groups are independently optionally substituted.

In certain embodiments, in (I) each occurrence of $R^2$ is independently selected from the group consisting of H, —$C_1$-$C_6$ alkyl, —OH, —$C_1$-$C_6$ alkoxy, halogen, —$NH_2$, —$N(CH_3)_2$, —C(=O)OH, trifluoromethyl, —C≡N and —$NO_2$.

In certain embodiments, in (I) n is 2 or 3.

In certain embodiments, in (I) $R^3$ is selected from the group consisting of —($C_1$-$C_6$ alkyl), —($C_1$-$C_6$ heteroalkyl), —($C_0$-$C_3$ alkyl)-($C_3$-$C_6$ cycloalkyl), —($C_0$-$C_3$ alkyl)-($C_4$-$C_{10}$ heterocyclyl), —($C_0$-$C_3$ alkyl)-($C_6$-$C_{10}$ aryl), —($C_0$-$C_3$ alkyl)-($C_5$-$C_{10}$ heteroaryl), —(C=O)($C_0$-$C_3$ alkyl)-($C_6$-$C_{10}$ aryl), and —(C=O)($C_0$-$C_3$ alkyl)-($C_5$-$C_{10}$ heteroaryl), wherein the alkyl, heteroalkyl, cycloalkyl, heterocyclyl, aryl and heteroaryl groups are independently optionally substituted.

In certain embodiments, compound (I) is

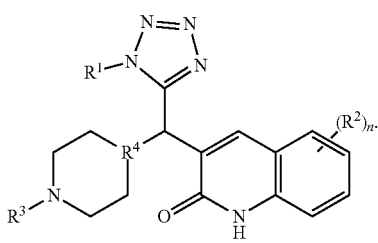
(Ig)

In certain embodiments, compound (I) is

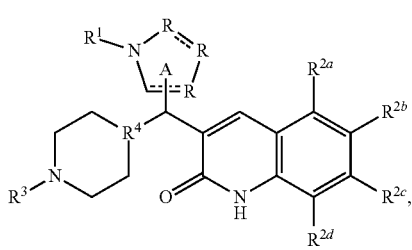
(Ih)

wherein: $R^{2a}$, $R^{2c}$, and $R^{2d}$ are independently selected from the group consisting of H and $C_1$-$C_6$ alkyl, and $R^{2b}$ is OH or $C_1$-$C_6$ alkoxy.

In certain embodiments, $R^{2a}$, $R^{2c}$, and $R^{2d}$ are each H. In other embodiments, $R^{2b}$ is hydroxyl, methoxy, ethoxy, propoxy, or isopropoxy.

In certain embodiments, compound (I) is

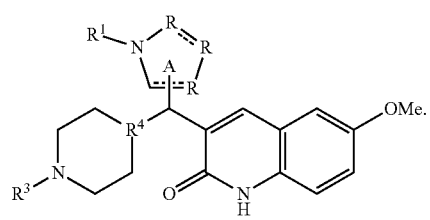
(Ii)

In certain embodiments, compound (I) is

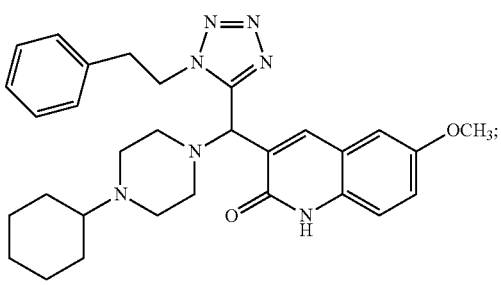 [SMILES: COc1ccc2[nH]c(=O)c(C(c3nnnn3CCc3ccccc3)N3CCN(C4CCCCC4)CC3)cc2c1]
(Ij)

In certain embodiments, in (I) $R^3$ is optionally substituted cyclohexyl or phenyl.

In certain embodiments, the compound of the invention is selected from the group consisting of:

3-((4-cyclohexylpiperazin-1-yl)(1-phenethyl-1H-tetrazol-5-yl)methyl)-6-methoxy-quinolin-2(1H)-one (GT949)

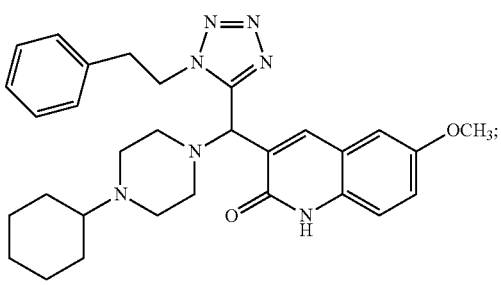 [SMILES: COc1ccc2[nH]c(=O)c(C(c3nnnn3CCc3ccccc3)N3CCN(C4CCCCC4)CC3)cc2c1]

6-methoxy-3-((1-phenethyl-1H-tetrazol-5-yl)(4-(3-(trifluoromethyl)phenyl)piperazin-1-yl)methyl)quinolin-2(1H)-one (GT951)

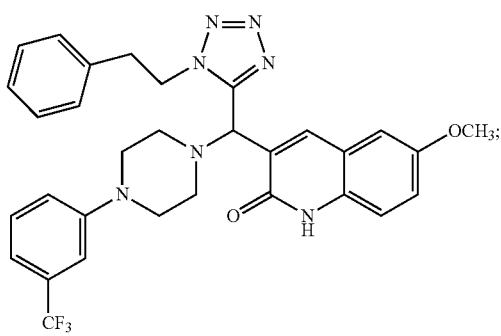 [SMILES: COc1ccc2[nH]c(=O)c(C(c3nnnn3CCc3ccccc3)N3CCN(c4cccc(C(F)(F)F)c4)CC3)cc2c1]

3-((4-(benzo[d][1,3]dioxol-5-ylmethyl)piperazin-1-yl)(1-phenethyl-1H-tetrazol-5-yl)methyl)-6,7-dimethylquinolin-2(1H)-one (GT835)

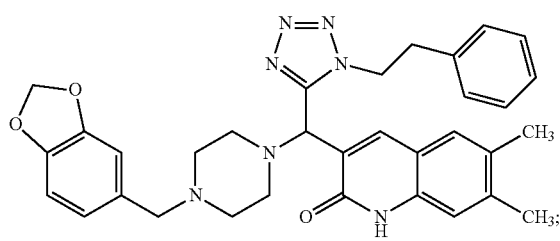 [SMILES: Cc1cc2cc(C(c3nnnn3CCc3ccccc3)N3CCN(Cc4ccc5c(c4)OCO5)CC3)c(=O)[nH]c2cc1C]

3-((4-(furan-2-carbonyl)piperazin-1-yl)(1-phenethyl-1H-tetrazol-5-yl)methyl)-6,8-dimethylquinolin-2(1H)-one (GT729)

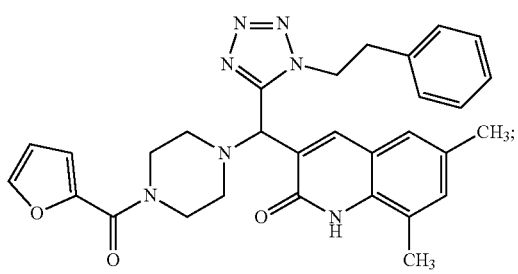 [SMILES: Cc1cc(C)c2[nH]c(=O)c(C(c3nnnn3CCc3ccccc3)N3CCN(C(=O)c4ccco4)CC3)cc2c1]

3-((4-(furan-2-carbonyl)piperazin-1-yl)(1-phenethyl-1H-tetrazol-5-yl)methyl)-5,7-dimethylquinolin-2(1H)-one (GT996)

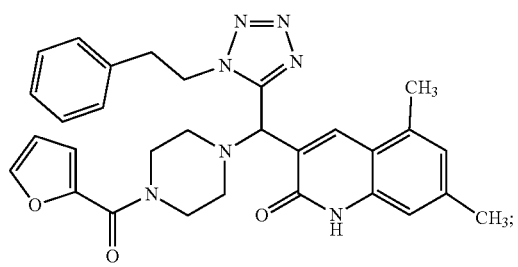 [SMILES: Cc1cc(C)c2cc(C(c3nnnn3CCc3ccccc3)N3CCN(C(=O)c4ccco4)CC3)c(=O)[nH]c2c1]

3-((4-(benzo[d][1,3]dioxol-5-ylmethyl)piperazin-1-yl)(1-phenethyl-1H-tetrazol-5-yl) methyl)-5,8-dimethylquinolin-2(1H)-one (GT867)

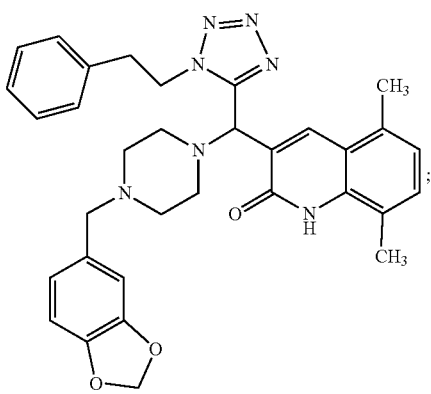

an enantiomer, diastereoisomer, salt or solvate thereof, and any mixtures thereof.

In one aspect, the compound is the compound of formula (II) or salt or solvate thereof:

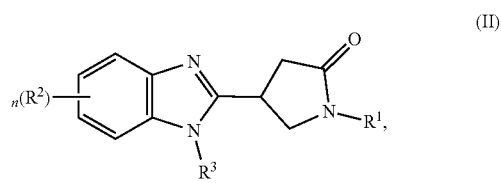

(II)

wherein in (II):

$R^1$ is selected from the group consisting of —$C_1$-$C_6$ alkyl, —$C_2$-$C_6$ alkenyl, —$C_2$-$C_6$ alkynyl, —$C_1$-$C_6$ heteroalkyl, —$C_1$-$C_6$ heteroalkenyl and —$C_1$-$C_6$ heteroalkynyl, wherein the alkyl, alkenyl, alkynyl, heteroalkyl, heteroalkenyl and heteroalkynyl are independently optionally substituted;

each occurrence of $R^2$ is independently selected from the group consisting of H, —$C_1$-$C_6$ alkyl, —OH, —$C_1$-$C_6$ alkoxy, halogen, —$NH_2$, —$N(CH_3)_2$, —C(=O)OH, trifluoromethyl, —C(=O)O($C_1$-$C_4$)alkyl, —C(=O)$NH_2$, —$SO_2NH_2$, —C(=NH)$NH_2$, and —$NO_2$;

n is an integer ranging from 0 to 4;

$R^3$ is selected from the group consisting of —($C_1$-$C_6$ alkyl)-$O_x$—($C_3$-$C_6$ cycloalkyl), —($C_1$-$C_6$ alkyl)-$O_x$—($C_4$-$C_{10}$ heterocyclyl), —($C_1$-$C_6$ alkyl)-$O_x$—($C_6$-$C_{10}$ aryl) and —($C_1$-$C_6$alkyl)-$O_x$—($C_5$-$C_{10}$ heteroaryl), wherein the alkyl, cycloalkyl, heterocyclyl, aryl and heteroaryl groups are independently optionally substituted; and x is 0 or 1.

In certain embodiments, in (II) n is 0.

In certain embodiments, in (II) x is 1. In other embodiments, in (II) x is 0.

In certain embodiments, in (II) $R^1$ is selected from the group consisting of —$C_2$-$C_6$ alkenyl and —$C_2$-$C_6$ alkynyl, wherein the alkenyl and alkynyl are independently optionally substituted.

In certain embodiments, in (II) $R^3$ is selected from the group consisting of —($C_1$-$C_6$ alkyl)-$O_x$—($C_6$-$C_{10}$ aryl) and —($C_1$-$C_6$alkyl)-$O_x$—($C_5$-$C_{10}$ heteroaryl), wherein the alkyl, aryl and heteroaryl groups are independently optionally substituted.

In certain embodiments, the compound of the invention is selected from the group consisting of:

1-allyl-4-(1-(4-(4-chloro-3-methylphenoxy)butyl)-1H-benzo[d]imidazol-2-yl)pyrrolidin-2-one (GT939)

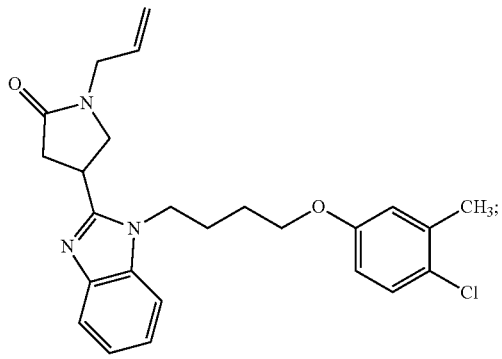 [SMILES: C=CCN1CC(c2nc3ccccc3n2CCCCOc2ccc(Cl)c(C)c2)CC1=O]

1-allyl-4-(1-(4-(3,4-dimethylphenoxy)butyl)-1H-benzo[d]imidazol-2-yl)pyrrolidin-2-one (GT938)

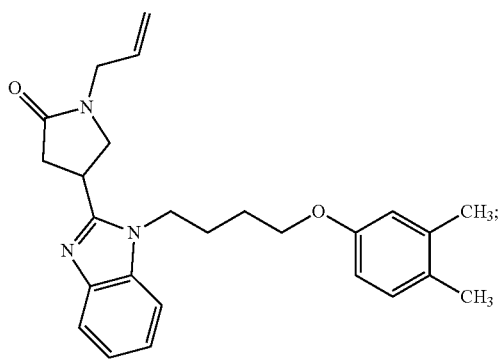 [SMILES: C=CCN1CC(c2nc3ccccc3n2CCCCOc2ccc(C)c(C)c2)CC1=O]

1-allyl-4-(1-(3-(4-(sec-butyl)phenoxy)propyl)-1H-benzo[d]imidazol-2-yl)pyrrolidin-2-one (GT922)

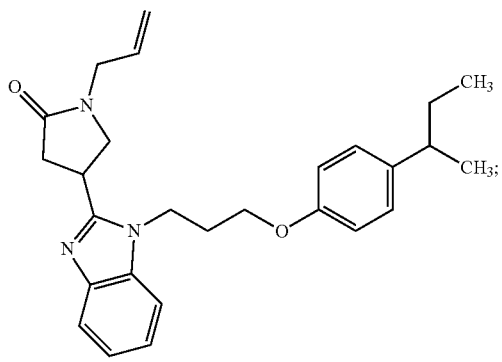 [SMILES: C=CCN1CC(c2nc3ccccc3n2CCCOc2ccc(C(C)CC)cc2)CC1=O]

an enantiomer, diastereoisomer, salt or solvate thereof, and any mixtures thereof.

In one aspect, the compound is the compound of formula (III) or salt or solvate thereof:

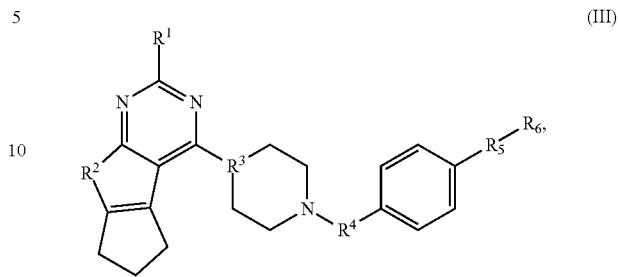

(III)

wherein in (III):
R$^1$ is selected from the group consisting of —(C$_0$-C$_3$ alkyl)-(C$_6$-C$_{10}$ aryl) and —(C$_0$-C$_3$ alkyl)-(C$_5$-C$_{10}$ heteroaryl), wherein the alkyl, aryl and heteroaryl groups are independently optionally substituted;
R$^2$ is NH, NR$^6$, S or O;
R$^3$ is N or CH;
R$^4$ is —C(=O)— or —S(=O)$_2$—;
R$^5$ is —C(=O)— or —S(=O)$_2$—; and,
R$^6$ is selected from the group consisting of —C$_1$-C$_6$ alkyl, —C$_1$-C$_6$ heteroalkyl, —(C$_0$-C$_3$ alkyl)-(C$_3$-C$_6$ cycloalkyl), —(C$_0$-C$_3$ alkyl)-(C$_4$-C$_{10}$ heterocyclyl), —(C$_0$-C$_3$ alkyl)-(C$_6$-C$_{10}$ aryl) and —(C$_0$-C$_3$ alkyl)-(C$_5$-C$_{10}$ heteroaryl), wherein the alkyl, heteroalkyl, cycloalkyl, heterocyclyl, aryl and heteroaryl groups are independently optionally substituted.

In certain embodiments, in (III) R$^1$— is —C$_6$-C$_{10}$ aryl or —C$_5$-C$_{10}$ heteroaryl, wherein the aryl and heteroaryl groups are independently optionally substituted. In certain embodiments, in (III) R$^2$ is S. In certain embodiments, in (III) R$^3$ is N. In certain embodiments, in (III) R$^4$ is —C(=O)—. In certain embodiments, in (III) R$^5$ is —S(=O)$_2$—. In certain embodiments, in (III) R$^6$ is —C$_1$-C$_6$ heteroalkyl or —C$_4$-C$_{10}$ heterocyclyl, wherein the heteroalkyl and heterocyclyl groups are independently optionally substituted.

In certain embodiments, the compound is (4-(2-phenyl-6,7-dihydro-5H-cyclopenta[4,5]thieno[2,3-d]pyrimidin-4-yl)piperazin-1-yl)(4-(pyrrolidin-1-ylsulfonyl)phenyl)methanone (GT988), or a salt or solvate thereof:

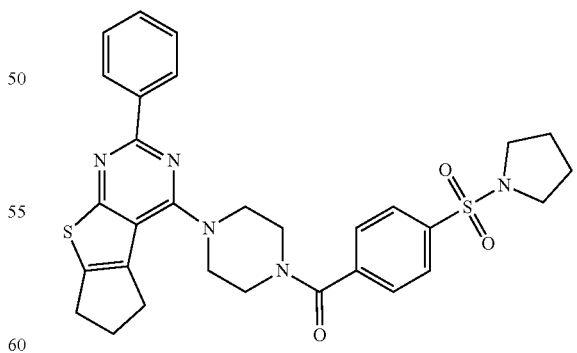

In certain embodiments, the compound is not 3-((4-(furan-2-carbonyl)piperazin-1-yl)(1-phenethyl-1H-tetrazol-5-yl)methyl)-6,8-dimethylquinolin-2(1H)-one. In certain embodiments, the compound is not 3-((4-(benzo[d][1,3]dioxol-5-ylmethyl)piperazin-1-yl)(1-phenethyl-1H-tetrazol-5-yl)methyl)-6,7-dimethylquinolin-2(1H)-one. In certain embodiments, the compound is not 3-((4-(benzo[d][1,3]dioxol-5-ylmethyl)piperazin-1-yl)(1-phenethyl-1H-tetrazol-5-yl)methyl)-5,8-dimethylquinolin-2(1H)-one. In certain embodiments, the compound is not 1-allyl-4-(1-(3-(4-(sec-butyl)phenoxy)propyl)-1H-benzo[d]imidazol-2-yl)pyrrolidin-2-one. In certain embodiments, the compound is not 1-allyl-4-(1-(4-(3,4-dimethylphenoxy)butyl)-1H-benzo[d]imidazol-2-yl)pyrrolidin-2-one. In certain embodiments, the compound is not 1-allyl-4-(1-(4-(4-chloro-3-methylphenoxy)butyl)-1H-benzo[d]imidazol-2-yl)pyrrolidin-2-one. In certain embodiments, the compound is not 3-((4-cyclohexylpiperazin-1-yl)(1-phenethyl-1H-tetrazol-5-yl)methyl)-6-methoxy-quinolin-2(1H)-one. In certain embodiments, the compound is not 6-methoxy-3-((1-phenethyl-1H-tetrazol-5-yl)(4-(3-(trifluoromethyl)phenyl)piperazin-1-yl)methyl)quinolin-2(1H)-one. In certain embodiments, the compound is not (4-(2-phenyl-6,7-dihydro-5H-cyclopenta[4,5]thieno[2,3-d]pyrimidin-4-yl)piperazin-1-yl)(4-(pyrrolidin-1-ylsulfonyl)phenyl)methanone. In certain embodiments, the compound is not 3-((4-(furan-2-carbonyl)piperazin-1-yl)(1-phenethyl-1H-tetrazol-5-yl)methyl)-5,7-dimethylquinolin-2(1H)-one.

In certain embodiments, the substituted alkyl, cycloalkyl (such as, for example, cyclopropyl, cyclobutyl, cyclopentyl, or cyclohexyl), alkenyl, alkynyl, heteroalkyl, heteroalkenyl, heteroalkynyl, or heterocyclyl is independently substituted with at least selected from the group consisting of $C_1$-$C_6$ alkyl, —OH, $C_1$-$C_6$ alkoxy, halogen, $NH_2$, $NH(CH_3)$, $N(CH_3)_2$, —C(=O)OH, trifluoromethyl, —C(=O)O($C_1$-$C_4$)alkyl, —C(=O)$NH_2$, —NHC(=O)(aryl or alkyl), —$SO_2NH_2$, —C(=NH)$NH_2$, —$NO_2$, or any combinations thereof.

In certain embodiments, the substituted phenyl or heteroaryl is independently substituted with at least selected from the group consisting of $C_1$-$C_6$ alkyl, —OH, $C_1$-$C_6$ alkoxy, halogen, $NH_2$, $NH(CH_3)$, $N(CH_3)_2$, —C(=O)OH, trifluoromethyl, —C(=O)O($C_1$-$C_4$)alkyl, —C(=O)$NH_2$, —NHC(=O)(aryl or alkyl), —$SO_2NH_2$, —C(=NH)$NH_2$, —$NO_2$, or any combinations thereof.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention exist as tautomers. All tautomers are included within the scope of the compounds recited herein.

In certain embodiments, compounds described herein are prepared as prodrugs. A "prodrug" is an agent converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}F$, and $^{35}S$.

In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The invention includes a pharmaceutical composition comprising at least one pharmaceutically acceptable carrier and at least one compound of the invention. In certain embodiments, the composition further comprises at least one additional therapeutic agent.

Methods

The invention includes a method of treating, ameliorating or preventing a disease or disorder that is caused, induced or characterized by abnormal reduction in glutamate transporter activity or abnormal increase in extracellular CNS glutamate concentration in a subject. The method comprises administering to the subject a therapeutically effective amount of at least one compound of the invention, or an enantiomer, diastereoisomer, salt or solvate thereof. In certain embodiments, the disease or disorder is selected from the group consisting of ischemia, seizure, traumatic brain injury, stroke, epilepsy, schizophrenia, and neurodegenerative diseases or disorders (such as, but not limited to, Parkinson's disease, Alzheimer's disease, Huntington's disease, amyotrophic lateral sclerosis (ALS), and ALS-parkinsonism dementia complex, and HIV-associated neurocognitive disorder (HAND).

In certain embodiments, the compound of the invention is selected from the group consisting of: 3-((4-(furan-2-carbonyl)piperazin-1-yl)(1-phenethyl-1H-tetrazol-5-yl)methyl)-6,8-dimethylquinolin-2(1H)-one; 3-((4-(benzo[d][1,3]dioxol-5-ylmethyl)piperazin-1-yl)(1-phenethyl-1H-tetrazol-5-yl)methyl)-6,7-dimethylquinolin-2(1H)-one; 3-((4-(benzo[d][1,3]dioxol-5-ylmethyl)piperazin-1-yl)(1-phenethyl-1H-tetrazol-5-yl)methyl)-5,8-dimethylquinolin-2(1H)-one; 1-allyl-4-(1-(3-(4-(sec-butyl)phenoxy)propyl)-1H-benzo[d]imidazol-2-yl)pyrrolidin-2-one; 1-allyl-4-(1-(4-(3,4-dimethylphenoxy)butyl)-1H-benzo[d]imidazol-2-yl)pyrrolidin-2-one; 1-allyl-4-(1-(4-(4-chloro-3-methylphenoxy)butyl)-1H-benzo[d]imidazol-2-yl)pyrrolidin-2-one; 3-((4-cyclohexylpiperazin-1-yl)(1-phenethyl-1H-tetrazol-5-yl)methyl)-6-methoxy-quinolin-2(1H)-one; 6-methoxy-3-((l-phenethyl-1H-tetrazol-5-yl)(4-(3-(trifluoromethyl)phenyl)piperazin-1-yl)methyl)quinolin-2(1H)-one; (4-(2-phenyl-6,7-dihydro-5H-cyclopenta[4,5]thieno[2,3-d]pyrimidin-4-yl)piperazin-1-yl)(4-(pyrrolidin-1-ylsulfonyl)phenyl)methanone; 3-((4-(furan-2-carbonyl)piperazin-1-yl)(1-phenethyl-1H-tetrazol-5-yl)methyl)-5,7-dimethylquinolin-2(1H)-one, an enantiomer, diastereoisomer, salt or solvate thereof, and any mixtures thereof.

In certain embodiments, the compound is selected from the group consisting of: 1-allyl-4-(1-(4-(4-chloro-3-methylphenoxy)butyl)-1H-benzo[d]imidazol-2-yl)pyrrolidin-2-one; 3-((4-cyclohexylpiperazin-1-yl)(1-phenethyl-1H-tetrazol-5-yl)methyl)-6-methoxy-quinolin-2(1H)-one; 6-methoxy-3-((l-phenethyl-1H-tetrazol-5-yl)(4-(3-(trifluoromethyl) phenyl)piperazin-1-yl)methyl)quinolin-2(1H)-one; an enantiomer, diastereoisomer, salt or solvate thereof, and any mixtures thereof.

In certain embodiments, the compound is (+)-3-((4-cyclohexylpiperazin-1-yl)(1-phenethyl-1H-tetrazol-5-yl)methyl)-6-methoxy-quinolin-2(1H)-one, or a salt or solvate thereof. In certain embodiments, the compound is (−)-3-((4-cyclohexylpiperazin-1-yl)(1-phenethyl-1H-tetrazol-5-yl)methyl)-6-methoxy-quinolin-2(1H)-one, or a salt or solvate thereof. In certain embodiments, the compound is (+)-6-methoxy-3-((1-phenethyl-1H-tetrazol-5-yl)(4-(3-(trifluoromethyl)phenyl)piperazin-1-yl)methyl)quinolin-2(1H)-one, or a salt or solvate thereof. In certain embodiments, the compound is (−)-6-methoxy-3-((1-phenethyl-1H-tetrazol-5-yl)(4-(3-(trifluoromethyl)phenyl)piperazin-1-yl)methyl)quinolin-2(1H)-one, or a salt or solvate thereof.

In certain embodiments, the compound is administered to the subject as part of a pharmaceutical composition. In other embodiments, the subject is further administered at least one additional therapeutic agent. In yet other embodiments, the compound and the at least one additional therapeutic agent are co-administered to the subject. In yet other embodiments, the compound and the at least one additional therapeutic agent are co-formulated. In yet other embodiments, the compound is administered to the subject a given period of time before or after the at least one additional therapeutic agent is administered to the subject. In yet other embodiments, the subject is a mammal. In yet other embodiments, the mammal is human.

Combination Therapies

In one non-limiting embodiment, the compounds of the present invention are useful in the methods of present invention in combination with one or more additional compounds useful for treating a disease or disorder contemplated within the invention, or a complication or symptom thereof. These additional compounds may comprise compounds of the present invention or other compounds, e.g., commercially available compounds, known to treat, prevent, or reduce the symptoms of a disease or disorder contemplated within the invention.

In non-limiting examples, the additional compounds comprise riluzole (6-(trifluoromethoxy)benzothiazol-2-amine) or ceftriaxone ((6R,7R)-7-{[(2Z)-2-(2-amino-1,3-thiazol-4-yl)→2-(methoxy imino)acetyl]amino}-3-{[(2-methyl-5,6-dioxo-1,2,5,6-tetrahydro-1,2,4-triazin-3-yl)thio]methyl}-8-oxo-5-thia-1-azabicyclo[4.2.0]oct-2-ene-2-carboxylic acid).

A synergistic effect may be calculated, for example, using suitable methods such as, for example, the Sigmoid-Eurax equation (Holford & Scheiner, 1981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of the disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, for example a mammal, for example a human, may be carried out using known procedures, at dosages and for periods of time effective to treat the disease or disorder in the patient. An effective amount of the therapeutic compound necessary to achieve a therapeutic effect may vary according to factors such as the state of the disease or disorder in the patient; the age, sex, and weight of the patient; and the ability of the therapeutic compound to treat the disease or disorder in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from individual to individual depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the disease or disorder, or a complication or symptom thereof) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of the disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include nasal, inhalational, topical, oral, buccal, rectal, pleural, peritoneal, vaginal, intramuscular, subcutaneous, transdermal, epidural, intratracheal, otic, intraocular, intrathecal and intravenous. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

The present invention also includes a multi-layer tablet comprising a layer providing for the delayed release of one or more compounds of the invention, and a further layer providing for the immediate release of a medication for treatment of the disease or disorder. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation. In a specific embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention will depend on the age, sex and weight of the patient, the current medical condition of the patient and the progression of the disease or disorder in the patient being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials

Radiolabeled substrates, [$^3$H]-glutamic acid (51.1 Ci/mmol), [$^3$H]-dopamine (53.6 Ci/mmol), [$^3$H]-serotonin (28.2 Ci/mmol), and [$^3$H]-norepinephrine (14.9 Ci/mmol), were purchased from PerkinElmer (Boston, MA, USA). DL-TBOA was purchased from Tocris (Bristol, UK). Cell culture media and supplements, including Dulbecco's modified Eagle's medium (DMEM) with glucose, Neurobasal-A, fetal bovine serum, fetal calf serum, heat-inactivated horse serum, penicillin/streptomycin, glutamine, L-glutamax, Dulbecco's phosphate-buffered saline (D-PBS), L-glutamax-1, B-27 supplement, and scintillation fluid, were obtained from Thermo Fisher Scientific (Waltham, MA). Transfection reagent TransIT-LT1 was from Mirus Bio LLC (Madison, WI). Reagents for uptake assays and nonradiolabeled substrates were purchased from Sigma-Aldrich (St. Louis, MO).

Modeling the Outward-Facing Three-Dimensional Structure of EAAT2:

Using a glutamate transporter homologue from *Pyrococcus horikoshii* Glt(ph), EAAT2 is modeled in a substrate and an inhibitor bound state (pdb codes 2NWL and 2NWW), using the homology modeling program Modeller (ver 9.1). Interactions of compounds with these two conformations are explored. Without wishing to be limited by any theory, these are the two most likely conformations to which a transporter activator binds.

According to an optimized protocol, ten structures of EAAT2 are modeled and one low-energy structure is subjected to further refinement by energy minimization and constrained MD simulation. The resulting structure is further modeled within a membrane environment (POPC membrane patch) using the Desmond program (D.E. Shaw Research, NY) with a production run of 30 ns. Optimal positioning of the membrane is computed using the Glt(ph) structures in orientations of proteins in the membrane database and in the PPM server. The results are analyzed using trajectory analysis with the VMD program. An average 3D structure (FIGS. 19A-19B) was generated using the last 5 ns of the production run, which was utilized for in silico screening.

Hybrid Structure-Based (HSB) Virtual Screening:

The HSB method was employed for designing and screening small molecules that could bind to the EAAT2 modeled structure. The allosteric pocket to be targeted was derived from analyzing the molecular dynamics simulation trajectories and site-directed mutagenesis studies that included H71 [TM2], L290, L295, G298 [TM5], and W472 [TM8] of EAAT2.

A five-point three-dimensional receptor-based pharmacophore (FIG. 19B) was designed using residues M86, D485, W472, K299, and L295. The receptor-based pharmacophore is central to the hybrid structure-based method, wherein the pharmacophore is designed using the residues lining the allosteric site of EAAT2 and is assigned chemical features based on the nature of the residues. The receptor-based pharmacophore comprises pharmacophore elements, namely, aromatic ring, hydrophobic groups, and hydrogen bond donor and acceptor groups assigned to residues W472, L295, M86, D485, and K299, respectively. The resulting pharmacophore was used to perform a virtual screen on a database of 3 million small molecules to obtain high-quality hits.

The screening was performed using legacy Sybyl 8.1 program with Unity module (Tripos Inc.). The hit molecules that resulted from the screening were subjected to a variety of filtering schemes, including drug-like properties using the Lipinski's rule, cardiotoxicity, blood-brain barrier penetration, and activation of a xenobiotic receptor (PXR) that could lead to drug-drug interactions.

In Silico Docking of Compounds to the Allosteric Site:

Fifty eight hit molecules that passed the filtering criteria were docked to the allosteric site using the docking program GOLD (ver 5.2). To efficiently sample the conformational flexibility of the ligand and the allosteric site residues, 20 independent runs were performed and resulting protein-ligand complexes were ranked using customized scoring schemes. The protein-ligand complexes were scored using a two-tiered scoring scheme. The first level of scoring and ranking the complexes was performed using the default Goldscore method available from the Gold docking program.

On the basis of the Goldscore ranking, the 25 best ranking protein-ligand complexes (with 25 different small molecules) were chosen for customized scoring. The customized scoring scheme is a knowledge-based method that is constructed by differentially weighting the positive interactions and penalizing the negative interactions. In this case study, the nature of interactions with the pharmacophore elements and residues within 4 Å from the center of the pharmacophore were utilized to determine the positive and negative interactions. Aromatic stacking interactions (such as the arene-arene interactions between GT949's triazole ring and the indole ring of W472), hydrogen bonded interactions (such as between the piperazine of GT949 and T192), or hydrophobic interactions with hydrophobic residues were treated as positive interactions, and those that had conflicting properties were considered negative interactions.

Figure 5A:
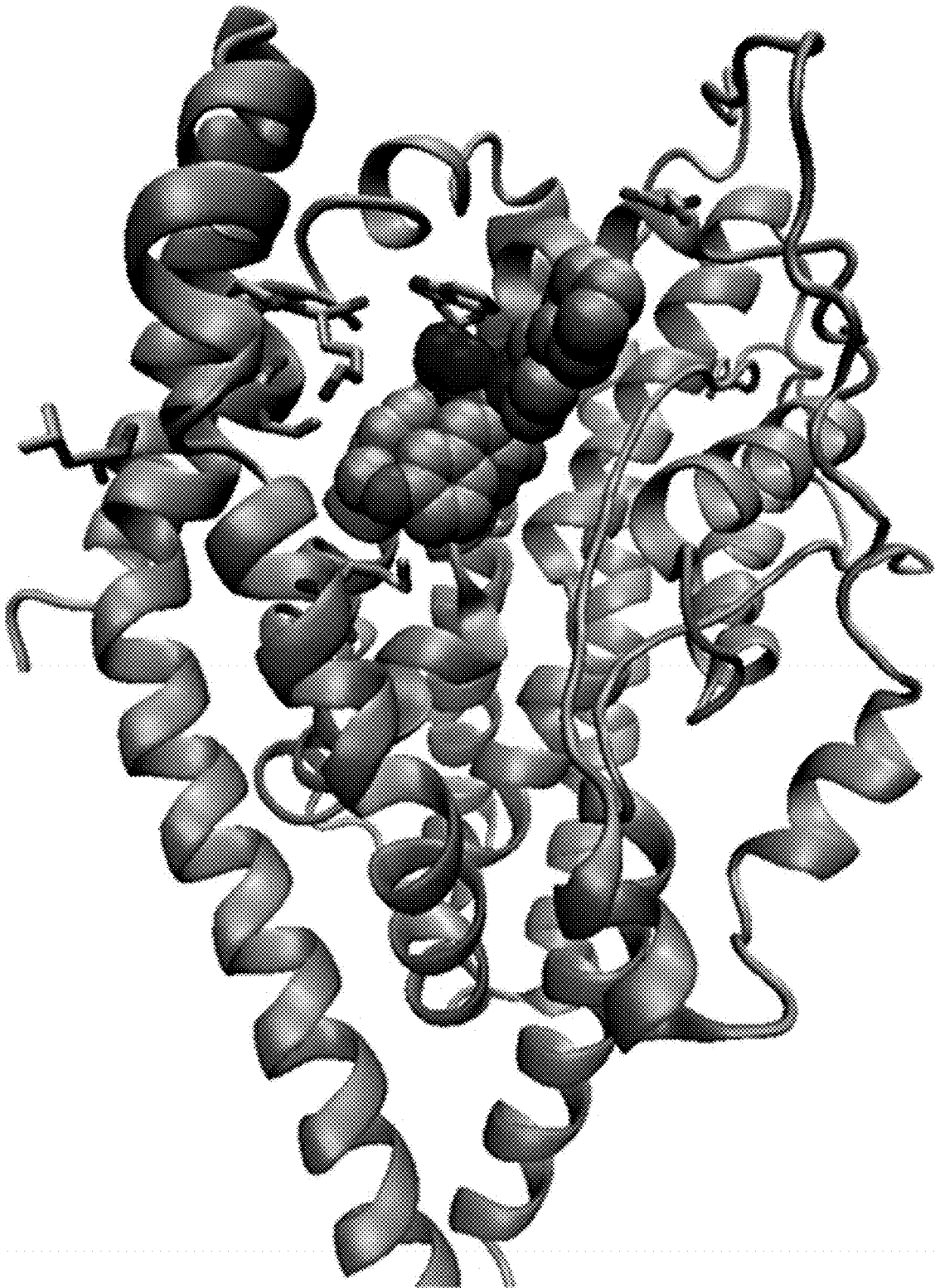
FIGS. 5A-5C illustrate molecular docking of GT949 and GT951 at the binding site.
Figure 5B:
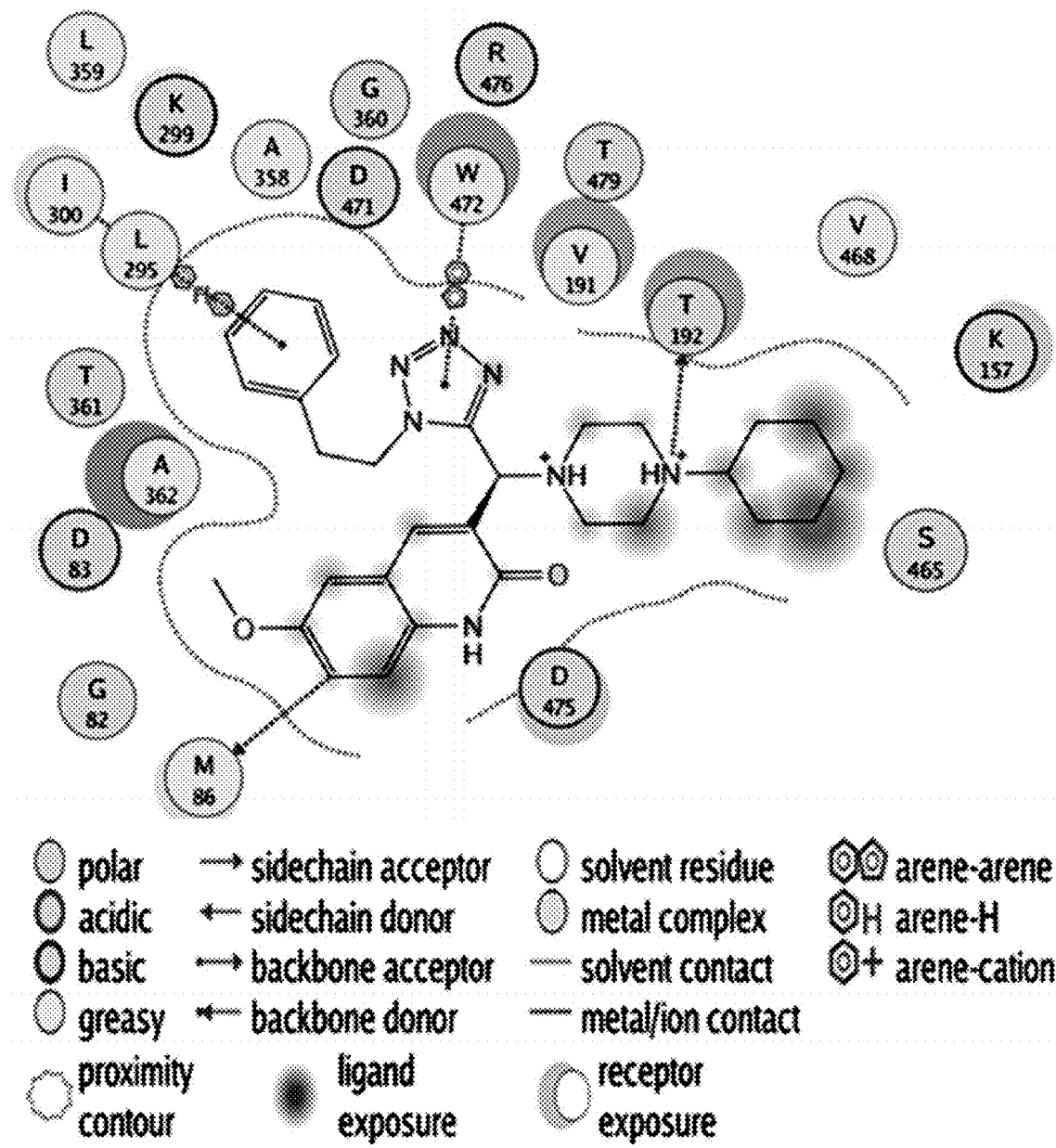
Figure 5C:
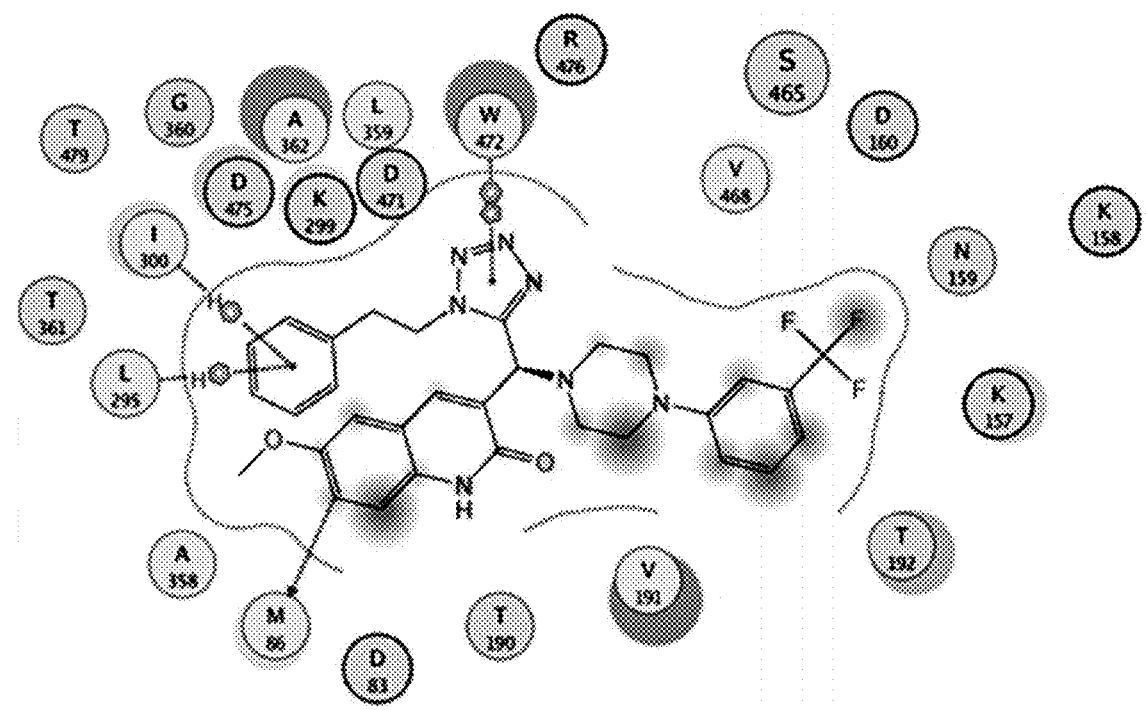

On the basis of the customized scoring, the 10 best ranking protein-ligand complexes were identified. These 10 best ranking molecules were then tested in in vitro assays for functional selectivity and allosteric activity at the EAAT2. As illustrated in FIG. 5C, one of the compounds identified using this approach exhibited favorable EAAT2-activating activity. Compound GT949 increased glutamate uptake with an $ED_{50}=0.26$ nM.

Site-Directed Mutagenesis:

To explore the role of the amino acid residues used as anchors in the pharmacophore and/or lining the allosteric binding cavity, mutated EAAT2 transporters were produced. Mutations were from wild-type (WT) pCMV5-EAAT2 vector (Arriza, et al., 1994, J. Neurosci. 14:5559-5569) to neutral amino acids or to opposite-charged amino acids, to change particular selected residues in a reciprocal manner, using the QUIKCHANGE® site-directed mutagenesis kit (Agilent Technologies, Wilmington, DE). The mutants generated in this study were H71S, M86V, L290A, L295A, G298A, K299A, S465L, and W472I. Mutations were verified by DNA sequencing.

Neurotransmitter Transporter Studies in Cell Lines:

Cell Culture and DNA Transfection:

COS-7 cells were maintained in DMEM with 10% fetal calf serum under 5% $CO_2$. Transfection with empty vector pCMV-5 was used to control for the level of endogenous uptake of radiolabeled substrate in each experimental condition. The specificity of the effect of the compounds was investigated in COS-7 cells transiently transfected with glutamate transporter subtypes EAAT1-3 and monoamine transporters hNET (human noradrenaline transporter), hDAT (dopamine transporter), and hSERT (serotonin transporter).

For glutamate uptake assays, subconfluent COS-7 cells were transfected with 0.5 µg of plasmid DNA per well using TransIT-LT1 transfection reagent (Mirus Bio LLC, Madison, WI) and plated at a density of ~100 000 cells per well in 24-well tissue culture plates. For monoamine uptake assays, cells were transfected 0.1 µg of DNA per well as above and plated at a density of 10 000 cells per well in 96-wells plates.

Dose-Response Assays:

Two days after transfection, the cells were washed with room temperature phosphate buffer PBS-CM (2.7 mM KCl, 1.2 mM $KH_2PO_4$, 138 mM NaCl, 8.1 mM $Na_2HPO_4$, with 0.1 mM $CaCl_2$ and 1 mM $MgCl_2$ added, pH 7.4) and incubated for 10 min at 37° C. with several concentrations of the indicated compounds (0.01-100 nM). Uptake reactions were initiated by the addition of 50 nM $^3H$-L-glutamate, serotonin, dopamine, or noradrenaline, as appropriate.

Kinetic Assays:

Cells were transfected with wild-type (WT) EAAT2 or mutants. Two days later, uptake reactions were initiated by the addition of unlabeled L-glutamate and $^3H$-L-glutamate (1-1000 µM, final concentration, 99% unlabeled and 1% labeled).

All reactions were carried out for 10 min; then, uptake was terminated by removal of solution, followed by two washes with PBSCM. Cells in 24-well plates were lysed with 1% SDS/0.1 M NaOH. Lysate was transferred to scintillation vials containing 3 mL of scintillation fluid, and radioactivity was quantified in an LS 6500 scintillation counter (Beckman Coulter, Brea, CA). For 96-well plates, scintillation fluid was added to each well, and the plate was counted in a Wallac M50 microbeta scintillation analyzer.

Glutamate Transporter Studies in Astrocytes:

Astrocyte Preparation:

Glia was prepared and cultured according to Shimizu, et al., 2011, J. Visualized Exp. e3257 with modifications. Briefly, cerebral cortices from 2-4 day old Holtzman rat pups were dissected under sterile conditions and placed in 60 mm dishes containing dissection medium (in mM: 16 glucose, 22 sucrose, 135 NaCl, 5 KCl, 1 $Na_2HPO_4$, 0.22 $KH_2PO_4$, 10 HEPES, pH 7.4, Osmolarity 310+10 mOsm). Tissue was minced with curved scissors and digested in 0.25% trypsin for 15 min. Trypsin activity was ended by transferring tissue pieces to another vial with dissection medium. Tissue was then repeatedly passed through a serological plastic pipette until it was dissociated by trituration in the presence of 60 µg/mL DNase. Cells were pelleted by centrifugation for 15 min at 280 g and resuspended in glia plating medium (90% DMEM, 10% FBS, and 50 µg/mL gentamicin) and transferred to culture flasks kept in a 37° C. incubator (5-10% $CO_2$). After growth for 10 days in vitro (DIV), cells were detached with 0.05% trypsin, centrifuged, and plated at a density of 10 000 cells/well in polylysine-coated 96-well plates. Plates were grown for 14 DIV before uptake assays were performed.

Uptake Assays:

Assays were performed as described (Timple, et al., 2013, J. Nat. Prod. 76:1889-1895). Briefly, using an Elx50 Biotek plate washer (Winooski, VT, USA), cells were washed in PBS-CM buffer. For dose-response assays, vehicle and several concentrations of the compounds (0.01 nM to 1 µM) were added and incubated for 10 min at 37° C. Uptake assays were initiated by addition of 50 nM L-[$^3H$]-glutamate, and incubation was carried on for 10 min at room temperature. Nonspecific uptake was obtained in the presence of 10 µM DL-TBOA.

For kinetic assays, cells were washed in PBS-CM buffer and pre-incubated in the presence of either vehicle or a specific concentration of the compound ($EC_{50}$). Uptake reactions were initiated by the addition of unlabeled L-glutamate and $^3H$-L-glutamate (1-1000 µM, final concentration, 99% unlabeled and 1% labeled). Incubation was carried out for 10 min at room temperature. Nonspecific uptake was also obtained in the presence of DL-TBOA.

Reactions were finished by washing the plates twice with PBS-CM and the addition of 100 µL of scintillation fluid to each well. Radioactivity was counted in a microplate scintillation and luminescence counter (Wallac, Shelton, CT, USA).

Determination of the Effect of Novel Compounds on Glutamate Receptors:

To determine whether the compounds have effects on the function of NMDA receptors, calcium imaging recordings from cultured cortical neurons were performed as described previously (Nicolai, et al., 2010, Cell Death Dis. 1: e33).

Cultured Neurons Preparation:

Primary cortical neurons were obtained from the cerebral cortex of neonatal (P1 or P2) $C_{57}BL/6$ mice, plated at a density of 3000 cells/12 mm round coverslip, and cultured in medium containing Neurobasal A, fetal calf serum (2%), heat-inactivated horse serum (2%), L-glutamax-1 (0.2 mM), and B-27 supplement (2%). Cells were maintained at 37° C. in a humidified atmosphere containing 5% $CO_2$. The calcium imaging experiments were conducted on DIV 1.

Calcium Imaging:

Recordings were performed in living neurons, as described (Xia, et al., 2014, J. Physiol. 592:3443-3461). Briefly, cultured neurons were loaded with a Fura-2 calcium dye in Tyrode's solution containing (in mM) 140 NaCl, 5 KCl, 2 $CaCl_2$, 1 $MgCl_2$, 10 HEPES, and 5.6 glucose. Coverslips were mounted in the imaging chamber (model RC-25, Warner Instruments, Hamden, CT) and continuously perfused with Tyrode's solution containing 0.5 µM tetrodotoxin. Images were acquired in 3 s intervals at room temperature (20-22° C.) using an Olympus inverted microscope equipped with a CCD camera (Hamamatsu ORCA-03G, Japan). The fluorescence ratio was determined as the fluorescence intensities excited at 340 and 380 nm with background subtracted. 100 µM NMDA was applied in the presence of 3 µM glycine and in the absence of $Mg^{2+}$. The NMDA receptor antagonist AP-V (40 µM) was applied to certify that the result was specifically the NMDA-induced calcium response. Vehicle, GT949, or GT951 was applied, and calcium changes were recorded.

Calcium Imaging:

Recordings were performed in living neurons, as described (Xia, et al., 2014, J. Physiol. 592:3443-3461). Briefly, cultured neurons were loaded with Fura-2 calcium dye in Hank's balanced salt solution (HBSS). 100 µM NMDA was applied in the presence of 3 µM glycine and in the absence of $Mg^{2+}$. The NMDA receptor antagonist AP-V (40 µM) was applied to certify that the result was specifically NMDA-induced calcium response. Vehicle, GT949, or GT951 was applied, and calcium currents were recorded.

Data Analysis:

All data were analyzed using GraphPad Prism version 5.03 for Windows (GraphPad Software, La Jolla, CA). Dose-response assays were analyzed by nonlinear regression for calculation of $EC_{50}$'s or $IC_{50}$'s and assessment of efficacy of the compounds. Graphs represent the average ±SEM of at least three independent experiments performed in triplicate and normalized to percentage of control (vehicle). Michaelis-Menten kinetics was assumed for calculation of $K_m$ and $V_{max}$. Statistical significance was assessed using one-way analysis of variance (ANOVA) followed by Dunnett's or Bonferroni multiple comparisons post hoc tests with vehicle (for analysis of the effect of compounds) as control ($*p<0.05$).

Example 1

The present disclosure relates to the identification and characterization of novel compounds that bind to the EAAT2 activation domain, using HSB virtual screening. Traditional high-throughput screens have been unsuccessful in identifying compounds that directly increase the activity of EAAT2. The HSB method used herein allows for the identification of small molecule modulators to several drug targets. As demonstrated herein, structural and computational methods can be used to screen compound libraries to identify compounds that bind to the venom binding site and display favorable activity.

Figure 6A:
FIGS. 6A-6B illustrate structural models of EAAT2 modeled based on the corresponding Glt(ph) structures and proposed binding site residues.
Figure 6B:
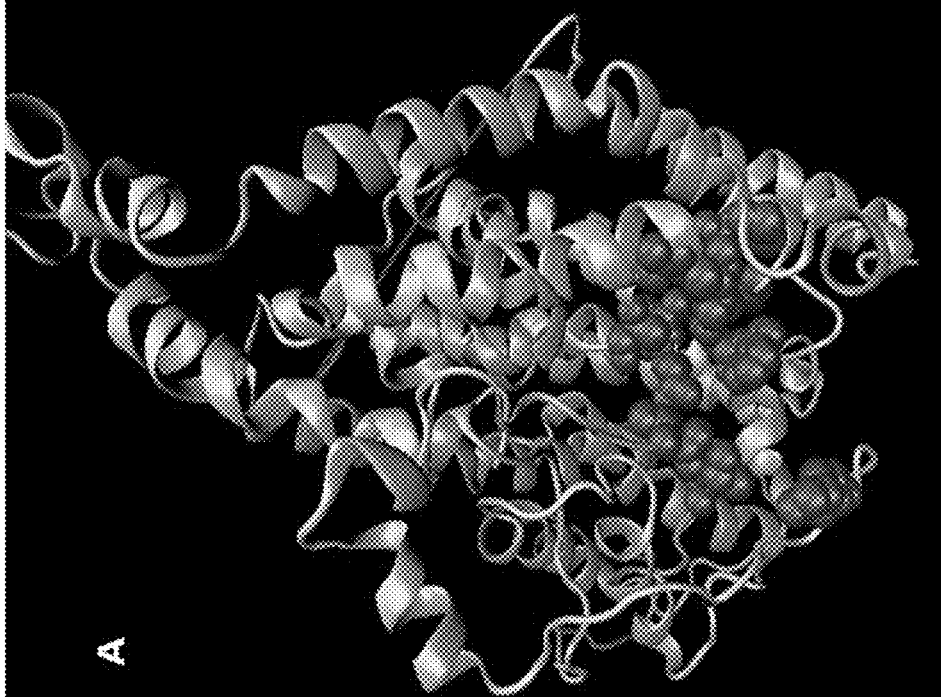

In one aspect, the interaction of compounds with the activation domain was explored by performing structure/function studies with the venom and novel compounds on mutants within the activation domain. These include the mutants highlighted in FIG. 6A: V75, D83 [TM2], L290, L295, G298 [TM5], and W472 [TM8], and also additional mutants that structural modeling has identified as located within the activation domain (highlighted in FIG. 6A: H71S, A79S, M86V, K90Q, A302I, I303A, T361A, A362I, S444A, and R476K). Assays include the characterization of the compounds and venom in dose response and kinetic assays on glutamate transport in both wild type and mutated transporters. These mechanistic studies further refine the activation domain by establishing critical residues of interaction with an activating compound. This structural information can be subsequently used to refine the pharmacophore to guide additional HSB screens to identify compounds with optimal activity.

The development of potent and selective compounds can also involve testing: a) the specificity of the compounds on COS-7 cells expressing EAAT1-3, and b) their activity in rat brain cortex synaptosomes to verify activity in an endogenous environment. The action of active compounds in a more endogenous environment is tested using cultured astrocytes from neonatal rat brain cortices. Compounds can be tested for toxicity by incubating them with COS-7 cells for 12 and 24 hours and measuring release of LDH. As illustrated in FIGS. 8-13, the methods described herein allowed for the identification of efficacious compounds.

Example 2: In Silico Screening Identified Novel EAAT2 Allosteric Modulators

Figure 19A:
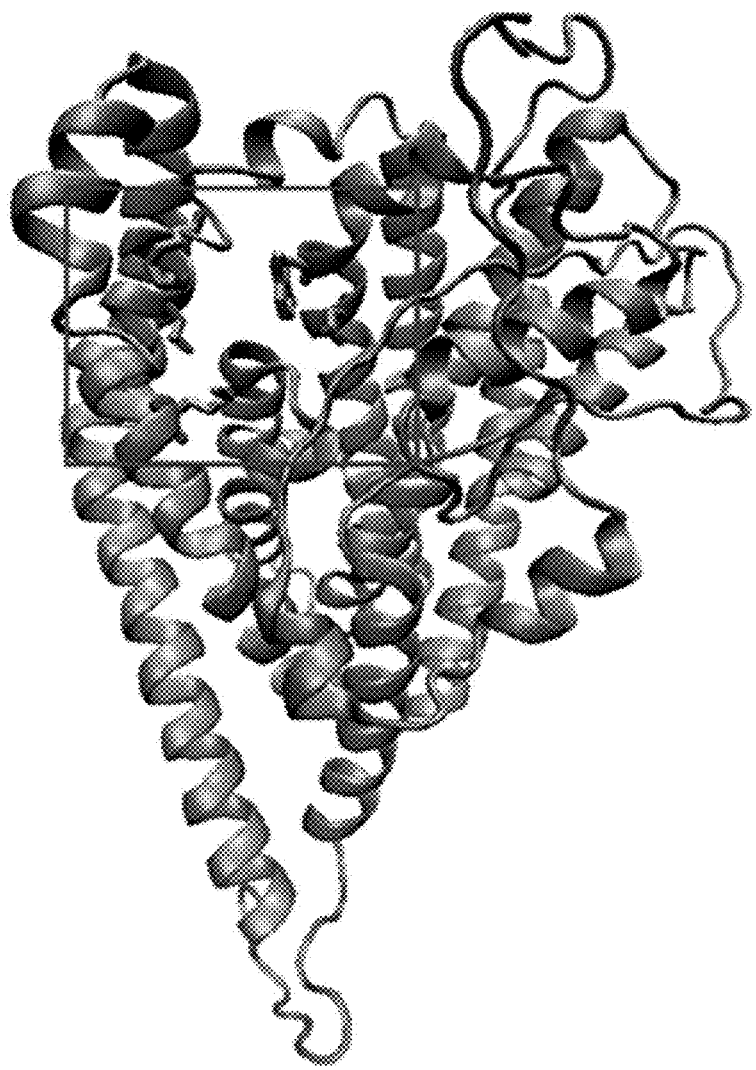
FIGS. 19A-19B illustrate pharmacophore design using residues from the allosteric site.
Figure 19B:
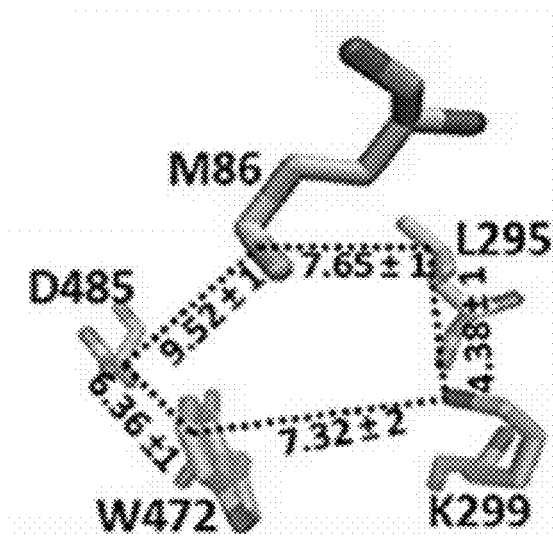

Molecular dynamics simulations of the modeled EAAT2 in a 1-palmitoyl-2-oleoyl-sn-glycero-3-phosphocholine (POPC) membrane indicated presence of an allosteric pocket in a located at a structural interface between the transport and surrounding trimerization domains (FIG. 19A). Such region is important for facilitating conformational changes during the translocation cycle. This region is distal from the central substrate binding region formed by Hairpins 1 and 2, suggesting that compounds interacting at this site have an allosteric mode of action.

From the molecular dynamics simulation, five residues, namely, M86, L295, K299, W472, and D485, that lined the allosteric pocket were identified. Using these five residues, a five-point three-dimensional "receptor pharmacophore" (FIG. 19B) was designed for virtual screening of assembled libraries.

The virtual screening approach identified 10 molecules that were evaluated in dose-response assays for glutamate uptake in COS-7 cells expressing EAAT2 (FIG. 17). Among the 10 molecules, three compounds (GT949, GT951, and GT939) were found to be PAMs of EAAT2, whereas four molecules (GT729, GT835, GT938, and GT922) were inhibitors (negative allosteric modulators, NAMs) and three molecules (GT867, GT988, and GT996) had no effect. In this study, further characterization of compounds GT949 and GT951 was pursued to demonstrate and characterize positive allosteric modulation of EAAT2.

The NAMs shown in FIG. 17 are significantly less potent than the PAMs. Without wishing to be limited by any theory, this can be a result of positive cooperativity between the substrate glutamate and the PAMs for activating uptake. For some allosteric modulators of GPCRs allosteric compounds have different affinities for the active and inactive states of the receptor. In certain non-limiting embodiments, both PAMs and NAMs of EAAT2 are of relatively low affinity, but in the presence of the substrate glutamate the affinity of PAMs is significantly increased to enable uptake augmentation. This cooperativity is different, or maybe absent, for NAMs and consequently results in much lower affinity for inhibiting uptake.

Figure 20A:
FIGS. 20A-20B illustrate a structural comparison of EAAT1 and EAAT2.
Figure 20B:
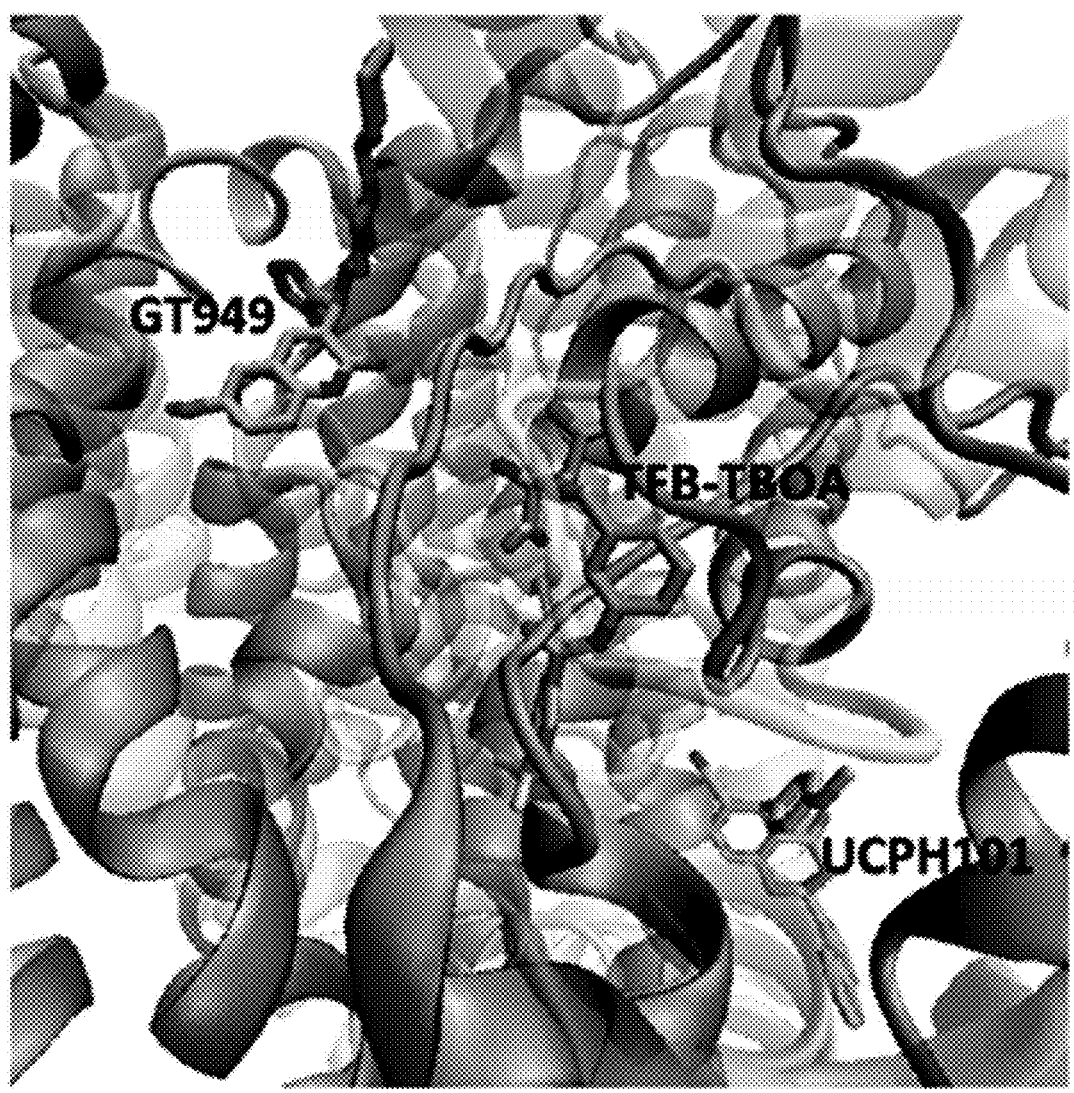

The crystal structure of the human EAAT1 was solved in complex with substrate L-aspartate, competitive inhibitor TBOA, and allosteric modulator UCPH-101 (Canul-Tec, et al., 2017, Nature 544:446-451). A structural superposition of the presently modeled EAAT2 onto this crystal structure of EAAT1 indicated that, although both of these proteins share the GltPh-like domain architecture, they have significant differences in the arrangement of their helices (FIGS. 20A-20B) due to large insertions or deletions in EAAT1. UCPH-101 binds toward the inner opening of the membrane and at a site that is distinctly different from the allosteric site that bind PAMs such as GT949, which is toward the outer opening of the membrane, and there are no shared residues between the two sites. Both of these allosteric sites are proximal to the inhibitor binding site but on diagonally opposite ends and may exist simultaneously in EAAT2, but the UCPH-101 crevice in EAAT2 may be smaller than that observed in EAAT1. The substrate binding pocket is structurally conserved between EAAT1 and EAAT2.

Example 3: Compounds of the Invention Stimulate EAAT2-Mediated Glutamate Transport with High Potency and Selectivity for EAAT2 and No Effects on EAAT1 or EAAT3

Figure 8A:
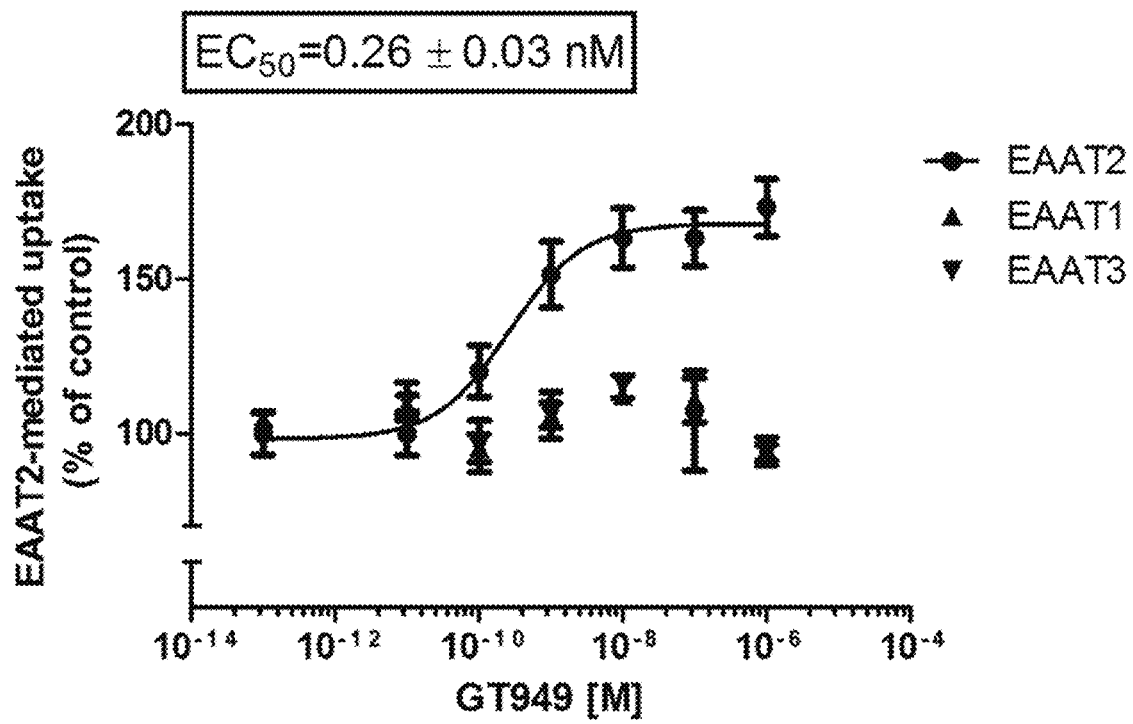
FIGS. 8A-8B comprise graphs illustrating dose-response studies of GT949 (FIG. 8A) and GT951 (FIG. 8B) in glutamate transport assays. Assays were performed in COS-7 cells transiently transfected with appropriate cDNA (chimeras or mutants) or empty vector. Cells were incubated with varied concentrations of compounds for 10 min at 37° C. and 5 min with 50 nM $^3$H-L-glutamate. Results were normalized to percentage of control (vehicle) and expressed as mean±SEM of three independent experiments. GT949 exhibited an $EC_{50}$=0.26±0.03 nM with an increase of ~70% in glutamate transport mediated by EAAT2, with no effect on EAAT1 or EAAT3. GT951 showed an $ED_{50}$=0.8±0.3 nM for EAAT2, and no effect on EAAT1 or EAAT3-mediated glutamate transport.
Figure 8B:
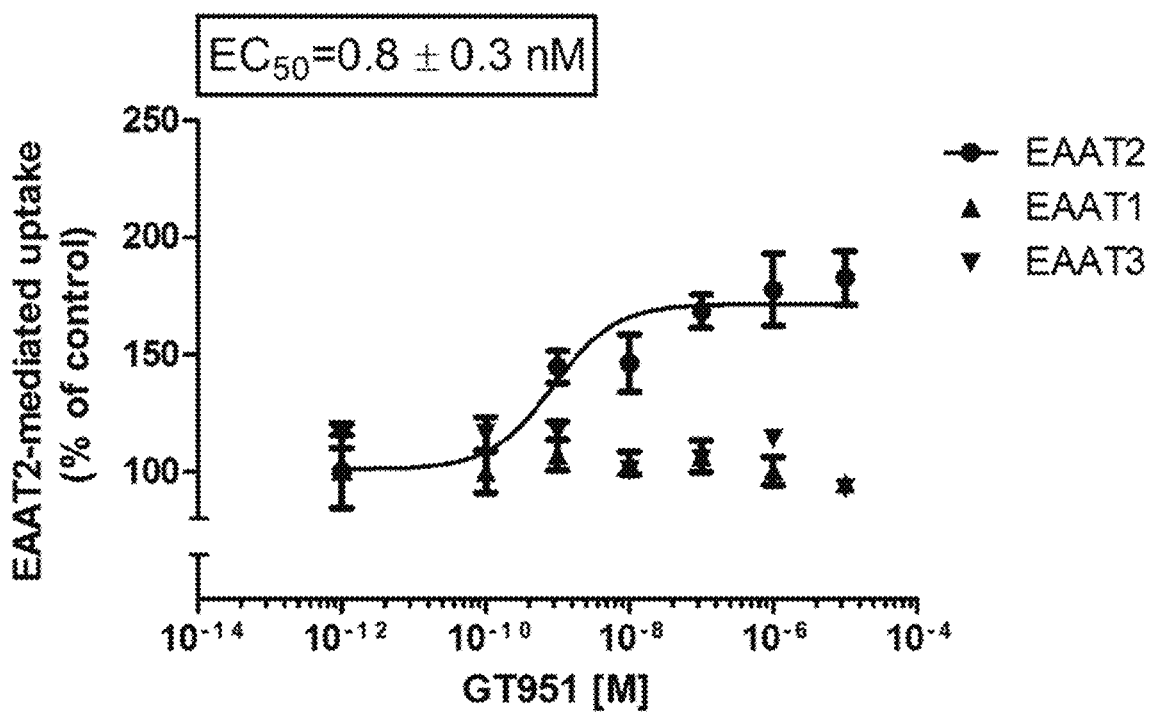
Figure 9:
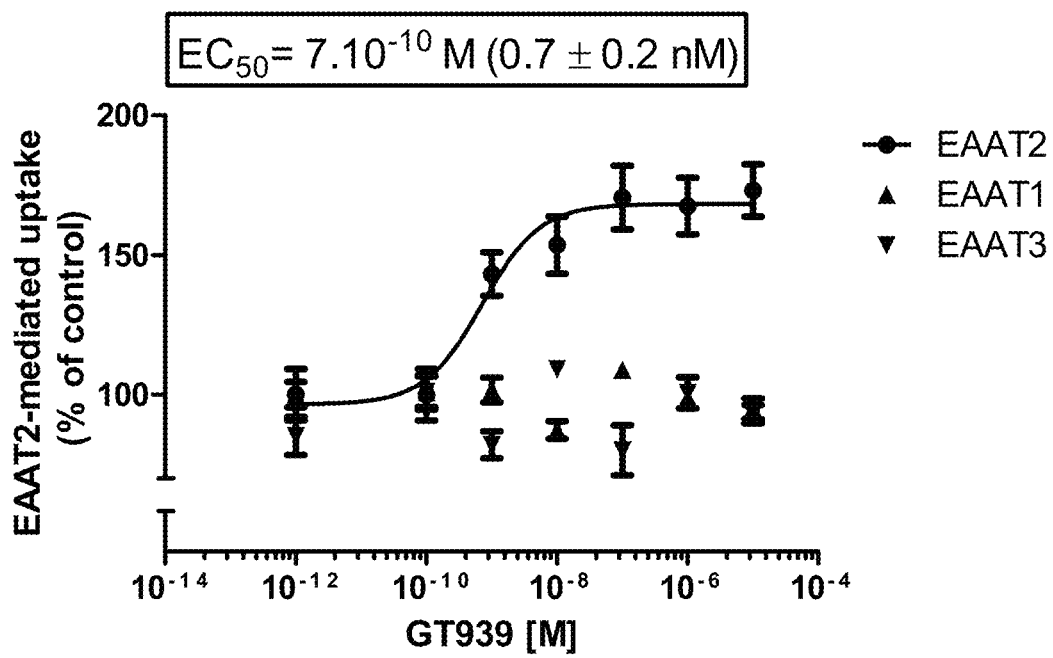
FIG. 9 is a graph illustrating that dose-response studies with GT939 showed stimulation of EAAT2 transport with an $ED_{50}$=0.7±0.2 nM but no effect on EAAT1 or EAAT3-mediated glutamate transport.

Potent hit compounds GT949 and GT951 were evaluated in a dose-response assays on glutamate uptake in COS-7 cells transfected with EAAT1, 2, or 3. In this assay, T949 and GT951 enhanced glutamate transport with $EC_{50}$ values of 0.26±0.03 and 0.8±0.3 nM, respectively (FIGS. 8A-8B). The increase in rate acceleration for glutamate removal by EAAT2 was ~70% for both compounds, which is comparable to Parawixin-1 (70%). GT949 and GT951 also demonstrated selectivity to EAAT2 and had no effect on glutamate activity mediated by EAAT1 or EAAT3 (FIGS. 8A-8B).

Example 4: Compounds are Noncompetitive Positive Allosteric Stimulators of EAAT2

Figure 10:
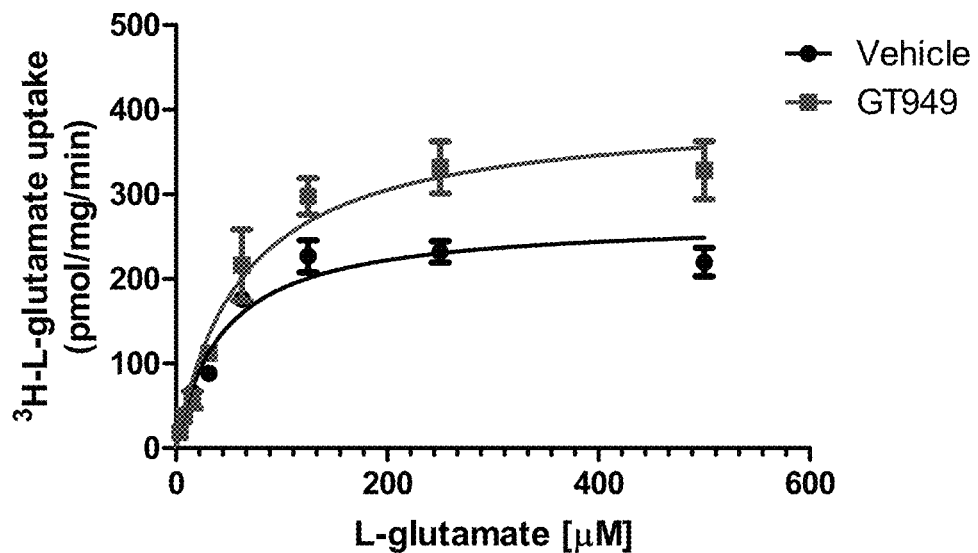
FIG. 10 illustrates kinetic assay results for L-glutamate uptake in transfected Cos-7 cells pre-incubated with 1 nM GT949. This compound showed allosteric stimulation of the EAAT2 transporter, with increased $V_{max}$ of transport and similar $K_m$ value, suggesting a non-competitive fashion. $V_{max}$ and $K_M$ were calculated from at least three independent experiments performed in triplicate, values are presented in the table; $K_M$ was not statistically different between the groups. *** p<0.001, drug compared to vehicle.
Figure 11:
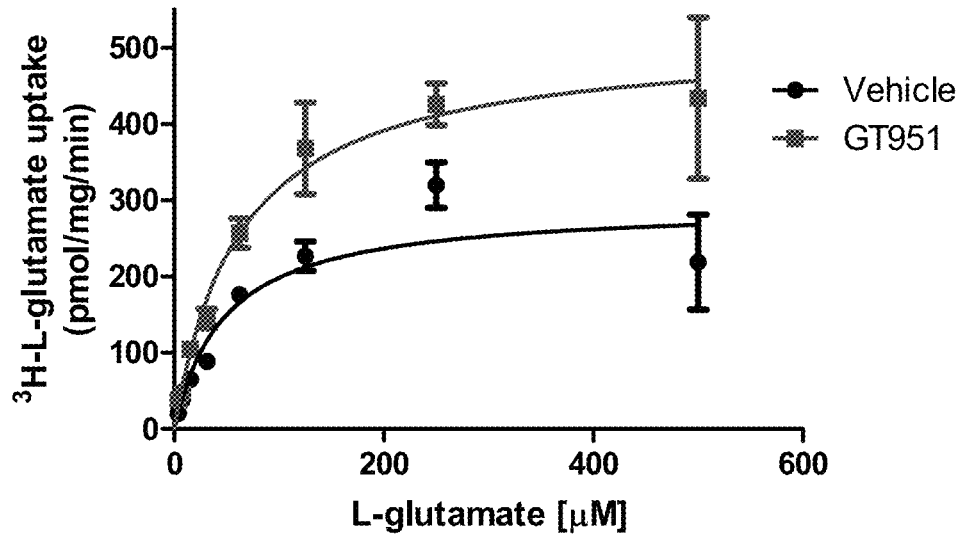
FIG. 11 illustrates kinetic assay results for L-glutamate uptake in transfected Cos-7 cells pre-incubated with 1 nM GT951. This compound showed allosteric stimulation of the EAAT2 transporter, with increased $V_{max}$ of transport and similar $K_m$ value, suggesting a non-competitive fashion. $V_{max}$ and $K_M$ were calculated from at least three independent experiments performed in triplicate, values are presented in the table; $K_M$ was not statistically different between the groups. *** p<0.001, drug compared to vehicle.
Figure 12:
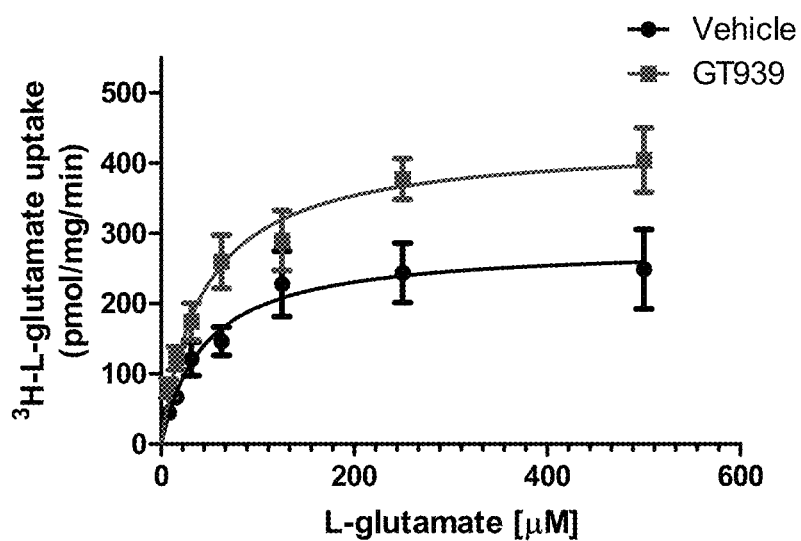
FIG. 12 illustrates kinetic assay results for compound GT939. This compound showed allosteric stimulation of the EAAT2 transporter, with increased $V_{max}$ of transport and similar $K_m$ value, suggesting a non-competitive competitive fashion.

GT949 and GT951 were also tested for their effect on glutamate uptake kinetics in EAAT2-transfected cells. Both compounds enhanced glutamate transport in a noncompetitive fashion, with increases in $V_{max}$ of about 47 and 75% for GT949 and GT951, respectively (FIGS. 10-11). $K_M$ was not statistically different between the groups (one-way ANOVA followed by Dunnett's post hoc test comparing to vehicle). This strongly indicates that they work through positive allosteric modulation.

Example 5: Potency of the Enantiomers is Different

Figure 7:
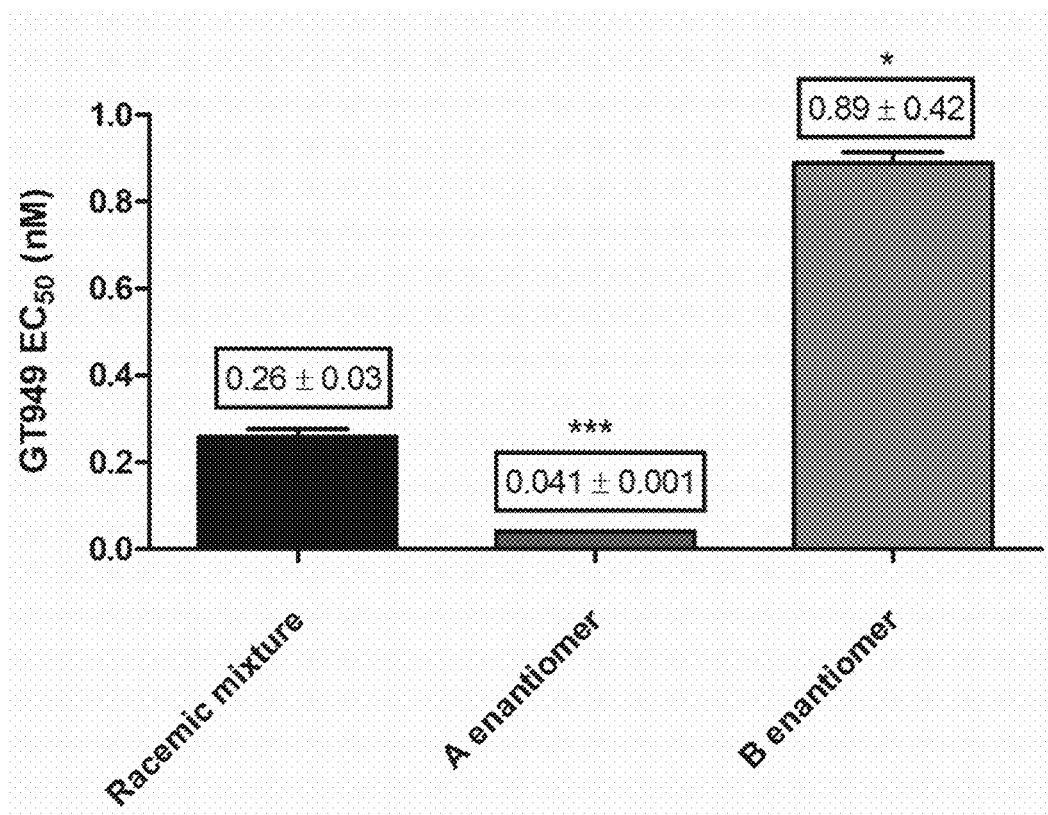
FIG. 7 shows the potency of purified enantiomers of GT949 on EAAT2-mediated glutamate uptake. GT949 is a racemic mixture of enantiomers, and the single enantiomers of this compound were separated by chiral HPLC, using a 4.6×250 mm CHIRALPAK® IA column (Chiral Technologies, France) and a 60% isopropanol/hexane gradient, at 1 ml/min flow. Assays were performed in COS-7 cells transiently transfected with EAAT2 or empty vector. Cells were incubated with varied concentrations of compounds for 10 min at 37° C. and 5 min with 50 nM $^3$H-L-glutamate. Results are the mean±SEM of at least three independent experiments. The figure show that the A enantiomer is 22-fold more potent than the B enantiomer, and 6-fold more potent than the racemic mixture.

The docking studies indicated differences in potency and binding between the R and S enantiomers of GT949. Since GT949 was initially tested as a racemic mixture of the enantiomers, GT949 was subject to chiral separation. The GT949A enantiomer was 22-fold more potent than the GT949B enantiomer and 6-fold more potent than the racemic mixture (FIG. 7). This provides compelling evidence that these molecules are interacting in the chiral environment of the allosteric binding site.

Example 6: Compounds Stimulate Glutamate Transport in Cultured Astrocytes

Figure 13A:
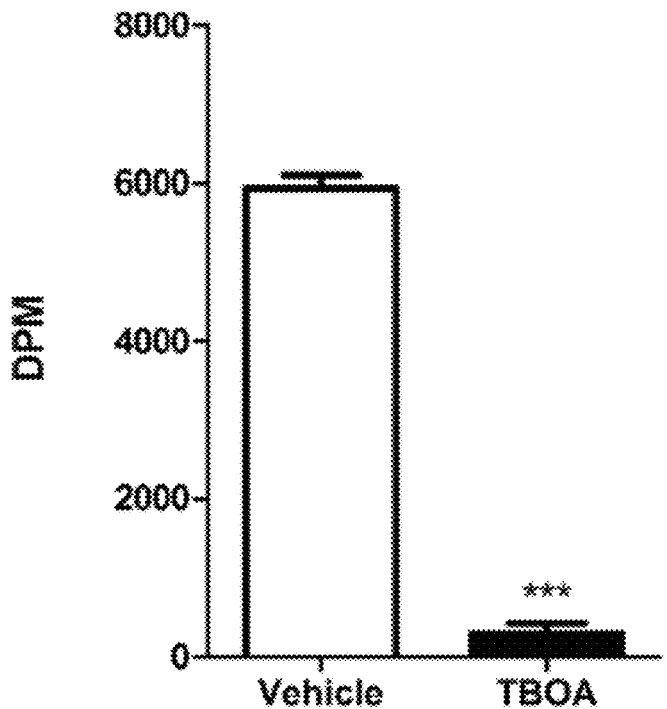
FIGS. 13A-13D show glutamate transport assays performed in cultured astrocytes, a preparation in which a dense expression of EAAT2/GLT-1 was observe by western blots and immunohistochemistry.
Figure 13B:
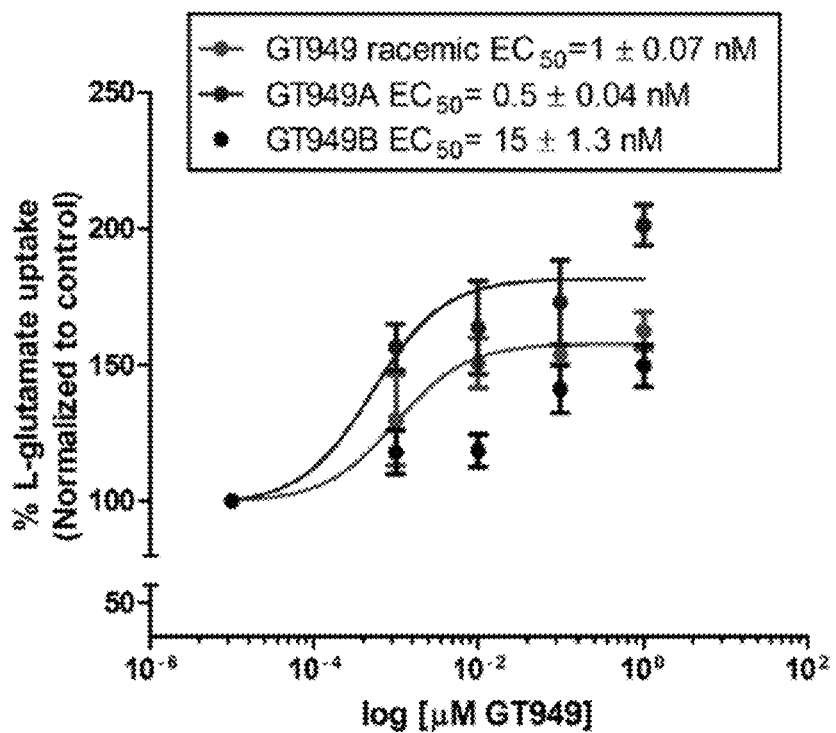
Figure 13C:
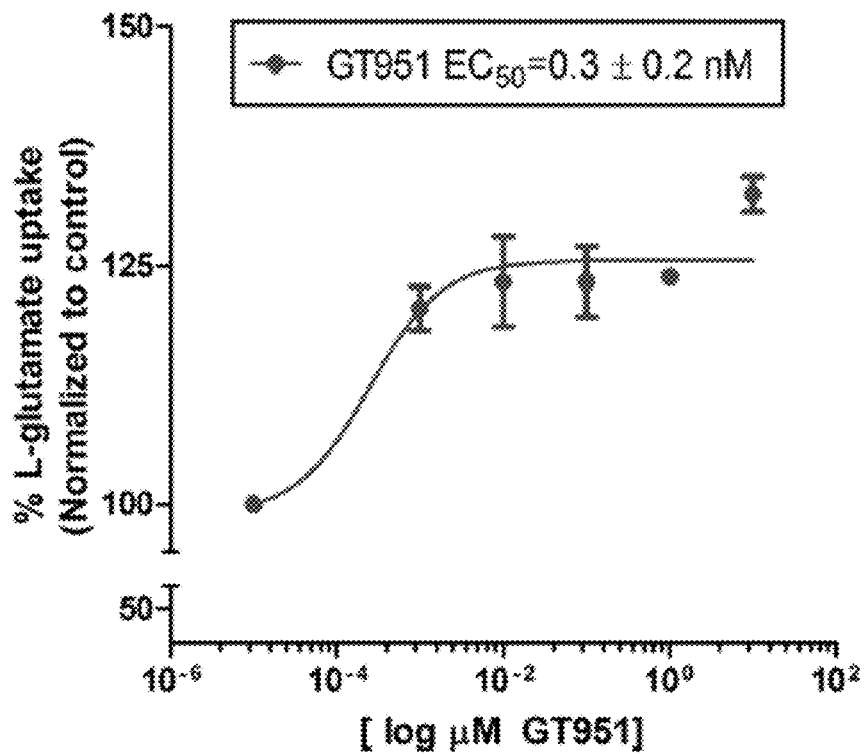
Figure 13D:
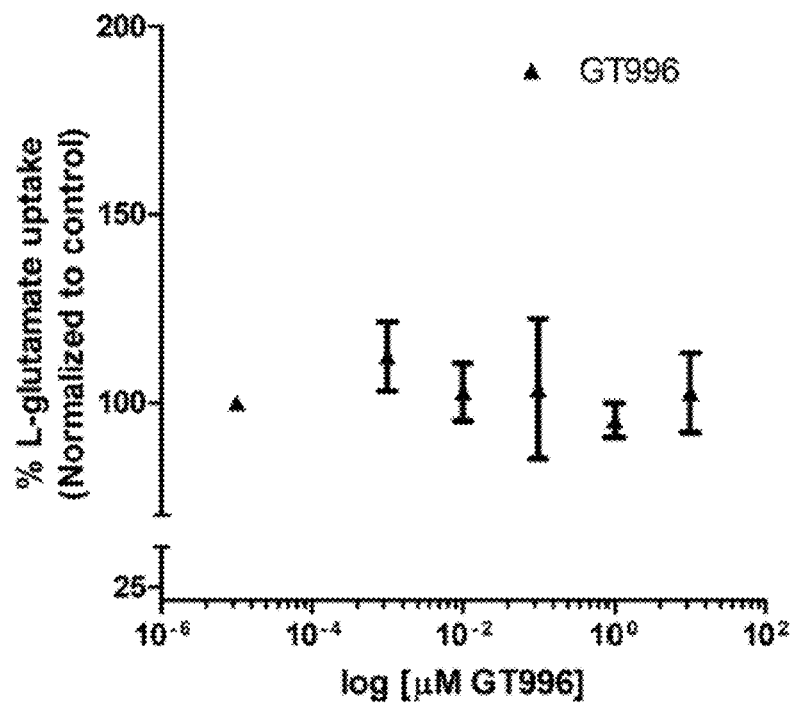
Figure 14:
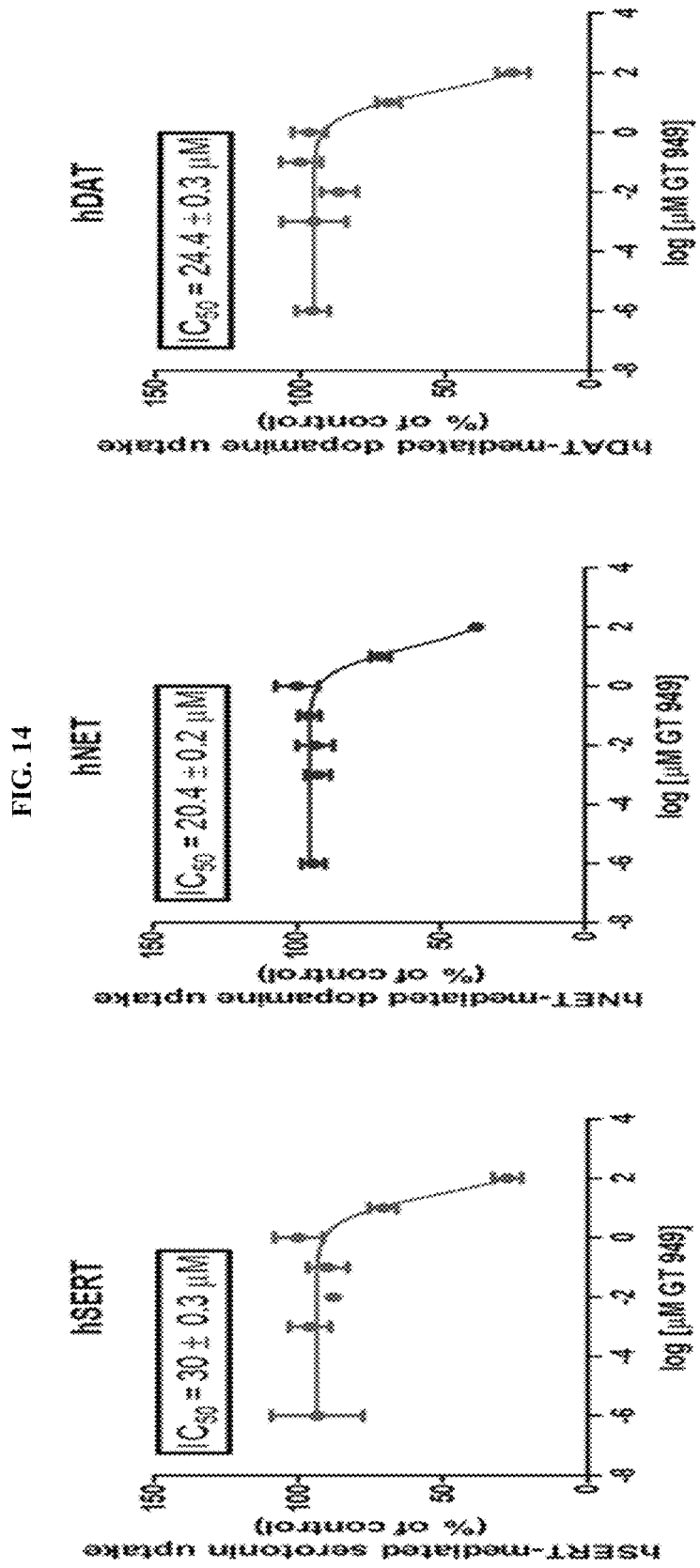
FIG. 14 illustrates the compounds GT949 and GT951 are selective towards glutamate transporters, over monoamine transporters. Serotonin, noradrenaline and dopamine uptake mediated by monoamine transporters hSERT, hNET, and hDAT, respectively, are not affected by compound GT951, with $IC_{50}s>100$ mM. GT949 showed slight inhibitory action with $IC_{50}$ in the micromolar range.

GT949 and GT951 were tested for effects on glutamate uptake mediated by cultured astrocytes (FIGS. 13A-13D). On the basis of the initial glutamate uptake assay in COS-7 cells, GT996 was chosen as a negative control. Raw data (DPM) demonstrated that the background, obtained in the presence of TBOA, represented ~5% of the specific signal (FIG. 13A). Dose-response curves of GT949 (racemic mixture and separated enantiomers, FIG. 13B) show that potencies vary from 1±0.07 nM (racemic mixture) to 0.5±0.04 nM (enantiomer A) and 15±1.3 nM (enantiomer B). The efficacy of augmentation was ~58 and 50% for the racemic mixture and B enantiomer, whereas the A enantiomer was more efficacious, resulting in an 81% increase in transport. GT951 had an $EC_{50}$ value of 0.3±0.2 nM and efficacy of uptake enhancement of ~27% (FIG. 13C). GT996 was inactive at modulating glutamate transport in cultured astrocytes (FIG. 7D). These data confirm that the compounds are active in a native environment of EAAT2, namely, cultured glia and astrocytes.

A difference in potencies of the compounds was observed between the overexpressing heterologous cell lines and the primary glial cultures. The racemates and the separated enantiomers are much less potent in glial cells than in COS-7 cells, although the trend is maintained, in which the A enantiomer is more potent than B. Without wishing to be limited by any theory, differences in potencies can be related to cell-specific factors such as post-translational modifications of EAAT2 that impact the structure of the allosteric site and/or differences in cellular proteins that interact with and regulate EAAT2.

Figure 21:
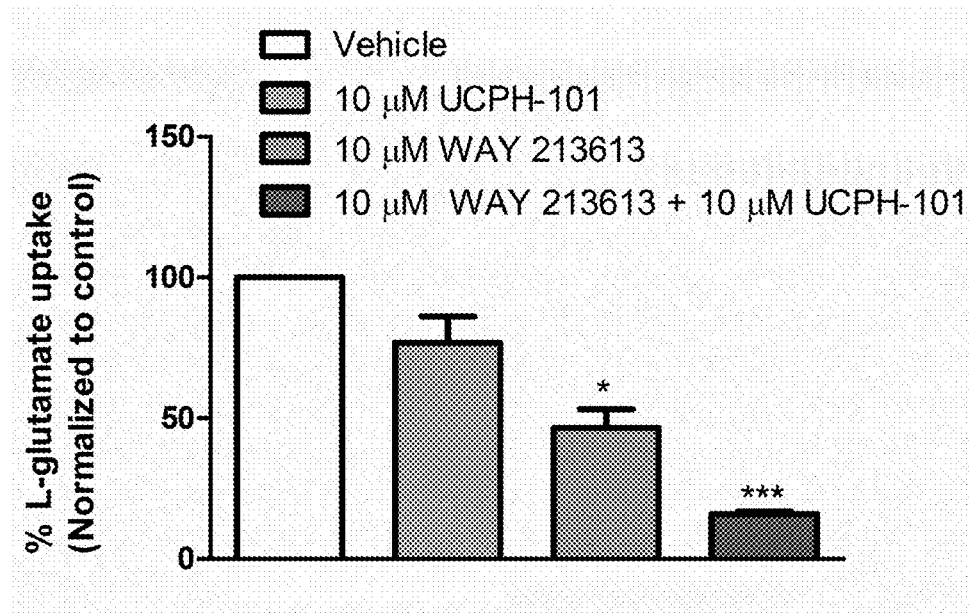
FIG. 21 illustrates an effect of glutamate uptake inhibitors on glutamate uptake in cultured astrocytes. Glutamate uptake was performed in presence of 50 nM $^3$H-L-glutamate. Incubation with compounds UCPH-101 (a selective inhibitor of EAAT1) and WAY 213613 (selective inhibitor of EAAT2) resulted in different levels of inhibition. Compounds were purchased from Tocris (Bristol, UK).

To understand the contribution of the various EAAT subtypes to glutamate uptake in cultured glial cells, uptake inhibition assays were performed with selective inhibitors of the various EAATs (FIG. 21). The data suggest that glutamate uptake in these cultures is mediated at least in part by EAAT2 (shown by partial inhibition by WAY 213613, a selective EAAT2 inhibitor) but also by EAAT1 (shown by partial inhibition by UCPH-101, a selective EAAT1 inhibitor) and possibly EAAT3 (since not all of the uptake was inhibited by the combination of EAAT1 and 2 inhibitors). Therefore, EAAT2 transporter mediates glutamate uptake in our astrocyte cultures, in addition to other EAAT transporters.

Figure 22:
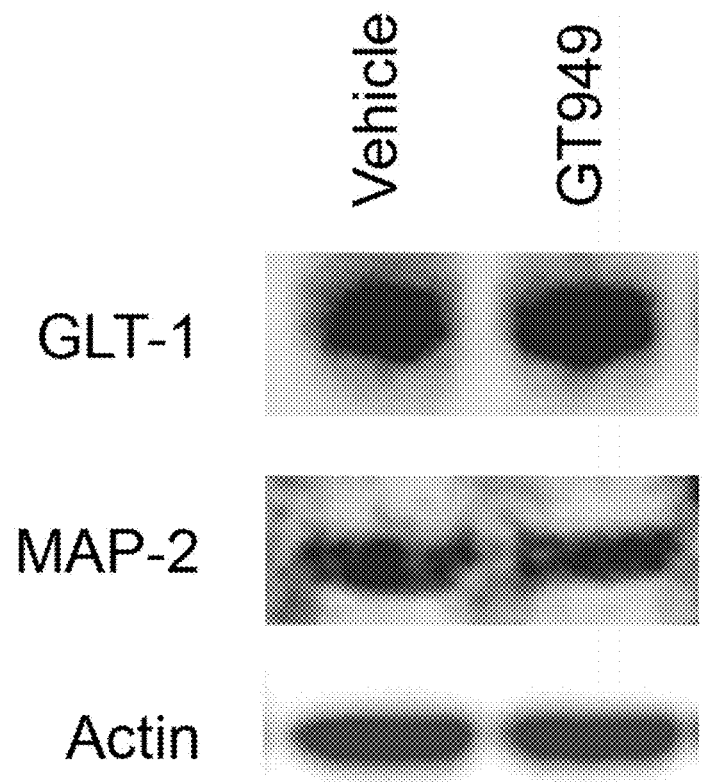
FIG. 22 illustrates a representative immunoblot of samples of cultured glia (14 DIV) incubated for 24 h with vehicle or 1 μM GT949, illustrating expression of GLT-1 (1:1,000), MAP-2 (1:1,000, Millipore #AB5622) and loading control β-actin (1:1,000, Cell Signaling #3700).

Immunoblotting was also performed to further support the pharmacological studies, and the results validated the presence of GLT-1/EAAT2 in the astrocyte cultures (FIG. 22). In these assays, the presence of neurons was also demonstrated, as indicated by the microtubule associated protein marker MAP-2. Pure astrocyte cultures express only GLAST. However, transporter activity can be regulated in different ways, including gene expression, transporter protein targeting and trafficking, and post-translational modifications of the transporter protein. In this regard, some studies have suggested that added glutamate and/or growth factors can induce expression of astroglial glutamate transporters GLT-1 and GLAST, and others suggest that, in co-cultures of astrocytes with neurons, expression of GLT-1 is induced in astrocytes while expression of GLAST is slightly augmented. Thus, without wishing to be limited by any theory, as the present glia culture also contains neurons, this could be responsible for inducing the expression of EAAT2.

Example 7: Compounds have Low Affinity Inhibitory or No Effect on Monoamine Transporters and do not Modulate NMDA Activity Receptor in Primary Cultures Dose-response curves of GT949 and GT951 demonstrated a lack of modulation of the activity of human serotonin (hSERT), noradrenaline (hNET), and dopamine (hDAT) transporters at the highest concentration tested ($IC_{50}$>1 mM).

Figure 15:
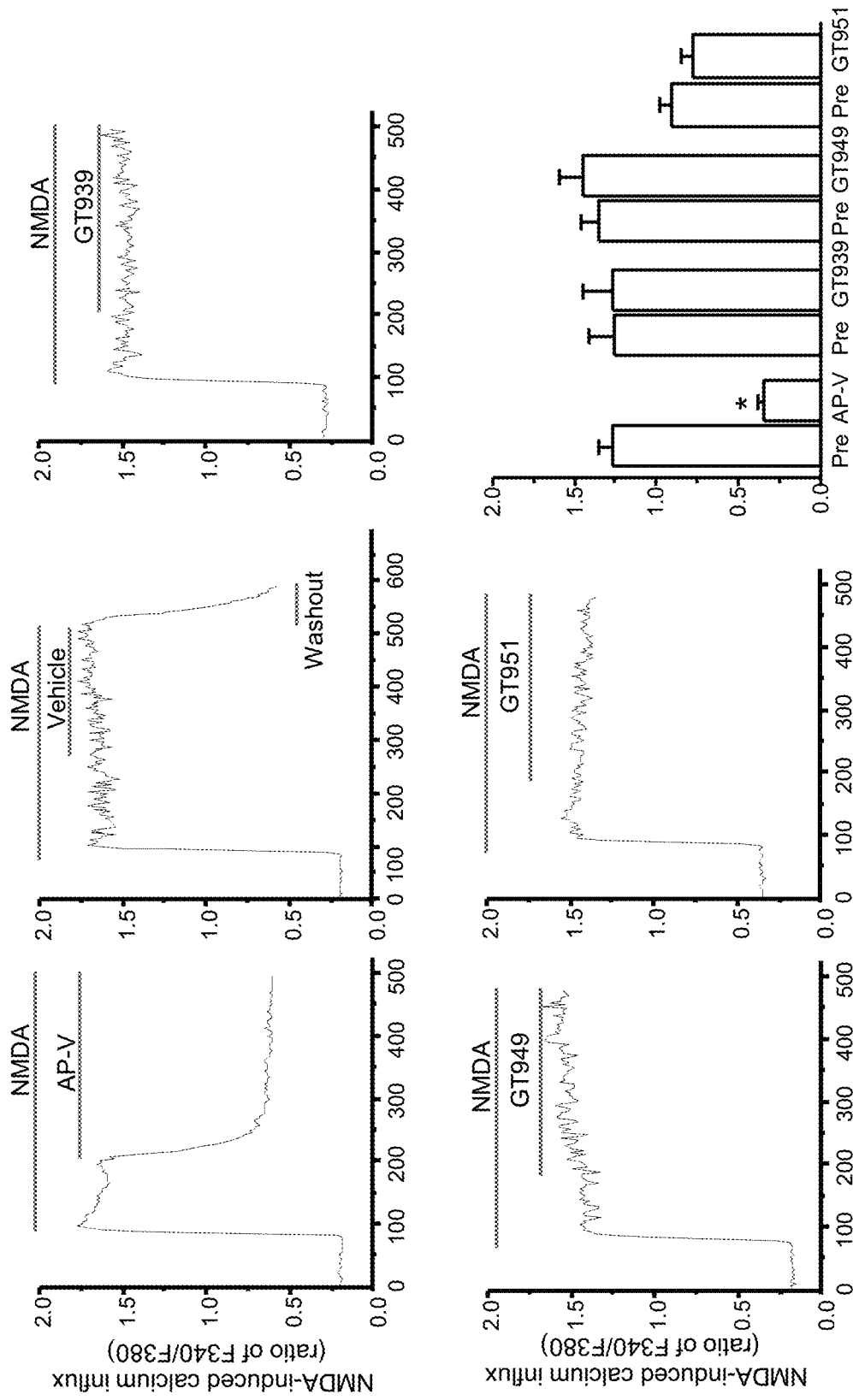
FIG. 15 shows the effects of compounds GT939, GT949 and GT951 on NMDA-induced calcium influx. Calcium imaging recordings were made from cultured cortical neurons in Tyrode's solution. Application of 100 μM NMDA with 3 μM glycine in the absence of $Mg^{2+}$ induced a sustained calcium response, which was drastically attenuated by 40 μM AP-V, a specific NMDA receptor antagonist, suggesting that NMDA-induced calcium response is mediated by NMDA receptors. The bar graph illustrates results for AP-V (n=16), GT949 (n=19), and GT951 (n=19). Vehicle, compounds GT939, GT949 and GT951 had no effects on NMDA-induced calcium response, suggesting that compounds do not interact with NMDA receptors. Values represent mean±SEM; *P<0.05, compared with Pre-drug treatments (Pre) by the paired t-test.
Figure 16:
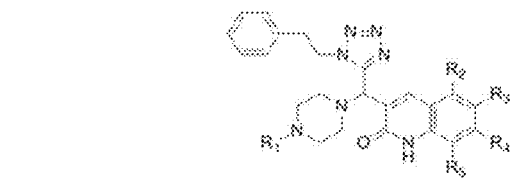
FIG. 16 shows the structure of certain compounds contemplated in the present invention.
Figure 18A:
FIGS. 18A-18C illustrate a trimeric structure of GltPh viewed in the plane of the membrane with one protomer colored in shades of red, blue, green, and yellow and the two other protomers colored in gray. The trimer is shown in a side view (FIG. 18A) and top view (FIG. 18B). A single protomer with transport domains represented in green and scaffold domains in red is shown in (FIG. 18C).
Figure 18B:
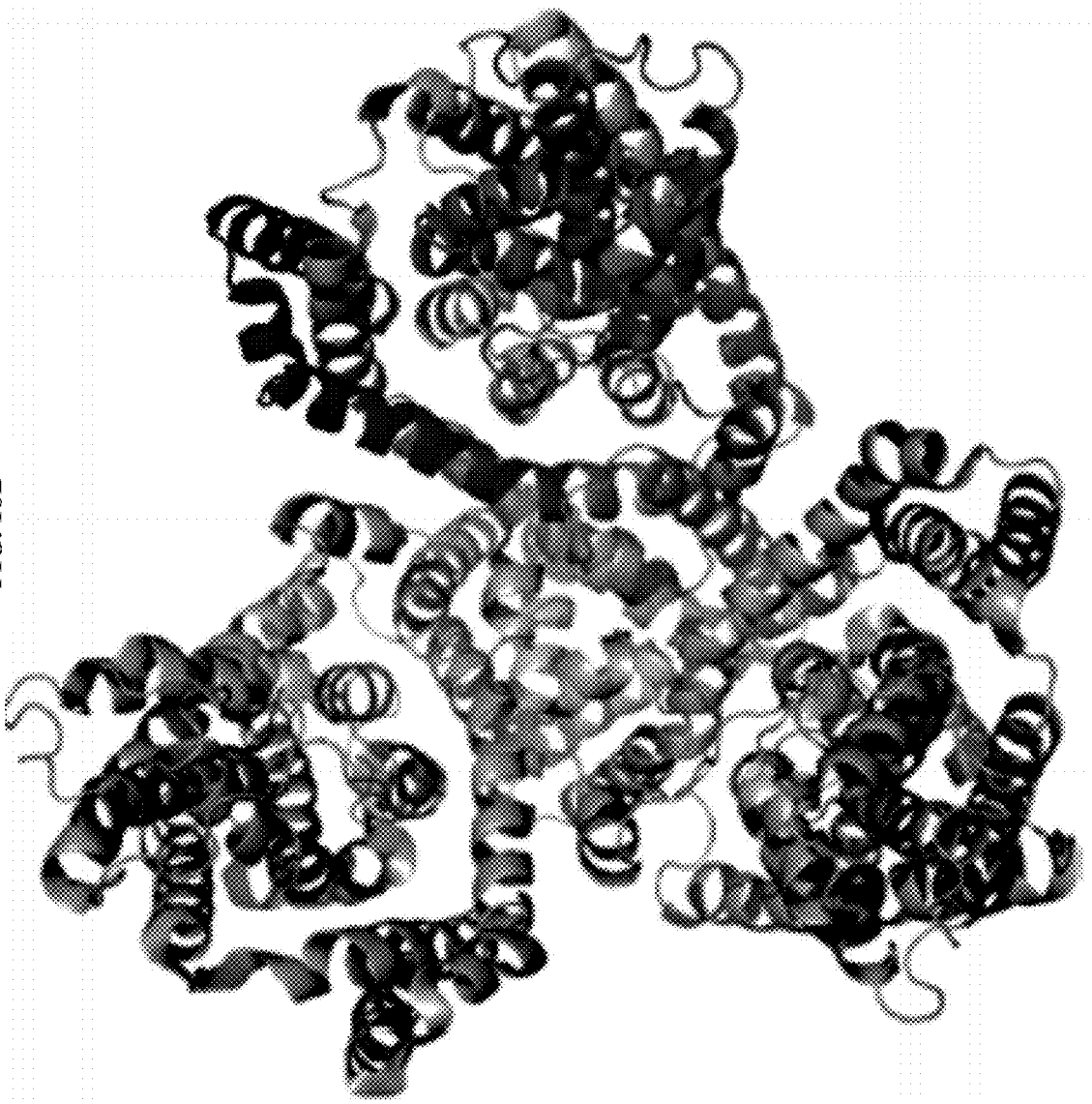
Figure 18C:
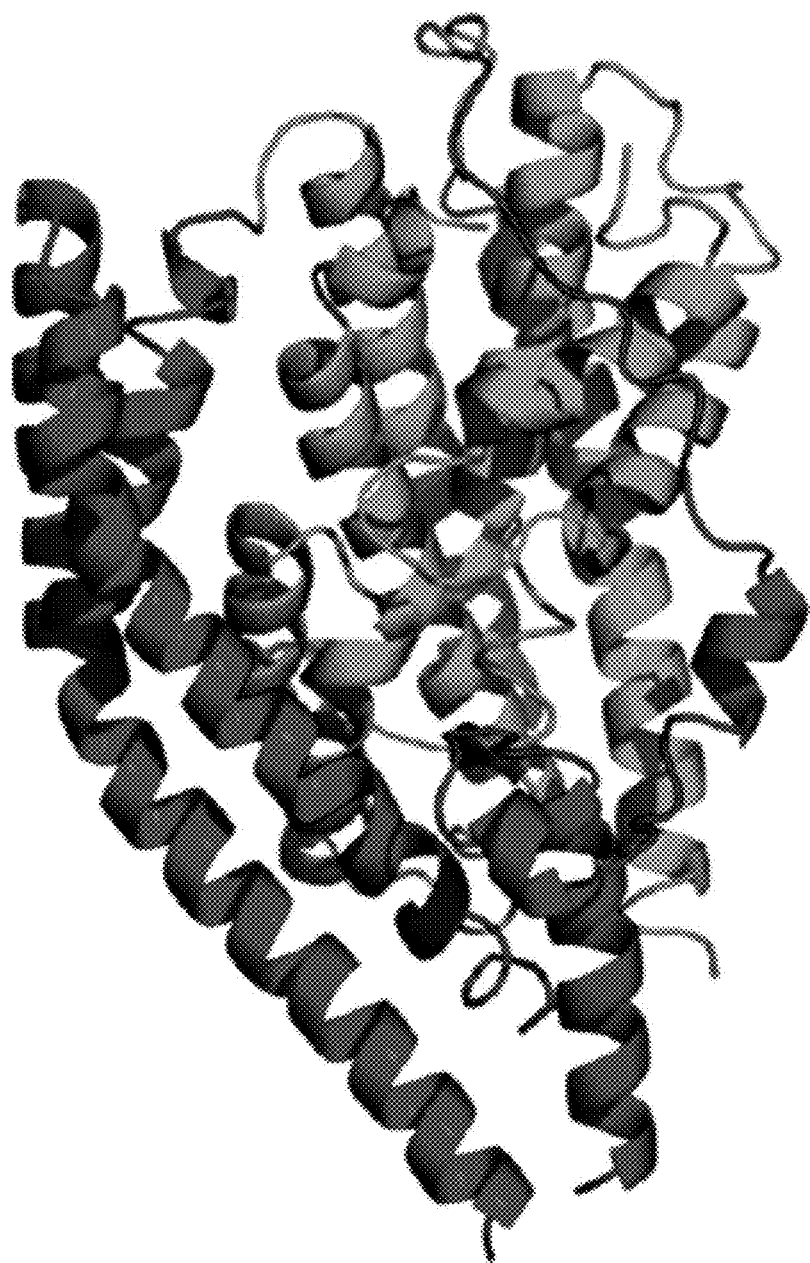

Application of 100 μM NMDA with 3 μM glycine in the absence of $Mg^{2+}$ in neuronal cultures induced a sustained calcium response. This response was drastically attenuated by 40 μM AP-V, a specific NMDA receptor antagonist, suggesting that the NMDA-induced calcium response was mediated by NMDA receptors. Vehicle, GT949, or GT951 had no effect on NMDA-induced calcium response, indicating that the compounds do not modulate the activity of NMDA receptors (FIG. 15).

The lack of inhibition of NMDA receptors indicates that these compounds are devoid of the serious side effects that have limited the translation of NMDA receptor antagonists to the clinic. Taken together, these initial selectivity evaluations indicate that the compounds are selective for glutamate transporter EAAT2 over transporters EAAT1 and EAAT3 and monoamine transporters, and that they do not affect NMDA receptor activity.

Example 8: Structure-Function Studies: Compounds GT949 and GT951 Engage EAAT2 in a Similar Fashion as Parawixin-1

To provide additional evidence that Parawixin-1 and the novel small molecule hits (GT949 and GT951) are engaging the transporter in a similar fashion, dose-response curves of the compounds were recorded on eight different EAAT2 mutants: H71S, M86V, L290S, L295A, G298A, K299A, S465L, and W472I (Table 1). These mutants were selected because of their role in transport enhancement elicited by the venom and their role in the pharmacophore design in the HSB screening. These structure-function studies of structural determinants of the binding pocket were also guided by the molecular modeling and docking studies shown in FIGS. 5A-5C. Specifically, changes in potencies for GT949 on the EAAT2 mutants suggest that residues in TM2, TM5, and TM8 in the putative activation domain (FIG. 5A) are important for transport enhancement and that residues M86 (TM2), L295 (TM5), S465 (TM8), and W472 (TM8) are critical for GT949 activity. Molecular docking of GT949 to EAAT2 supports these studies as M86, L295, S465, and W472 all contribute directly to the binding of GT949 (FIG. 5B). Mutations such as H71S, L290S, and G298A of residues that are not found to be in direct contact with GT949 in the docking studies also do not significantly affect GT949 modulation of EAAT2 in functional studies. Similar to GT949, docking studies indicate that the binding affinity of GT951 in the pocket can be influenced by direct interactions with M86, L295, K299 (TM5), S465, and W472 (FIG. 5C). Site-directed mutagenesis studies confirmed that potencies for GT951 were indeed affected by mutations of all of these residues but not by mutations like H71S, L290S, and G298A.

Some differences are to be noted between the present findings regarding the novel compounds and the venom. In the studies of the venom, residue S465 was not found to be important for its action. This was taken as evidence that the venom was interacting with an outward-facing conformation when residue W472 is in closer vicinity to the other critical residues compared to S465. In the present study, both S465 and W472 were important for the action of both GT949 and GT951. Without wishing to be limited by any theory, this can suggest that the novel compounds also interact with the inward-facing conformation; however, as visualized by docking studies in FIGS. 5B-5C, the present compounds can interact with both residues at the same time when interacting with the outward-facing conformation.

In summary, both the functional mutagenesis studies and the docking studies found that the present compounds interact with the interface between the trimerization and transport domains at a binding site shaped by key residues (M86, L295, K299, and W472). Both the docking and structure-function studies also suggest that the novel molecules engage the transporter in a fashion analogous to that of the spider venom natural product (Table 1).

TABLE 1

Residues in TMs 2, 5, and 8 within the Putative Activation Domain Are Important for Transport Enhancement by GT949 and GT51.

| transporter | $EC_{50}$ | |
| --- | --- | --- |
| | GT949 | GT951 |
| EAAT2 | 0.26 ± 0.03 nM | 0.8 ± 0.3 nM |
| H71S | 0.36 ± 0.14 nM[a] | 0.2 ± 0.02 nM[a] |
| M86V | 170 ± 24 nM | no stimulation |
| L290A | 0.5 ± 0.11 nM[a] | 0.16 ± 0.08 nM[a] |
| L295A | no stimulation | 666 ± 42 nM |
| G298A | 0.2 ± 0.01 nM[a] | 0.2 ± 0.05 nM[a] |
| K299A | 0.25 ± 0.08 nM[b] | no stimulation |
| S465L | no stimulation | no stimulation |
| W472I | no stimulation | no stimulation |

$EC_{50}$ (expressed as mean ± SD) of the effects of GT949 and GT951 on glutamate uptake assays mediated by several mutants investigated herein. Results showing significant changes in $EC_{50}$ are in bold, indicating residues important for compound activity. Changes in efficacy of the compounds on some mutants were observed, as compared to efficacy on EAAT2 WT.
[a]Higher efficacy compared to EAAT2 WT.
[b]Lower efficacy compared to EAAT2 WT.

The present studies allow for identification of direct and selective positive allosteric modulators (PAMs) of EAAT2 glutamate transport. This mechanism of action can have several therapeutic applications for treating conditions that involve excitotoxicity. Without wishing to be limited by any theory, an approach based on direct positive allosteric modulation of EAAT2 activity has advantages compared with earlier approaches targeting EAAT2 that all relied on increasing levels of EAAT2 protein expression. Because positive allosteric modulation is a fast direct process, it does not require synthesis and trafficking of new protein and will consequently have immediate acute effects and not rely on prophylactic pretreatments.

Also, concerns about protein upregulation following chronic treatments and resulting potential side effects of the earlier approaches have given rise to concerns. Regarding this issue, there were no observed effects of GT949 on the expression of GLT-1 expression (FIG. 22). Immunoblotting of samples of glia incubated for 24 h with or without 1 μM GT949 revealed that GLT-1 expression is unaffected by GT949, 24 h post treatment. Further, considering that glutamate release is a key early event in excitotoxicity, increasing glutamate clearance through PAM of EAAT2 can be more efficacious than targeting downstream signaling processes that are activated following excitotoxicity.

The present studies have allowed for the identification of neuroprotective compounds that function by enhancing removal of excessive glutamate in the synaptic cleft and preventing glutamate-mediated excitotoxicity. In certain embodiments, the compounds of the invention can be used to promote in vivo neuroprotection under acute conditions such as traumatic brain injury and stroke, but also chronic neurodegenerative disorders such as Alzheimer's disease, Parkinson's disease, and ALS. Aberrant glutamate signaling has also been implicated in mental health disorders and drug use disorders, and EAAT2 PAMs can therefore have therapeutic potential for these conditions as well.

Example 9: In Vitro Models of Glutamate Excitotoxicity

Excitotoxicity involves over-activation of NMDA receptors by glutamate and subsequent calcium influx and inappropriate activation of downstream signaling pathways that contribute to cytoskeletal damage and neuronal cell death. The hypothesis of whether preventing excess glutamate signaling through glutamate clearance can prevent excitotoxic damage and cell death is examined. In certain embodiments, treatment with EAAT2 activators attenuates cell death in primary cortical neurons subjected to glutamate excitotoxicity.

As described herein, the overall strategy is to subject cortical neurons to excitotoxic insults and examine the potential neuroprotective effect of newly identified EAAT2 activators. The approach involves an initial screening based on MAP 2 staining to examine overall neuronal survival and to establish optimal dose/application time of experimental compounds. This initial screening can be coupled to additional cell survival analyses (using probes that detect differences among healthy, apoptotic, and necrotic cells) for a more extensive characterization of the effects of selected compounds.

Bilaminar Co-Culture of Primary Rat Cortical Neurons and Glia:

Because the novel compounds activate a glial transporter (EAAT2), the bilaminar culture approach in which neurons are cultured in the presence of a glial layer is used. Rat cortical neurons are obtained from late embryonic stage (E17), then plated and cultured for 18 days in vitro (18 DIV) on coverslips (15-mm diameter) at a density of 35,000 cells/coverslip, facing a feeder layer of glia. The glial feeder layer, an astroglia-enriched secondary culture of mixed glia, is separately prepared from the cortices of newborn rat pups (P2-4) prior to the neuronal dissection. In this system the neuronal layer contains >95% neurons.

Excitotoxicity Assays:
(i) Glutamate and NMDA Induced Excitotoxicity:
Insults are performed as outlined herein (Nicolai, et al., 2010, Cell Death Dis. 1:e33). Briefly, at 18 DIV neurons are subjected to excitotoxicity with either glutamate (to activate all subtypes of glutamate receptors) or NMDA (to specifically activate NMDA receptors), both at 100 µM, or vehicle, for 20 min in absence of glia.

(ii) Glucose/Oxygen Deprivation (OGD) Model of Ischemia:
OGD is induced on 11 DIV (Goldberg, et al., 1994, J. Diary Sci. 77(11):3338-46). Cell culture plate medium is replaced with glucose free Earle's salt solution and placed in a SHEL LAB Bactron Anaerobic Chamber (Sheldon Manufacturing, Cornelius, OR) filled with anaerobic mixed gas (5% $CO_2$-5% $H_2$-90% $N_2$) at 37° C. for 3 h. OGD is terminated by removal of cell culture plates from the anoxic chamber and replacement of culture medium.

(iii) Oxidative Stress Model of Excitotoxicity:
Cell cultures are exposed to $H_2O_2$ for 30 min (Lee, et al., 2004, Neurochem. Int. 44(2):107-18).

Furthermore, a stretch model of in vitro TBI is employed—a model that has been shown to closely mimics TBI in vitro and has also been associated with increases in extracellular glutamate and with receptor activation leading to calcium elevation and cell death. Glia-neuron hippocampal cultures are employed to examine the properties of the novel compounds on neuronal death after stretch injury. The overall strategy is to subject cortical or hippocampal neurons to excitotoxic insults or stretch injury and examine the potential neuroprotective effect of the compounds.

(iv) Stretch Injury Model of TBI:
Insults are performed in 7-10 DIV hippocampal neurons. Biaxial stretch is applied to the cells using the Cell Injury Controller II system (Virginia Commonwealth University) with 50 ms pulse duration to moderate and severe stretch injury (45 and 63 psi, respectively).

After insults (glutamate, NMDA, OGD, oxidative stress or stretch injury) neurons are returned to their original culture dishes containing the glial feeder layer (except for hippocampal neurons that are cultivated in 6 wells plates in the mixed culture approach), and either vehicle or specific compounds in 4 doses (1.0 nM-1.0 µM) is applied at the following time points following the insult: 30 min, 2 or 6 h. 24 h after the insults MAP-2 staining or cell survival assays are performed. As positive and negative controls for neuroprotection, 40 µM AP-V (a specific NMDA receptor antagonist), and GT867 (an inactive GT949 analog), are respectively applied.

Initial Screening of Novel Compounds on Neuronal Survival Using Microtubule Associated-Protein 2 (MAP-2) Staining:

To quantify neuronal survival (as a function of MAP-2) and the effect of treatment with the EAAT2 activators, cell-based MAP-2 ELISAs are performed. Neurons are plated at a density of 35,000 cells/well in 24-well plates. Following experimental treatments, cultures are fixed and fluorescently labeled using mouse anti-MAP-2 (Sigma), goat-anti mouse (3-lactamase TEM-1 conjugate and FLU-OROCILLIN™ Green substrate (both from Invitrogen). Fluorescence intensity is measured using a Victor2 fluorescence and luminescence reader (PerkinElmer, Waltham, MA).

These studies can allow for the determination of an optimal dose and application time of the compounds to be examined in the cell survival studies.

Characterization of the Effects of Compounds on Cell Survival:
To investigate the effect of the compounds using a more refined approach, a combination of propidium iodine (10 µm/mL)/fluorescein diacetate (10 µg/mL) to stain dead and viable cells, respectively and Hoescht 3342 (5 µg/mL) for nuclear staining is performed in 6-well plates. Five to ten random fields per coverslip and six coverslips are analyzed per treatment for each independent experiment.

Statistical Analysis:
MAP-2 fluorescence units are expressed as percentage of control cultures (no insult). Cell death is expressed as percentage of neuronal death comparing control, insult and treatments. Statistical comparisons are determined using ANOVA, followed by Newman-Keuls post hoc testing (p<0.05).

Without wishing to be limited by any theory, by examining several types of insult (NMDA, glutamate, OGD, oxidative stress and stretch injury) that share the glutamate excitotoxicity component, one can determine whether the mechanism of neuroprotection displayed by the compounds is through increased glutamate clearance. In the case that ameliorated rates of cell death in the proposed treatments are not observed, one alternative strategy is to add the compounds during the insults.

Further studies include evaluation of translational possibilities using in vivo brain injury models, and/or examination of routes of administration, therapeutic window, and combination with long-term treatment strategies.

Taken together, the studies described herein allow for the identification of EAAT2 activators and characterization of their neuroprotective role on excitotoxic events in vitro.

Example 10: Synthesis of GT949

To a stirred solution of 2-hydroxy-6-methoxyquinoline-3-carbaldehyde (100 mg, 0.46 mmol) in 7 ml of isopropanol was added 1-cyclohexylpiperazine (85 mg, 0.50 mmol) and catalytic amount of trifluoroacetic acid and reaction mixture stirred at reflux. After 3 hours trimethylsilylazide (60 mg, 0.46 mmol) and (2-isocyanoethyl) benzene (53 mg, 0.46 mmol) were added to the reaction mixture, and reflux continued for additional 24 hours. After completion of reaction as indicated by TLC reaction mixture cooled to room temperature, the solvent was evaporated under vacuum and crude residue was purified by flash chromatography using (0-15% methanol/dichloromethane) to obtain the pure compound (157 mg, 65.01% yield) as a pale yellow solid. $^1$H NMR (300 MHz, Acetone-$d_6$) δ 8.21 (s, 1H), 7.39-7.30 (m, 2H), 7.29-7.21 (m, 4H), 7.21-7.11 (m, 2H), 5.52 (s, 1H), 4.87-4.73 (m, 2H), 3.88 (s, 3H), 3.31 (t, J=7.5 Hz, 2H), 2.53 (d, J=15.4 Hz, 8H), 2.20 (s, 1H), 1.73 (d, J=9.2 Hz, 4H), 1.57 (d, J=11.7 Hz, 1H), 1.21-1.07 (m, 5H). MS (ESI): m/z 528.4 [M+1]+; HRMS (ESI m/z) for $C_{30}H_{38}O_2N_7$, calcd 528.30815, found 528.30810 [M+1]+.

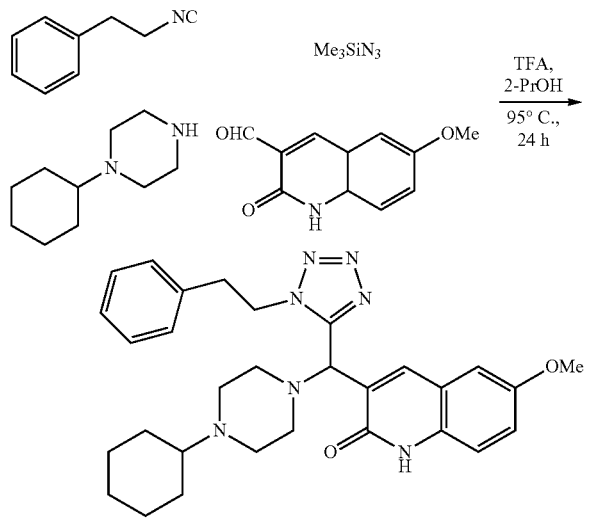

GT949

Chiral HPLC Separation of GT949:

Racemic mixture GT949 was separated by normal phase chromatography using a CHIRALPAK® IA® column (5×50 cm, 20 μm) on an Agilent 1200 HPLC with a Hexane/Isopropanol (40:60) isocratic mobile phase eluting at 35 mL/min and detecting at 236 nm. Separation of 50 mg of the racemic mixture provided 20.4 mg of GT949_1st_neg (GT949A; negative (−) optical rotation or levorotatory) with ee>99%, and 20.0 mg of GT949_2nd_pos (GT949B; positive (+) optical rotation or dextrorotatory) with ee of 98.6%. The area percentages of peak 1 (tR) 4.853 min and peak 2 (tR) 7.010 min were determined to be 50.041% and 49.939%, respectively.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating or ameliorating a disease or disorder that is caused, induced, or characterized by abnormal reduction in EAAT2 glutamate transporter activity or abnormal increase in extracellular CNS glutamate concentration in a subject, the method comprising:
administering to the subject a pharmaceutical composition comprising at least one pharmaceutically acceptable carrier and a therapeutically effective amount of a compound, or an enantiomer, diastereoisomer, salt, or solvate thereof,
wherein the compound is selected from the group consisting of a compound of formula (I), a compound of formula (II), and a compound of formula (III):
(a) a compound of formula (I),

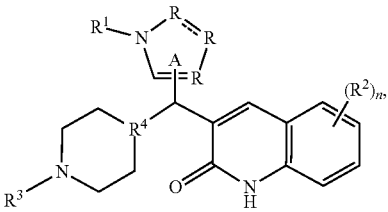

wherein in (I),
each ≡ bond in ring A is independently a double or a single covalent bond, wherein:
(i) when a ≡ bond is a double covalent bond, each R group substituted at the bond is independently selected from the group consisting of N, CH and C($C_1$-$C_6$ alkyl), wherein the alkyl group is optionally substituted; and
(ii) when a ≡ bond is a single covalent bond, each R group substituted at the bond is independently selected from the group consisting of NH, N($C_1$-$C_6$ alkyl), S, O, $CH_2$, CH($C_1$-$C_6$ alkyl) and C($C_1$-$C_6$ alkyl)$_2$, wherein the alkyl group is optionally substituted;
$R^1$ is selected from the group consisting of —$C_1$-$C_6$ alkyl, —$C_1$-$C_6$ heteroalkyl, —($C_0$-$C_3$ alkyl)-($C_3$-$C_6$ cycloalkyl), —($C_0$-$C_3$ alkyl)-($C_4$-$C_{10}$ heterocyclyl), —($C_0$-$C_3$ alkyl)-($C_6$-$C_{10}$ aryl) and —($C_0$-$C_3$ alkyl)-($C_5$-$C_{10}$ heteroaryl), wherein the alkyl, heteroalkyl, cycloalkyl, heterocyclyl, aryl and heteroaryl groups are independently optionally substituted;

each occurrence of $R^2$ is independently selected from the group consisting of H, —$C_1$-$C_6$ alkyl, —OH, —$C_1$-$C_6$ alkoxy, halogen, —$NH_2$, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$;

n is 0, 1, 2, 3, or 4;

$R^3$ is selected from the group consisting of —(C=O)$_{0-1}$($C_1$-$C_6$ alkyl), —(C=O)$_{0-1}$($C_1$-$C_6$ heteroalkyl), —(C=O)$_{0-1}$($C_0$-$C_3$ alkyl)-($C_3$-$C_6$ cycloalkyl), —(C=O)$_{0-1}$($C_0$-$C_3$ alkyl)-($C_4$-$C_{10}$ heterocyclyl), —(C=O)$_{0-1}$($C_0$-$C_3$ alkyl)-($C_6$-$C_{10}$ aryl), —(C=O)$_{0-1}$($C_0$-$C_3$ alkyl)-($C_5$-$C_{10}$ heteroaryl), —($SO_2$)$_{0-1}$($C_1$-$C_6$ alkyl), —($SO_2$)$_{0-1}$($C_1$-$C_6$ heteroalkyl), —($SO_2$)$_{0-1}$($C_0$-$C_3$ alkyl)-($C_3$-$C_6$ cycloalkyl), —($SO_2$)$_{0-1}$($C_0$-$C_3$ alkyl)-($C_4$-$C_{10}$ heterocyclyl), —($SO_2$)$_{0-1}$($C_0$-$C_3$ alkyl)-($C_6$-$C_{10}$ aryl) and —($SO_2$)$_{0-1}$($C_0$-$C_3$ alkyl)-($C_5$-$C_{10}$ heteroaryl), wherein the alkyl, heteroalkyl, cycloalkyl, heterocyclyl, aryl and heteroaryl groups are independently optionally substituted; and, $R^4$ is N or CH;

(b) a compound of formula (II)

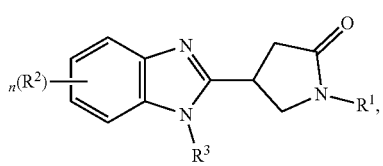

(II)

wherein in (II):

$R^1$ is selected from the group consisting of —$C_1$-$C_6$ alkyl, —$C_2$-$C_6$ alkenyl, —$C_2$-$C_6$ alkynyl, —$C_1$-$C_6$ heteroalkyl, —$C_2$-$C_6$ heteroalkenyl and —$C_2$-$C_6$ heteroalkynyl, wherein the alkyl, alkenyl, alkynyl, heteroalkyl, heteroalkenyl and heteroalkynyl are independently optionally substituted;

each occurrence of $R^2$ is independently selected from the group consisting of H, —$C_1$-$C_6$ alkyl, —OH, —$C_1$-$C_6$ alkoxy, halogen, —$NH_2$, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$;

n is 0, 1, 2, 3, or 4;

$R^3$ is selected from the group consisting of —($C_1$-$C_6$ alkyl)-$O_x$—($C_3$-$C_6$ cycloalkyl), —($C_1$-$C_6$ alkyl)-$O_x$—($C_4$-$C_{10}$ heterocyclyl), —($C_1$-$C_6$ alkyl)-$O_x$—($C_6$-$C_{10}$ aryl) and —($C_1$-$C_6$ alkyl)-$O_x$—($C_5$-$C_{10}$ heteroaryl), wherein the alkyl, cycloalkyl, heterocyclyl, aryl and heteroaryl groups are independently optionally substituted; and x is 0 or 1; and (c) a compound of formula (III)

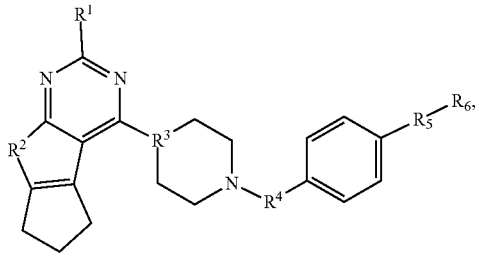

wherein in (III):

$R^1$ is selected from the group consisting of —($C_0$-$C_3$ alkyl)-($C_6$-$C_{10}$ aryl) and —($C_0$-$C_3$ alkyl)-($C_5$-$C_{10}$ heteroaryl), wherein the alkyl, aryl and heteroaryl groups are independently optionally substituted;

$R^2$ is NH, $NR^6$, S or O;

$R^3$ is N or CH;

$R^4$ is —C(=O)— or —S(=O)$_2$—;

$R^5$ is —C(=O)— or —S(=O)$_2$—; and, $R^6$ is selected from the group consisting of —$C_1$-$C_6$ alkyl, —$C_1$-$C_6$ heteroalkyl, —($C_0$-$C_3$ alkyl)-($C_3$-$C_6$ cycloalkyl), —($C_0$-$C_3$ alkyl)-($C_4$-$C_{10}$ heterocyclyl), —($C_0$-$C_3$ alkyl)-($C_6$-$C_{10}$ aryl) and —($C_0$-$C_3$ alkyl)-($C_5$-$C_{10}$ heteroaryl), wherein the alkyl, heteroalkyl, cycloalkyl, heterocyclyl, aryl and heteroaryl groups are independently optionally substituted.

2. The method of claim 1, wherein the disease or disorder is at least one selected from the group consisting of ischemia, seizure, traumatic brain injury, stroke, epilepsy, schizophrenia, and neurodegenerative diseases or disorders.

3. The method of claim 1, wherein the compound has at least one of the following effects in the subject:
   activates, stimulates, or upregulates the activity of a glutamate transporter;
   regulates extracellular glutamate concentrations;
   increases, induces or upregulates removal of glutamate from the neuronal synaptic cleft into neuroglia and neurons; or
   inhibits glutamate transport.

4. The method of claim 1, wherein the compound is selected from the group consisting of:
   1-allyl-4-(1-(4-(4-chloro-3-methylphenoxy)butyl)-1H-benzo[d]imidazol-2-yl)pyrrolidin-2-one;
   3-((4-cyclohexylpiperazin-1-yl)(1-phenethyl-1H-tetrazol-5-yl)methyl)-6-methoxy-quinolin-2(1H)-one;
   6-methoxy-3-((1-phenethyl-1H-tetrazol-5-yl)(4-(3-(trifluoromethyl) phenyl)piperazin-1-yl)methyl)quinolin-2 (1H)-one;
an enantiomer, diastereoisomer, salt or solvate thereof, and any mixtures thereof.

5. The method of claim 1, wherein the compound is selected from the group consisting of:
   (+)-3-((4-cyclohexylpiperazin-1-yl)(1-phenethyl-1H-tetrazol-5-yl)methyl)-6-methoxy-quinolin-2(1H)-one,
   (−)-3-((4-cyclohexylpiperazin-1-yl)(1-phenethyl-1H-tetrazol-5-yl)methyl)-6-methoxy-quinolin-2(1H)-one,
   (+)-6-methoxy-3-((1-phenethyl-1H-tetrazol-5-yl)(4-(3-(trifluoromethyl)phenyl)piperazin-1-yl)methyl)quinolin-2(1H)-one,
   (−)-6-methoxy-3-((1-phenethyl-1H-tetrazol-5-yl)(4-(3-(trifluoromethyl)phenyl)piperazin-1-yl)methyl)quinolin-2(1H)-one, and any mixtures thereof.

6. The method of claim 1, wherein at least one of the following applies:
   (a) $R^1$ is —($C_1$-$C_3$ alkyl)-($C_6$-$C_{10}$ aryl);
   (b) each occurrence of R2 is independently selected from the group consisting of —$C_1$-$C_6$ alkyl, —OH, —$C_1$-$C_6$ alkoxy, halogen, —$NH_2$, —$N(CH_3)_2$, —C(=O)OH, trifluoromethyl, —C≡N and —$NO_2$;
   (c) $R^3$ is selected from the group consisting of —($C_0$-$C_3$ alkyl)-($C_6$-$C_{10}$ aryl) and —(C=O)($C_0$-$C_3$ alkyl)-($C_6$-$C_{10}$ aryl).

7. The method of claim 1, wherein $R^3$ is substituted by trifluoromethyl.

8. The method of claim 1, wherein $R^1$ is $C_2$ alkyl-$C_6$ aryl.

9. The method of claim 1, wherein $R^3$ is optionally substituted phenyl.

10. The method of claim 1, wherein the compound is:

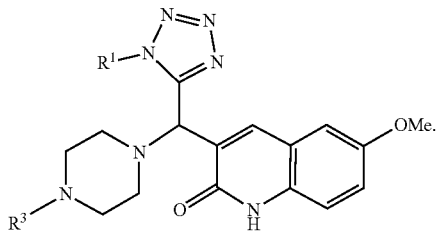

11. The method of claim 1, wherein $R^3$ is optionally substituted cyclohexyl or phenyl.

12. The method of claim 1, wherein the compound of formula (I) is selected from the group consisting of:

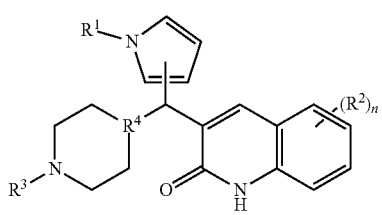

(Ia)

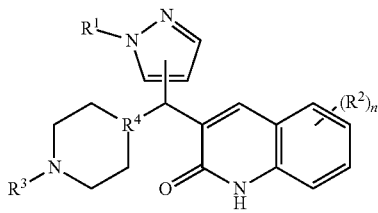

(Ib)

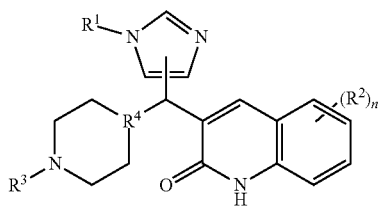

(Ic)

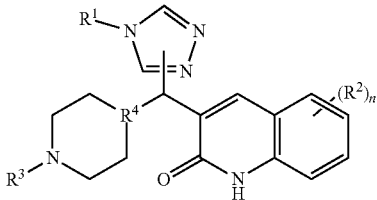

(Id)

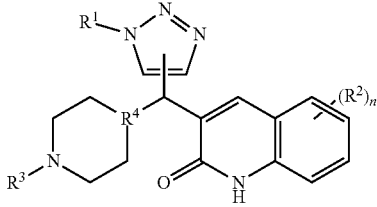

(Ie)

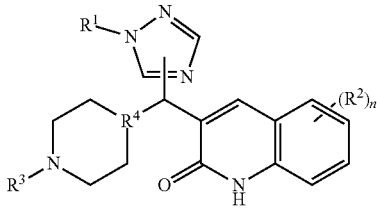

(If)

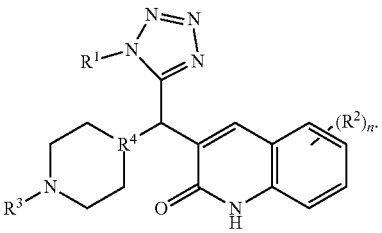

(Ig)

13. The method of claim 1, wherein at least one applies to the compound of formula (I):
   (a) $R^1$ is selected from the group consisting of —($C_1$-$C_3$ alkyl)-($C_3$-$C_6$ cycloalkyl), —($C_1$-$C_3$ alkyl)-($C_4$-$C_{10}$ heterocyclyl), —($C_1$-$C_3$ alkyl)-($C_6$-$C_{10}$ aryl) and —($C_1$-$C_3$ alkyl)-($C_5$-$C_{10}$ heteroaryl), wherein the alkyl, cycloalkyl, heterocyclyl, aryl and heteroaryl groups are independently optionally substituted;
   (b) $R^1$ is selected from the group consisting of —($C_1$-$C_3$ alkyl)-($C_6$-$C_{10}$ aryl) and —($C_1$-$C_3$ alkyl)-($C_5$-$C_{10}$ heteroaryl), wherein the alkyl, aryl and heteroaryl groups are independently optionally substituted;
   (c) each occurrence of $R^2$ is independently selected from the group consisting of H, —$C_1$-$C_6$ alkyl, —OH, —$C_1$-$C_6$ alkoxy, halogen, —$NH_2$, —$N(CH_3)_2$, —C(=O)OH, trifluoromethyl, —C≡N and —$NO_2$;
   (d) $R^3$ is selected from the group consisting of —($C_1$-$C_6$ alkyl), —($C_1$-$C_6$ heteroalkyl), —($C_0$-$C_3$ alkyl)-($C_3$-$C_6$ cycloalkyl), —($C_0$-$C_3$ alkyl)-($C_4$-$C_{10}$ heterocyclyl), —($C_0$-$C_3$ alkyl)-($C_6$-$C_{10}$ aryl), —($C_0$-$C_3$ alkyl)-($C_5$-$C_{10}$ heteroaryl), —(C=O)($C_0$-$C_3$ alkyl)-($C_6$-$C_{10}$ aryl), and —(C=O)($C_0$-$C_3$ alkyl)-($C_5$-$C_{10}$ heteroaryl), wherein the alkyl, heteroalkyl, cycloalkyl, heterocyclyl, aryl and heteroaryl groups are independently optionally substituted; and
   (e) n is 2 or 3.

14. The method of claim 1, wherein the compound of formula (I) is:

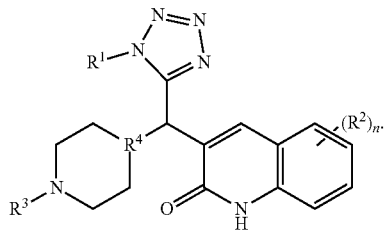
(Ig)

15. The method of claim 1, wherein the compound of formula (I) is:

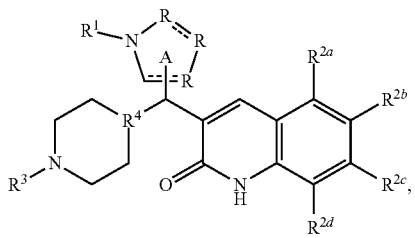
(Ih)

wherein:
$R^{2a}$, $R^{2c}$, and $R^{2d}$ are independently selected from the group consisting of H and $C_1$-$C_6$ alkyl, and $R^{2b}$ is OH or $C_1$-$C_6$ alkoxy.

16. The method of claim 1, wherein $R^{2a}$, $R^{2c}$, and $R^{2d}$ are each H.

17. The method of claim 1, wherein the compound is:

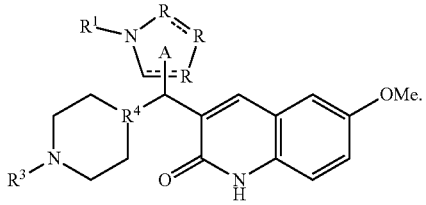
(Ii)

18. The method of claim 1, wherein the compound is:

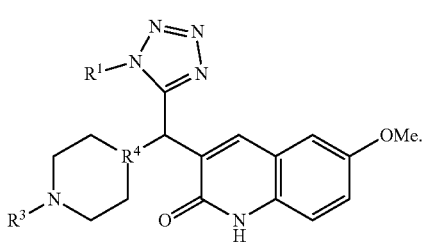
(Ij)

19. The method of claim 1, wherein the compound is selected from the group consisting of:

3-((4-cyclohexylpiperazin-1-yl)(1-phenethyl-1H-tetrazol-5-yl)methyl)-6-methoxy-quinolin-2(1H)-one (GT949)

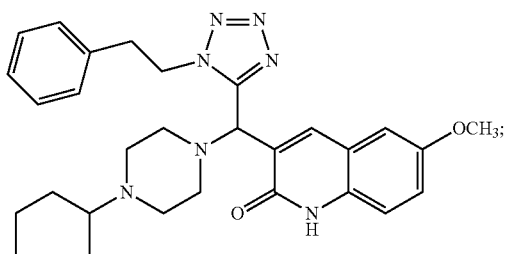

6-methoxy-3-((1-phenethyl-1H-tetrazol-5-yl)(4-(3-(trifluoromethyl)phenyl)piperazin-1-yl)methyl)quinolin-2(1H)-one (GT951)

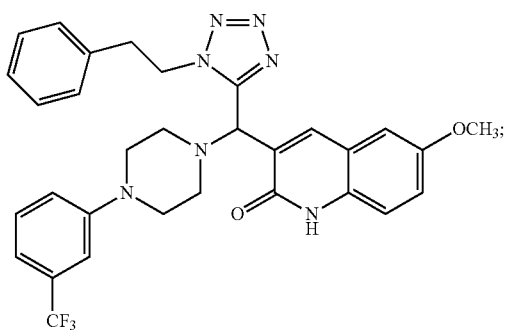 [SMILES: COc1ccc2[nH]c(=O)c(C(c3nnnn3CCc3ccccc3)N3CCN(c4cccc(C(F)(F)F)c4)CC3)cc2c1]

3-((4-(benzo[d][1,3]dioxol-5-ylmethyl)piperazin-1-yl)(1-phenethyl-1H-tetrazol-5-yl)methyl)-6,7-dimethylquinolin-2(1H)-one (GT835)

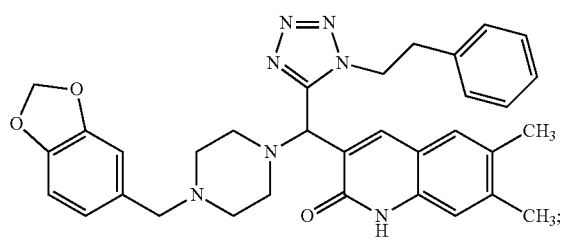 [SMILES: Cc1cc2cc(C(c3nnnn3CCc3ccccc3)N3CCN(Cc4ccc5c(c4)OCO5)CC3)c(=O)[nH]c2cc1C]

3-((4-(furan-2-carbonyl)piperazin-1-yl)(1-phenethyl-1H-tetrazol-5-yl)methyl)-6,8-dimethylquinolin-2(1H)-one (GT729)

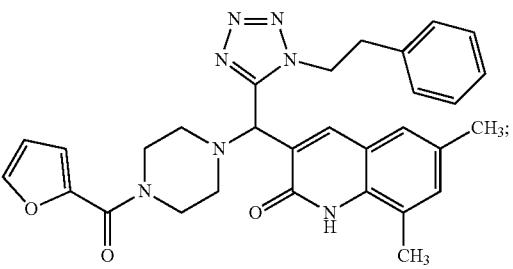 [SMILES: Cc1cc(C)c2[nH]c(=O)c(C(c3nnnn3CCc3ccccc3)N3CCN(C(=O)c4ccco4)CC3)cc2c1]

3-((4-(furan-2-carbonyl)piperazin-1-yl)(1-phenethyl-1H-tetrazol-5-yl)methyl)-5,7-dimethylquinolin-2(1H)-one (GT996)

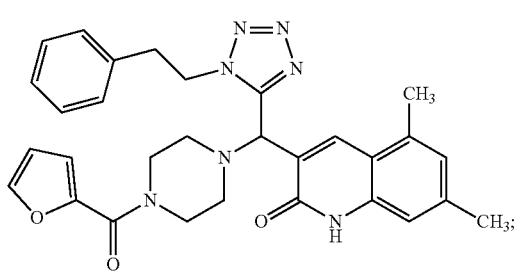 [SMILES: Cc1cc(C)c2cc(C(c3nnnn3CCc3ccccc3)N3CCN(C(=O)c4ccco4)CC3)c(=O)[nH]c2c1]

3-((4-(benzo[d][1,3]dioxol-5-ylmethyl)piperazin-1-yl)(1-phenethyl-1H-tetrazol-5-yl)methyl)-5,8-dimethylquinolin-2(1H)-one (GT867)

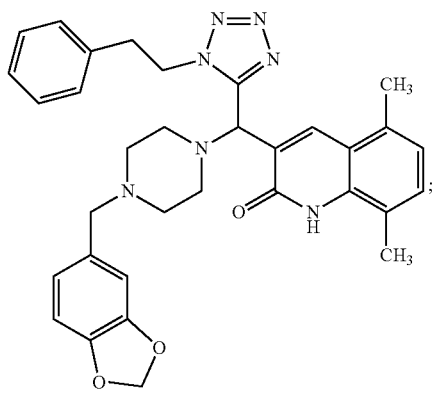 [SMILES: Cc1ccc(C)c2[nH]c(=O)c(C(c3nnnn3CCc3ccccc3)N3CCN(Cc4ccc5c(c4)OCO5)CC3)cc12]

an enantiomer, diastereoisomer, salt or solvate thereof, and any mixtures thereof.

20. The method of claim 1, wherein at least one the following applies to compound of formula (II):
   (a) n is 0;
   (b) x is 1;
   (c) $R^1$ is selected from the group consisting of —$C_2$-$C_6$ alkenyl and —$C_2$-$C_6$ alkynyl, wherein the alkenyl and alkynyl are independently optionally substituted;
   (d) $R^3$ is selected from the group consisting of —($C_1$-$C_6$ alkyl)-$O_x$—($C_6$-$C_{10}$ aryl) and —($C_1$-$C_6$ alkyl)-$O_x$—($C_5$-$C_{10}$ heteroaryl), wherein the alkyl, aryl and heteroaryl groups are independently optionally substituted.

21. The method of claim 1, wherein the compound is selected from the group consisting of:
   1-allyl-4-(1-(4-(4-chloro-3-methylphenoxy)butyl)-1H-benzo[d]imidazol-2-yl)pyrrolidin-2-one (GT939)

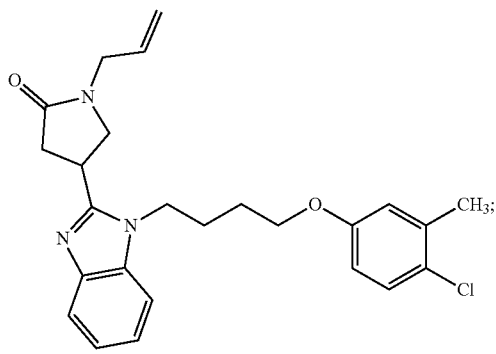 [SMILES: C=CCN1CC(c2nc3ccccc3n2CCCCOc2ccc(Cl)c(C)c2)CC1=O]

1-allyl-4-(1-(4-(3,4-dimethylphenoxy)butyl)-1H-benzo[d]imidazol-2-yl)pyrrolidin-2-one (GT938)

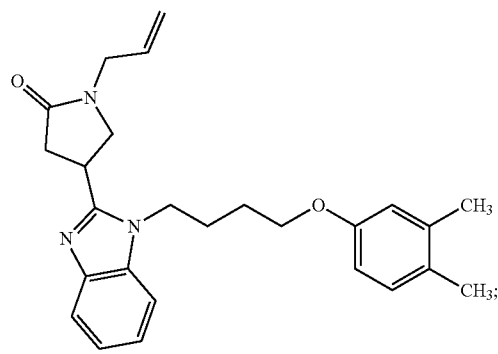 [SMILES: C=CCN1CC(c2nc3ccccc3n2CCCCOc2ccc(C)c(C)c2)CC1=O]

1-allyl-4-(1-(3-(4-(sec-butyl)phenoxy)propyl)-1H-benzo[d]imidazol-2-yl)pyrrolidin-2-one (GT922)

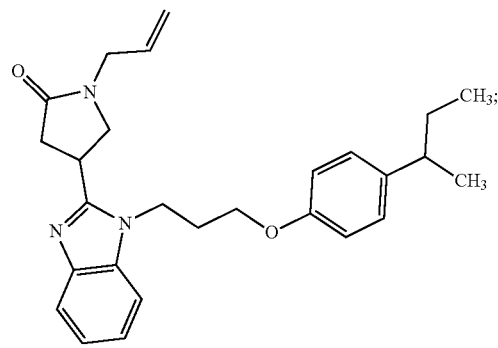 [SMILES: C=CCN1CC(c2nc3ccccc3n2CCCOc2ccc(C(C)CC)cc2)CC1=O]

an enantiomer, diastereoisomer, salt or solvate thereof, and any mixtures thereof.

22. The method of claim 1, wherein at least one applies to the compound of formula (III):
   (a) $R^1$ is —$C_6$-$C_{10}$ aryl or —$C_5$-$C_{10}$ heteroaryl, wherein the aryl and heteroaryl groups are independently optionally substituted;
   (b) $R^2$ is S;
   (c) $R^3$ is N;
   (d) $R^4$ is —C(=O)—;
   (e) $R^5$ is —S(=O)$_2$—; and
   (f) $R^6$ is —$C_1$-$C_6$ heteroalkyl or —$C_4$-$C_{10}$ heterocyclyl, wherein the heteroalkyl and heterocyclyl groups are independently optionally substituted.

23. The method of claim 1, wherein the compound is (4-(2-phenyl-6,7-dihydro-5H-cyclopenta[4,5]thieno[2,3-d]pyrimidin-4-yl)piperazin-1-yl)(4-(pyrrolidin-1-ylsulfonyl)phenyl)methanone (GT988), or an enantiomer, diastereoisomer, salt or solvate thereof:

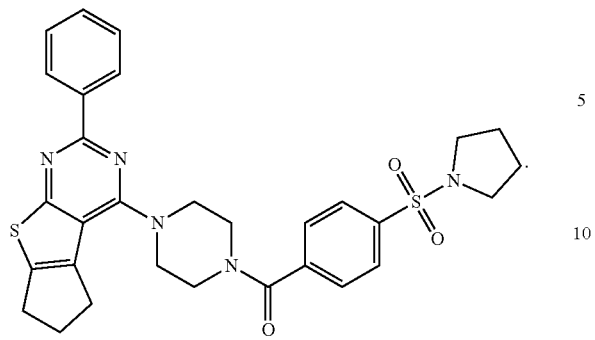
* * * * *